US012753227B2

(12) United States Patent
Zhang et al.

(10) Patent No.: US 12,753,227 B2
(45) Date of Patent: Oct. 6, 2026

(54) ANTIBODIES AGAINST HUMAN TSLP AND USE THEREOF

(71) Applicants: Beijing Wisdomab Biotechnology Co., Ltd., Beijing (CN); GENRIX (Shanghai) Biopharmaceutical Co.Ltd., Shanghai (CN); Chongqing Genrix Biopharmaceutical Co., Ltd., Chongqing (CN)

(72) Inventors: Xueping Zhang, Beijing (CN); Zhigang Liu, Beijing (CN); Xiaowei Zhou, Beijing (CN); Junjie Hu, Beijing (CN); Xiaobo Hao, Beijing (CN); Yulan Liu, Beijing (CN)

(73) Assignees: Beijing Wisdomab Biotechnology Co., Ltd., Beijing (CN); GENRIX (Shanghai) Biopharmaceutical Co.Ltd., Shanghai (CN); Chongqing Genrix Biopharmaceutical Co., Ltd., Chongqing (CN)

( * ) Notice: Subject to any disclaimer, the term of this patent is extended or adjusted under 35 U.S.C. 154(b) by 524 days.

(21) Appl. No.: 18/264,070

(22) PCT Filed: Jun. 17, 2021

(86) PCT No.: PCT/CN2021/100657
§ 371 (c)(1),
(2) Date: Aug. 2, 2023

(87) PCT Pub. No.: WO2022/166072
PCT Pub. Date: Aug. 11, 2022

(65) Prior Publication Data

US 2024/0132581 A1 Apr. 25, 2024
US 2024/0228605 A9 Jul. 11, 2024

(30) Foreign Application Priority Data

Feb. 3, 2021 (CN) ......................... 202110147687.1

(51) Int. Cl.
*C07K 16/24* (2006.01)
*A61K 39/00* (2006.01)

(52) U.S. Cl.
CPC ........ *C07K 16/244* (2013.01); *C07K 2317/31* (2013.01); *C07K 2317/55* (2013.01); *C07K 2317/622* (2013.01); *C07K 2317/76* (2013.01); *C07K 2317/92* (2013.01)

(58) Field of Classification Search
CPC .................................................. C07K 16/244
See application file for complete search history.

(56) References Cited

U.S. PATENT DOCUMENTS

| | | | |
|---|---|---|---|
| 4,816,567 | A | 3/1989 | Cabilly |
| 9,284,372 | B2 | 3/2016 | Corneau |
| 2007/0071675 | A1 | 3/2007 | Wu |
| 2010/0166766 | A1 | 7/2010 | Presta |
| 2013/0287777 | A1 | 10/2013 | Duffy |
| 2017/0327571 | A1 | 11/2017 | Liu |
| 2018/0296669 | A1 | 10/2018 | Parnes |
| 2018/0327489 | A1 | 11/2018 | Edwards |
| 2020/0308288 | A1 | 10/2020 | Poirier |
| 2022/0363781 | A1 | 11/2022 | Xiao |
| 2023/0212287 | A1 | 7/2023 | Liu |

FOREIGN PATENT DOCUMENTS

| | | | | |
|---|---|---|---|---|
| CN | 101605814 B | 2/2014 | | |
| CN | 105315371 A | 2/2016 | | |
| CN | 106831995 A | 6/2017 | | |
| CN | 108350070 A | 7/2018 | | |
| CN | 109195987 A | 1/2019 | | |
| CN | 109206514 A | 1/2019 | | |
| CN | 109678957 A | 4/2019 | | |
| CN | 110229232 A | 9/2019 | | |
| CN | 110573525 A | 12/2019 | | |
| CN | 111171150 * | 5/2020 | | ............. A61P 17/00 |
| CN | 111171150 A | 5/2020 | | |
| CN | 111196850 A | 5/2020 | | |
| CN | 114729037 A | 7/2022 | | |
| UA | 100531 C2 | 1/2013 | | |
| WO | WO 200177342 A1 | 10/2001 | | |
| WO | WO 2007096149 A1 | 8/2007 | | |
| WO | 2008076321 A1 | 6/2008 | | |
| WO | WO 2009100324 A1 | 8/2009 | | |
| WO | WO 2011056772 A1 | 5/2011 | | |
| WO | WO 2012083132 A2 | 6/2012 | | |
| WO | WO 2013165894 A2 | 11/2013 | | |
| WO | WO 2016142426 A1 | 9/2016 | | |
| WO | 2017042701 A1 | 3/2017 | | |
| WO | 2017174556 A1 | 10/2017 | | |
| WO | WO 2018191479 A1 | 10/2018 | | |
| WO | WO-2021155634 A1 * | 8/2021 | | ............. A61P 17/00 |

OTHER PUBLICATIONS

Almagro JC, Fransson J. Humanization of antibodies. Front Biosci. Jan. 1, 2008;13:1619-33. (Year: 2008).*
Edwards et al. The remarkable flexibility of the human antibody repertoire; isolation of over one thousand different antibodies to a single protein, BLyS. J Mol Biol Nov. 14, 2003;334(1):103-18. (Year: 2003).*
Kussie et al. A single engineered amino acid substitution changes antibody fine specificity.J Immunol. Jan. 1, 1994;152(1):146-52. (Year: 1994).*

(Continued)

*Primary Examiner* — Aurora M Fontainhas
*Assistant Examiner* — Jennifer A Benavides
(74) *Attorney, Agent, or Firm* — NIXON PEABODY LLP; Bradley M. Taub; Nicole D. Kling

(57) ABSTRACT

A bispecific antibody and a monoclonal antibody against human thymic stromal lymphopoietin (TSLP), and a use thereof.

14 Claims, 13 Drawing Sheets

Specification includes a Sequence Listing.

(56) References Cited

OTHER PUBLICATIONS

Machine translation of WO-2021155634-A1, published Aug. 12, 2021 <<retrieved from Patentscope on Feb. 2, 2026>> (Year: 2021).*
Machine translation of CN-111171150 , published May 19, 2020 <<retrieved from Patentscope on Feb. 3, 2026>> (Year: 2020).*
Merchant, A., Zhu, Z., Yuan, J. et al. An efficient route to human bispecific lgG. Nat Biotechnol 16, 677-681 (1998). (Year: 1998).*
Gauvreau, Gail M., et al. "Effects of an anti-TSLP antibody on allergen-induced asthmatic responses." New England Journal of Medicine 370.22 (2014): pp. 2102-2110.
Roitt I. et al., Immunology, Moskva, Mir, 2000, pp. 110-111 [English Description Provided].
Singer M. et al. Gens and genomes. Moskva, "Mir", 1998, v.1, pp. 63-64 [English Description Provided].
International Search Report and Written Opinion of International Searching Authority for International Patent Application No. PCT/CN2021/100657, mailed Nov. 1, 2021, with English language translation (29 pages).
Leonard, W. J.; "TSLP: finally in the limelight: TSLP is now revealed to be an important regulator of DC-mediated control of TH2-based human allergic responses, identifying a potentially new species-specific function for this cytokine"; Nat Immunol., vol. 3, No. 7, pp. 605-607; Jul. 2002 (3 pages).
Liu, Y. J. et al.; "TSLP: an epithelial cell cytokine that regulates T cell differentiation by conditioning dendritic cell maturation"; Annual Review of Immunology (2007); 25, pp. 193-219; Nov. 27, 2006 (30 pages).
Ziegler, S.F. et al.; "Sensing the outside world: TSLP regulates barrier immunity"; Nat Immunol ., vol. 11, No. 4, pp. 289-293; Apr. 2010; first published online Mar. 19, 2010 (5 pages).
Allakhverdi, Z. et al.; "Thymic stromal lymphopoietin as a mediator of crosstalk between bronchial smooth muscle and mast cells"; Journal of Allergy and Clinical Immunology 123, pp. 958-960; Apr. 2009; DOI: 10.1016/j.jaci.2009.01.068 (5 pages).
Allakhverdi, Z. et al.; "Thymic stromal lymphopoietin is released by human epithelial cells in response to microbes, trauma, or inflammation and potently activates mast cells"; J. Exp. Med., vol. 204, No. 2, pp. 253-258; published Jan. 22, 2007 (6 pages).
Lee, H.C. et al.; "Inducible expression of the proallergic cytokine thymic stromal lymphopoietin in airway epithelial cells is controlled by NFκB"; Proceedings of the National Academy of Sciences, vol. 104, No. 3, pp. 914-919; Jan. 16, 2007 (6 pages).
Ying, S. et al.; "Expression and cellular provenance of thymic stromal lymphopoietin and chemokines in patients with severe asthma and chronic obstructive pulmonary disease": Journal of Allergy and Clinical Immunology 2008, vol. 181, pp. 2790-2798; copyright 2008 (10 pages).
Keqin Zhang et al.; "Constitutive and inducible thymic stromal lymphopoietin expression in human airway smooth muscle cells: role in chronic obstructive pulmonary disease"; American Journal of Physiology Lung Cellular & Molecular Physiology, vol. 293, L375-L382; first published May 18, 2007; DOI: 10.1152/ajplung.00045.2007 (9 pages).
Ying, S. et al.; "Thymic stromal lymphopoietin expression is increased in asthmatic airways and correlates with expression of th2-attracting chemokines and disease severity"; The Journal of Immunology, vol. 174, pp. 8183-8190; copyright 2005; DOI: 10.4049/jimmunol.174.12.8183 (9 pages).
Kashyap, M. et al.; "Thymic stromal lymphopoietin is produced by dendritic cells"; The Journal of Immunology, vol. 187, pp. 1207-1211; accepted for publication May 17, 2011 (5 pages).
Soumelis, V. et al.; "Human epithelial cells trigger dendritic cell mediator allergic inflammation by producing TSLP"; Nat Immunol. vol. 3, No. 7, pp. 673-680; published Jun. 10, 2002 (8 pages).
Watanabe, N. et al.; "Human thymic stromal lymphopoietin promotes dendritic cell-mediated CD4+ T cell homeostatic expansion"; Nat Immunol., vol. 5, No. 4, pp. 426-434; Apr. 2004 (9 pages).
Moon, P.D. et al.; "Naringenin suppresses the production of thymic stromal lymphopoietin through the blockade of RIP2 and caspase-1 signal cascade in mast cells"; European Journal of Pharmacology, vol. 671, pp. 128-132; Sep. 24, 2011 (5 pages).
Sokol, C. et al.; "A mechanism for the initiation of allergen-induced T helper type 2 responses"; Nature Immunology, vol. 9, No. 3, pp. 310-318; Mar. 2008; published online Dec. 21, 2007 (9 pages).
He R. et al.; "Thymic stromal lymphopoietin"; Ann. N.Y. Acad. Sci., vol. 1183, pp. 13-24; 2010 (12 pages).
Oyoshi, M.K. et al.; "Mechanical injury polarizes skin dendritic cells to elicit a T (H) 2 response by inducing cutaneous thymic stromal lymphopoietin expression"; Journal of Allergy & Clinical Immunology, vol. 126, No. 5, pp. 976-984; e975; copyright 2010 (14 pages).
Hai yan Tu et al.; "Signal transduction in respiratory syncytial virus infection-induced thymic stromal lymphopoietin expression in human epithelial cells"; Journal of Southern Medical University, vol. 27, No. 10, pp. 1581-1583; 2007 (4 pages).
Medoff, B.D. et al.; "CARMA3 mediates lysophoshatidic acid-stimulated cytokine secretion by bronchial epithelial cells"; American Journal of Respiratory Cell and Molecular Biology, vol. 40, pp. 286-294; Aug. 28, 2008; DOI: 10.165/rcmb.2008-01290C (9 pages).
Park, L.S. et al.; "Cloning of the murine thymic stromal lymphopoietin (TSLP) receptor: formation of a functional heteromeric complex requires interleukin 7 receptor"; The Journal of Experimental Medicine, vol. 192, No. 5, pp. 659-670; Sep. 4, 2000 (11 pages).
Verstraete, K. et al.; "Structure and antagonism of the receptor complex mediated by human TSLP in allergy and asthma"; Nature Communications, 8:14937; Apr. 3, 2017; DOI: 10.1037/ncomms14937 (17 pages).
Bateman, E.D. et al.; "GINA Report, Global Strategy for Asthma Management and Prevention"; Eur. Respir, J. vol. 31, No. 1, pp. 143-178; 2008; DOI: 10.1183/09031936.00138707; retrieved from: http://www.ginasthma.com (36 pages).
Von Bülow, A. et al.; "The prevalence of severe asthma and low asthma control among Danish adults"; The Journal of Allergy and Clinical Immunology: In Practice, vol. 2, No. 6, pp. 759-673; Nov./Dec. 2014 (11 pages).
Reche, P.A. et al.; "Human thyroid stromal lymphopoietin preferentially stimulates myeloid cells"; The Journal of Immunology, vol. 167, pp. 336-343; copyright 2001; DOI: 10.4049/jimmunol.org/167.1.336 (9 pages).
Zhou, B. et al.; "Thymic stromal lymphopoietin as a key initiator of allergic airway inflammation in mice"; Nat. Immunol., vol. 6, No. 10, pp. 1047-1053; Oct. 2005; DOI: 10.1038/ni1247 (7 pages).
Zhuang gui Chen et al.; "Neutralization of TSLP inhibits airway remodeling in a murine model of allergic asthma induced by chronic exposure to house dust mite"; PLoS One 8(1): e51268; Jan. 2, 2013; DOI: 10.1371/journal.pone.0051268 (12 pages).
He, R. et al.; "TSLP acts on infiltrating effector T cells to drive allergic skin inflammation"; Proc Natl Acad Sci USA 105(33), 11875-11880; Aug. 19, 2008 (6 pages).
Corren, J. et al.; "Tezepelumab in Adults with Uncontrolled Asthma"; New England Journal of Medicine, 377(10), 936-946; Sep. 7, 2017 (11 pages).
Verstraete K. et al.; "Structure and antagonism of the receptor complex mediated by human TSLP in allergy and asthma"; Nat Commun [J], 8: 14937; published Apr. 3, 2017 (17 pages).
Merchant, A. M. et al.; "An efficient route to human bispecific IgG"; Nature Biotechnology, vol. 16, pp. 677-681; Jun. 4, 1998 (5 pages).
Al-Lazikani, B. et al.; "Standard Conformations for the Canonical Structures of Immunoglobulins"; J. Mol. Biol., vol. 273, pp. 927-948 (1997) (22 pages).
Martin, A. et al.; "modeling antibody hypervariable loops: A combined algorithm"; Proc. Natl. Acad. Sci., USA, vol. 86, pp. 9268-9272; Dec. 1989 (5 pages).
Morrison, S. et al.; "Chimeric human antibody molecules: Mouse antigen-binding domains with human constant region domains"; Proc. Natl. Acad. Sci. USA, vol. 81, pp. 6851-6855; Nov. 1984 (5 pages).
Tan P. et al.; "'Superhumanized' antibodies: reduction of immunogenic potential by complementarity-determining region grafting with human germline sequences: application to an anti-CD28"; J Immunol., vol. 169, No. 2, pp. 1119-1125; copyright 2002 (8 pages).

(56) References Cited

OTHER PUBLICATIONS

朱建光等，抗TSLP全人源单链亢体筛选与初步鉴定，中国免疫学杂志，2014年第30卷第12期，第1662-1665和1669页 (Zhu, Jianguang et al.; "Selection and Identification of Full Human scFv Against TSLP"; Chinese Journal of Immunology, vol. 30, No. 12, pp. 1662-1665 and 1669; Dec. 31, 2014; DOI: 10.3969/j. issn. 1000-484X.2014.12.016 (5 pages).

Venkataramani, S. et al.; "Design and characterization of Zweimab and Doppelmab, high affinity dual antagonistic anti-TSLP/IL13 bispecific antibodies"; Biochemical and Biophysical Research Communications, vol. 504, pp. 19-24; Aug. 17, 2018; https://doi.org/10.116/j.bbrc.2018.08.064 (6 pages).

Eger, K. A. et, al.; "The emergence of new biologies for severe asthma"; Current Opinion in Pharmacology, vol. 46, pp. 108-115; Jun. 21, 2019 (8 pages).

先德群等，抗TSLP全人源单链亢体的体外亲和力成熟，中国免疫学杂志，2017年，第33卷，第9期，第1301-1305页 (Xian Dequn, et al.; "Afinity maturation of human scFv anti-TSLP in vitro"; Chinese Journal of Immunology, 2017, vol. 33, No. 9, pp. 1301-1305. (5 pages).

* cited by examiner

C

D

A

B

C

D

E

A

B

C

SEQUENCE LISTING

```
<160> NUMBER OF SEQ ID NOS: 43

<210> SEQ ID NO 1
<211> LENGTH: 131
<212> TYPE: PRT
<213> ORGANISM: Homo sapiens

<400> SEQUENCE: 1

Tyr Asp Phe Thr Asn Cys Asp Phe Glu Lys Ile Lys Ala Ala Tyr Leu
1               5                   10                  15

Ser Thr Ile Ser Lys Asp Leu Ile Thr Tyr Met Ser Gly Thr Lys Ser
            20                  25                  30

Thr Glu Phe Asn Asn Thr Val Ser Cys Ser Asn Arg Pro His Cys Leu
        35                  40                  45

Thr Glu Ile Gln Ser Leu Thr Phe Asn Pro Thr Ala Gly Cys Ala Ser
    50                  55                  60

Leu Ala Lys Glu Met Phe Ala Met Lys Thr Lys Ala Ala Leu Ala Ile
65                  70                  75                  80

Trp Cys Pro Gly Tyr Ser Glu Thr Gln Ile Asn Ala Thr Gln Ala Met
                85                  90                  95

Lys Lys Arg Arg Lys Arg Lys Val Thr Thr Asn Lys Cys Leu Glu Gln
            100                 105                 110

Val Ser Gln Leu Gln Gly Leu Trp Arg Arg Phe Asn Arg Pro Leu Leu
        115                 120                 125

Lys Gln Gln
    130


<210> SEQ ID NO 2
<211> LENGTH: 63
```

```
<212> TYPE: PRT
<213> ORGANISM: Homo sapiens

<400> SEQUENCE: 2

Met Phe Ala Met Lys Thr Lys Ala Ala Leu Ala Ile Trp Cys Pro Gly
1               5                   10                  15

Tyr Ser Glu Thr Gln Ile Asn Ala Thr Gln Ala Met Lys Lys Arg Arg
            20                  25                  30

Lys Arg Lys Val Thr Thr Asn Lys Cys Leu Glu Gln Val Ser Gln Leu
        35                  40                  45

Gln Gly Leu Trp Arg Arg Phe Asn Arg Pro Leu Leu Lys Gln Gln
    50                  55                  60


<210> SEQ ID NO 3
<211> LENGTH: 121
<212> TYPE: PRT
<213> ORGANISM: Mus musculus

<400> SEQUENCE: 3

Tyr Asn Phe Ser Asn Cys Asn Phe Thr Ser Ile Thr Lys Ile Tyr Cys
1               5                   10                  15

Asn Ile Ile Phe His Asp Leu Thr Gly Asp Leu Lys Gly Ala Lys Phe
            20                  25                  30

Glu Gln Ile Glu Asp Cys Glu Ser Lys Pro Ala Cys Leu Leu Lys Ile
        35                  40                  45

Glu Tyr Tyr Thr Leu Asn Pro Ile Pro Gly Cys Pro Ser Leu Pro Asp
    50                  55                  60

Lys Thr Phe Ala Arg Arg Thr Arg Glu Ala Leu Asn Asp His Cys Pro
65                  70                  75                  80

Gly Tyr Pro Glu Thr Glu Arg Asn Asp Gly Thr Gln Glu Met Ala Gln
                85                  90                  95

Glu Val Gln Asn Ile Cys Leu Asn Gln Thr Ser Gln Ile Leu Arg Leu
            100                 105                 110

Trp Tyr Ser Phe Met Gln Ser Pro Glu
        115                 120


<210> SEQ ID NO 4
<211> LENGTH: 131
<212> TYPE: PRT
<213> ORGANISM: Macaca fascicularis

<400> SEQUENCE: 4

Tyr Asp Phe Thr Asn Cys Asp Phe Gln Lys Ile Glu Ala Asp Tyr Leu
1               5                   10                  15

Arg Thr Ile Ser Lys Asp Leu Ile Thr Tyr Met Ser Gly Thr Lys Ser
            20                  25                  30

Thr Asp Phe Asn Asn Thr Val Ser Cys Ser Asn Arg Pro His Cys Leu
        35                  40                  45

Thr Glu Ile Gln Ser Leu Thr Phe Asn Pro Thr Pro Arg Cys Ala Ser
    50                  55                  60

Leu Ala Lys Glu Met Phe Ala Arg Lys Thr Lys Ala Thr Leu Ala Leu
65                  70                  75                  80

Trp Cys Pro Gly Tyr Ser Glu Thr Gln Ile Asn Ala Thr Gln Ala Met
                85                  90                  95

Lys Lys Arg Arg Lys Arg Lys Val Thr Thr Asn Lys Cys Leu Glu Gln
            100                 105                 110

Val Ser Gln Leu Leu Gly Leu Trp Arg Arg Phe Ile Arg Thr Leu Leu
```

```
        115                 120                 125

Lys Lys Gln
    130


<210> SEQ ID NO 5
<211> LENGTH: 126
<212> TYPE: PRT
<213> ORGANISM: Artificial Sequence
<220> FEATURE:
<223> OTHER INFORMATION: hTSLP1 mutant with the deletion of furin
      recognition site

<400> SEQUENCE: 5

Tyr Asp Phe Thr Asn Cys Asp Phe Glu Lys Ile Lys Ala Ala Tyr Leu
1               5                   10                  15

Ser Thr Ile Ser Lys Asp Leu Ile Thr Tyr Met Ser Gly Thr Lys Ser
            20                  25                  30

Thr Glu Phe Asn Asn Thr Val Ser Cys Ser Asn Arg Pro His Cys Leu
        35                  40                  45

Thr Glu Ile Gln Ser Leu Thr Phe Asn Pro Thr Ala Gly Cys Ala Ser
    50                  55                  60

Leu Ala Lys Glu Met Phe Ala Met Lys Thr Lys Ala Ala Leu Ala Ile
65                  70                  75                  80

Trp Cys Pro Gly Tyr Ser Glu Thr Gln Ile Asn Ala Thr Gln Ala Met
                85                  90                  95

Lys Lys Val Thr Thr Asn Lys Cys Leu Glu Gln Val Ser Gln Leu Gln
            100                 105                 110

Gly Leu Trp Arg Arg Phe Asn Arg Pro Leu Leu Lys Gln Gln
        115                 120                 125


<210> SEQ ID NO 6
<211> LENGTH: 58
<212> TYPE: PRT
<213> ORGANISM: Artificial Sequence
<220> FEATURE:
<223> OTHER INFORMATION: hTSLP2 mutant with the deletion of furin
      recognition site

<400> SEQUENCE: 6

Met Phe Ala Met Lys Thr Lys Ala Ala Leu Ala Ile Trp Cys Pro Gly
1               5                   10                  15

Tyr Ser Glu Thr Gln Ile Asn Ala Thr Gln Ala Met Lys Lys Val Thr
            20                  25                  30

Thr Asn Lys Cys Leu Glu Gln Val Ser Gln Leu Gln Gly Leu Trp Arg
        35                  40                  45

Arg Phe Asn Arg Pro Leu Leu Lys Gln Gln
    50                  55


<210> SEQ ID NO 7
<211> LENGTH: 126
<212> TYPE: PRT
<213> ORGANISM: Artificial Sequence
<220> FEATURE:
<223> OTHER INFORMATION: mfTSLP1 mutant with the deletion of furin
      recognition site

<400> SEQUENCE: 7

Tyr Asp Phe Thr Asn Cys Asp Phe Gln Lys Ile Glu Ala Asp Tyr Leu
1               5                   10                  15

Arg Thr Ile Ser Lys Asp Leu Ile Thr Tyr Met Ser Gly Thr Lys Ser
            20                  25                  30
```

Thr Asp Phe Asn Asn Thr Val Ser Cys Ser Asn Arg Pro His Cys Leu
35 40 45

Thr Glu Ile Gln Ser Leu Thr Phe Asn Pro Thr Pro Arg Cys Ala Ser
50 55 60

Leu Ala Lys Glu Met Phe Ala Arg Lys Thr Lys Ala Thr Leu Ala Leu
65 70 75 80

Trp Cys Pro Gly Tyr Ser Glu Thr Gln Ile Asn Ala Thr Gln Ala Met
85 90 95

Lys Lys Val Thr Thr Asn Lys Cys Leu Glu Gln Val Ser Gln Leu Leu
100 105 110

Gly Leu Trp Arg Arg Phe Ile Arg Thr Leu Leu Lys Lys Gln
115 120 125

<210> SEQ ID NO 8
<211> LENGTH: 6
<212> TYPE: PRT
<213> ORGANISM: Artificial Sequence
<220> FEATURE:
<223> OTHER INFORMATION: His tag

<400> SEQUENCE: 8

His His His His His His
1 5

<210> SEQ ID NO 9
<211> LENGTH: 232
<212> TYPE: PRT
<213> ORGANISM: Homo sapiens

<400> SEQUENCE: 9

Glu Pro Lys Ser Ser Asp Lys Thr His Thr Cys Pro Pro Cys Pro Ala
1 5 10 15

Pro Glu Leu Leu Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Asp Glu Leu Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

```
Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 10
<211> LENGTH: 232
<212> TYPE: PRT
<213> ORGANISM: Mus musculus

<400> SEQUENCE: 10

Pro Arg Gly Pro Thr Ile Lys Pro Cys Pro Pro Cys Lys Cys Pro Ala
1               5                   10                  15

Pro Asn Leu Leu Gly Gly Pro Ser Val Phe Ile Phe Pro Pro Lys Ile
            20                  25                  30

Lys Asp Val Leu Met Ile Ser Leu Ser Pro Ile Val Thr Cys Val Val
        35                  40                  45

Val Asp Val Ser Glu Asp Asp Pro Asp Val Gln Ile Ser Trp Phe Val
    50                  55                  60

Asn Asn Val Glu Val His Thr Ala Gln Thr Gln Thr His Arg Glu Asp
65                  70                  75                  80

Tyr Asn Ser Thr Leu Arg Val Val Ser Ala Leu Pro Ile Gln His Gln
                85                  90                  95

Asp Trp Met Ser Gly Lys Glu Phe Lys Cys Lys Val Asn Asn Lys Asp
            100                 105                 110

Leu Pro Ala Pro Ile Glu Arg Thr Ile Ser Lys Pro Lys Gly Ser Val
        115                 120                 125

Arg Ala Pro Gln Val Tyr Val Leu Pro Pro Pro Glu Glu Glu Met Thr
    130                 135                 140

Lys Lys Gln Val Thr Leu Thr Cys Met Val Thr Asp Phe Met Pro Glu
145                 150                 155                 160

Asp Ile Tyr Val Glu Trp Thr Asn Asn Gly Lys Thr Glu Leu Asn Tyr
                165                 170                 175

Lys Asn Thr Glu Pro Val Leu Asp Ser Asp Gly Ser Tyr Phe Met Tyr
            180                 185                 190

Ser Lys Leu Arg Val Glu Lys Lys Asn Trp Val Glu Arg Asn Ser Tyr
        195                 200                 205

Ser Cys Ser Val Val His Glu Gly Leu His Asn His His Thr Thr Lys
    210                 215                 220

Ser Phe Ser Arg Thr Pro Gly Lys
225                 230


<210> SEQ ID NO 11
<211> LENGTH: 330
<212> TYPE: PRT
<213> ORGANISM: Homo sapiens

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 12
<211> LENGTH: 326
<212> TYPE: PRT
<213> ORGANISM: Homo sapiens

<400> SEQUENCE: 12

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110
```

```
Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 13
<211> LENGTH: 327
<212> TYPE: PRT
<213> ORGANISM: Homo sapiens

<400> SEQUENCE: 13

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
```

145 150 155 160

Gly Val Glu Val His Asn Ala Lys Thr Lys Pro Arg Glu Glu Gln Phe
165 170 175

Asn Ser Thr Tyr Arg Val Val Ser Val Leu Thr Val Leu His Gln Asp
180 185 190

Trp Leu Asn Gly Lys Glu Tyr Lys Cys Lys Val Ser Asn Lys Gly Leu
195 200 205

Pro Ser Ser Ile Glu Lys Thr Ile Ser Lys Ala Lys Gly Gln Pro Arg
210 215 220

Glu Pro Gln Val Tyr Thr Leu Pro Pro Ser Gln Glu Glu Met Thr Lys
225 230 235 240

Asn Gln Val Ser Leu Thr Cys Leu Val Lys Gly Phe Tyr Pro Ser Asp
245 250 255

Ile Ala Val Glu Trp Glu Ser Asn Gly Gln Pro Glu Asn Asn Tyr Lys
260 265 270

Thr Thr Pro Pro Val Leu Asp Ser Asp Gly Ser Phe Phe Leu Tyr Ser
275 280 285

Arg Leu Thr Val Asp Lys Ser Arg Trp Gln Glu Gly Asn Val Phe Ser
290 295 300

Cys Ser Val Met His Glu Ala Leu His Asn His Tyr Thr Gln Lys Ser
305 310 315 320

Leu Ser Leu Ser Leu Gly Lys
325

<210> SEQ ID NO 14
<211> LENGTH: 324
<212> TYPE: PRT
<213> ORGANISM: Mus musculus

<400> SEQUENCE: 14

Ala Lys Thr Thr Pro Pro Ser Val Tyr Pro Leu Ala Pro Gly Ser Ala
1 5 10 15

Ala Gln Thr Asn Ser Met Val Thr Leu Gly Cys Leu Val Lys Gly Tyr
20 25 30

Phe Pro Glu Pro Val Thr Val Thr Trp Asn Ser Gly Ser Leu Ser Ser
35 40 45

Gly Val His Thr Phe Pro Ala Val Leu Glu Ser Asp Leu Tyr Thr Leu
50 55 60

Ser Ser Ser Val Thr Val Pro Ser Ser Pro Arg Pro Ser Glu Thr Val
65 70 75 80

Thr Cys Asn Val Ala His Pro Ala Ser Ser Thr Lys Val Asp Lys Lys
85 90 95

Ile Val Pro Arg Asp Cys Gly Cys Lys Pro Cys Ile Cys Thr Val Pro
100 105 110

Glu Val Ser Ser Val Phe Ile Phe Pro Pro Lys Pro Lys Asp Val Leu
115 120 125

Thr Ile Thr Leu Thr Pro Lys Val Thr Cys Val Val Val Asp Ile Ser
130 135 140

Lys Asp Asp Pro Glu Val Gln Phe Ser Trp Phe Val Asp Asp Val Glu
145 150 155 160

Val His Thr Ala Gln Thr Gln Pro Arg Glu Glu Gln Phe Asn Ser Thr
165 170 175

Phe Arg Ser Val Ser Glu Leu Pro Ile Met His Gln Asp Trp Leu Asn
180 185 190

```
Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asn Thr Asn Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys


<210> SEQ ID NO 15
<211> LENGTH: 330
<212> TYPE: PRT
<213> ORGANISM: Mus musculus

<400> SEQUENCE: 15

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240
```

```
Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330


<210> SEQ ID NO 16
<211> LENGTH: 107
<212> TYPE: PRT
<213> ORGANISM: Homo sapiens

<400> SEQUENCE: 16

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 17
<211> LENGTH: 106
<212> TYPE: PRT
<213> ORGANISM: Homo sapiens

<400> SEQUENCE: 17

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 18
<211> LENGTH: 107
```

<212> TYPE: PRT
<213> ORGANISM: Mus musculus

<400> SEQUENCE: 18

Arg Ala Asp Ala Ala Pro Thr Val Ser Ile Phe Pro Pro Ser Ser Glu
1 5 10 15

Gln Leu Thr Ser Gly Gly Ala Ser Val Val Cys Phe Leu Asn Asn Phe
20 25 30

Tyr Pro Lys Asp Ile Asn Val Lys Trp Lys Ile Asp Gly Ser Glu Arg
35 40 45

Gln Asn Gly Val Leu Asn Ser Trp Thr Asp Gln Asp Ser Lys Asp Ser
50 55 60

Thr Tyr Ser Met Ser Ser Thr Leu Thr Leu Thr Lys Asp Glu Tyr Glu
65 70 75 80

Arg His Asn Ser Tyr Thr Cys Glu Ala Thr His Lys Thr Ser Thr Ser
85 90 95

Pro Ile Val Lys Ser Phe Asn Arg Asn Glu Cys
100 105

<210> SEQ ID NO 19
<211> LENGTH: 106
<212> TYPE: PRT
<213> ORGANISM: Mus musculus

<400> SEQUENCE: 19

Gly Gln Pro Lys Ser Ser Pro Ser Val Thr Leu Phe Pro Pro Ser Ser
1 5 10 15

Glu Glu Leu Glu Thr Asn Lys Ala Thr Leu Val Cys Thr Ile Thr Asp
20 25 30

Phe Tyr Pro Gly Val Val Thr Val Asp Trp Lys Val Asp Gly Thr Pro
35 40 45

Val Thr Gln Gly Met Glu Thr Thr Gln Pro Ser Lys Gln Ser Asn Asn
50 55 60

Lys Tyr Met Ala Ser Ser Tyr Leu Thr Leu Thr Ala Arg Ala Trp Glu
65 70 75 80

Arg His Ser Ser Tyr Ser Cys Gln Val Thr His Glu Gly His Thr Val
85 90 95

Glu Lys Ser Leu Ser Arg Ala Asp Cys Ser
100 105

<210> SEQ ID NO 20
<211> LENGTH: 121
<212> TYPE: PRT
<213> ORGANISM: Artificial Sequence
<220> FEATURE:
<223> OTHER INFORMATION: the heavy chain variable region of the humanized antibody H1A10+L3E8-M1

<400> SEQUENCE: 20

Gln Val Gln Leu Val Gln Ser Gly Ala Glu Val Lys Lys Pro Gly Ala
1 5 10 15

Ser Val Lys Val Ser Cys Lys Ala Ser Gly Tyr Ala Phe Ser Asn Tyr
20 25 30

Trp Met Asn Trp Val Arg Gln Ala Pro Gly Gln Gly Leu Glu Trp Met
35 40 45

Gly Gln Ile Phe Pro Gly Asp Ser Asp Thr Asp Tyr Asp Gln Lys Phe
50 55 60

Gln Gly Arg Val Thr Met Thr Arg Asp Thr Ser Thr Ser Thr Val Tyr

```
65                  70                  75                  80

Met Glu Leu Ser Ser Leu Arg Ser Glu Asp Thr Ala Val Tyr Tyr Cys
                85                  90                  95

Ala Arg Ala Gly Tyr Tyr Arg Gly Tyr Tyr Ala Met Asp Tyr Trp Gly
            100                 105                 110

Gln Gly Thr Thr Val Thr Val Ser Ser
        115                 120


<210> SEQ ID NO 21
<211> LENGTH: 108
<212> TYPE: PRT
<213> ORGANISM: Artificial Sequence
<220> FEATURE:
<223> OTHER INFORMATION: the light chain variable region L3E8-M1 of the
      humanized antibody H1A10+L3E8-M1

<400> SEQUENCE: 21

Glu Ile Val Met Thr Gln Ser Pro Ala Thr Leu Ser Val Ser Pro Gly
1               5                   10                  15

Glu Arg Ala Thr Leu Ser Cys Ser Val Ser Ser Ser Ile Ser Ser Ser
            20                  25                  30

Asn Leu His Trp Tyr Gln Gln Lys Pro Gly Gln Ala Pro Arg Pro Trp
        35                  40                  45

Ile Tyr Gly Thr Ser Asn Leu Ala Ser Gly Ile Pro Ala Arg Phe Ser
    50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Trp Ser Ser Tyr Pro
                85                  90                  95

Leu Thr Phe Gly Gln Gly Thr Lys Leu Glu Ile Lys
            100                 105


<210> SEQ ID NO 22
<211> LENGTH: 122
<212> TYPE: PRT
<213> ORGANISM: Artificial Sequence
<220> FEATURE:
<223> OTHER INFORMATION: the heavy chain variable region of the anti-
      human TSLP control antibody Tezepelumab

<400> SEQUENCE: 22

Gln Met Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Thr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys His Tyr Ala Asp Ser Val
    50                  55                  60

Lys Gly Arg Phe Thr Ile Thr Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Ala Arg Ala Pro Gln Trp Glu Leu Val His Glu Ala Phe Asp Ile Trp
            100                 105                 110

Gly Gln Gly Thr Met Val Thr Val Ser Ser
        115                 120
```

```
<210> SEQ ID NO 23
<211> LENGTH: 108
<212> TYPE: PRT
<213> ORGANISM: Artificial Sequence
<220> FEATURE:
<223> OTHER INFORMATION: the light chain variable region of the anti-
      human TSLP control antibody Tezepelumab

<400> SEQUENCE: 23

Ser Tyr Val Leu Thr Gln Pro Pro Ser Val Ser Val Ala Pro Gly Gln
1               5                   10                  15

Thr Ala Arg Ile Thr Cys Gly Gly Asn Asn Leu Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Trp Ile Pro Glu Arg Phe Ser Gly Ser
    50                  55                  60

Asn Ser Gly Asn Thr Ala Thr Leu Thr Ile Ser Arg Gly Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105


<210> SEQ ID NO 24
<211> LENGTH: 116
<212> TYPE: PRT
<213> ORGANISM: Artificial Sequence
<220> FEATURE:
<223> OTHER INFORMATION: the humanized heavy chain mutant H3B10-M1

<400> SEQUENCE: 24

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Ser Tyr
            20                  25                  30

Asp Ile Ser Trp Ile Arg Gln Pro Pro Gly Lys Ala Leu Glu Trp Leu
        35                  40                  45

Gly Val Ile Trp Ser Glu Gly Gly Thr Ser Tyr Ser Thr Ser Leu Lys
    50                  55                  60

Ser Arg Leu Thr Ile Ser Lys Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Asp Ser Asp Asp Gly Tyr Leu Asn Trp Gly Gln Gly Thr Leu Val
            100                 105                 110

Thr Val Ser Ser
        115


<210> SEQ ID NO 25
<211> LENGTH: 108
<212> TYPE: PRT
<213> ORGANISM: Artificial Sequence
<220> FEATURE:
<223> OTHER INFORMATION: L3E8-M2

<400> SEQUENCE: 25

Glu Ile Val Met Thr Gln Ser Pro Ala Thr Leu Ser Val Ser Pro Gly
1               5                   10                  15

Glu Arg Ala Thr Leu Ser Cys Ser Val Ser Ser Ser Ile Ser Ser Ser
```

```
            20                  25                  30

Asn Leu His Trp Tyr Gln Gln Lys Pro Gly Gln Ala Pro Lys Pro Trp
        35                  40                  45

Ile Tyr Gly Thr Ser Asn Leu Ala Ser Gly Ile Pro Ala Arg Phe Ser
    50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Trp Ser Ser Tyr Pro
                85                  90                  95

Leu Thr Phe Gly Gln Gly Thr Lys Leu Glu Ile Lys
            100                 105


<210> SEQ ID NO 26
<211> LENGTH: 108
<212> TYPE: PRT
<213> ORGANISM: Artificial Sequence
<220> FEATURE:
<223> OTHER INFORMATION: L3E8-M3

<400> SEQUENCE: 26

Glu Ile Val Met Thr Gln Ser Pro Ala Thr Leu Ser Val Ser Pro Gly
1               5                   10                  15

Glu Arg Ala Thr Ile Thr Cys Ser Val Ser Ser Ser Ile Ser Ser Ser
            20                  25                  30

Asn Leu His Trp Tyr Gln Gln Lys Pro Gly Gln Ala Pro Arg Pro Trp
        35                  40                  45

Ile Tyr Gly Thr Ser Asn Leu Ala Ser Gly Ile Pro Ala Arg Phe Ser
    50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Trp Ser Ser Tyr Pro
                85                  90                  95

Leu Thr Phe Gly Gln Gly Thr Lys Leu Glu Ile Lys
            100                 105


<210> SEQ ID NO 27
<211> LENGTH: 108
<212> TYPE: PRT
<213> ORGANISM: Artificial Sequence
<220> FEATURE:
<223> OTHER INFORMATION: L3E8-M4

<400> SEQUENCE: 27

Glu Ile Val Met Thr Gln Ser Pro Ala Thr Leu Ser Val Ser Pro Gly
1               5                   10                  15

Glu Arg Ala Thr Leu Ser Cys Ser Val Ser Ser Ser Ile Ser Ser Ser
            20                  25                  30

Asn Leu His Trp Tyr Gln Gln Lys Pro Gly Gln Ala Pro Arg Pro Trp
        35                  40                  45

Ile Tyr Gly Thr Ser Asn Leu Ala Ser Gly Ile Pro Ala Arg Phe Ser
    50                  55                  60

Gly Ser Gly Ser Gly Thr Glu Phe Thr Leu Thr Ile Ser Ser Met Glu
65                  70                  75                  80

Ala Glu Asp Phe Ala Val Tyr Tyr Cys Gln Gln Trp Ser Ser Tyr Pro
                85                  90                  95

Leu Thr Phe Gly Gln Gly Thr Lys Leu Glu Ile Lys
            100                 105
```

```
<210> SEQ ID NO 28
<211> LENGTH: 108
<212> TYPE: PRT
<213> ORGANISM: Artificial Sequence
<220> FEATURE:
<223> OTHER INFORMATION: the mutant L3E8-M7

<400> SEQUENCE: 28

Glu Ile Val Met Thr Gln Ser Pro Ala Thr Leu Ser Val Ser Pro Gly
1               5                   10                  15

Glu Arg Ala Thr Leu Ser Cys Ser Val Ser Ser Ser Ile Ser Ser Ser
            20                  25                  30

Asn Leu His Trp Tyr Gln Gln Lys Pro Gly Gln Ala Pro Arg Pro Trp
        35                  40                  45

Ile Tyr Gly Thr Ser Asn Leu Ala Ser Gly Ile Pro Ala Arg Phe Ser
    50                  55                  60

Gly Ser Gly Ser Gly Thr Glu Phe Thr Leu Thr Ile Ser Ser Val Gln
65                  70                  75                  80

Ala Glu Asp Phe Ala Val Tyr Tyr Cys Gln Gln Trp Ser Ser Tyr Pro
                85                  90                  95

Leu Thr Phe Gly Gln Gly Thr Lys Leu Glu Ile Lys
            100                 105


<210> SEQ ID NO 29
<211> LENGTH: 5
<212> TYPE: PRT
<213> ORGANISM: Artificial Sequence
<220> FEATURE:
<223> OTHER INFORMATION: HCDR1 of the humanized heavy chain mutant
      H3B10-M1

<400> SEQUENCE: 29

Ser Tyr Asp Ile Ser
1               5


<210> SEQ ID NO 30
<211> LENGTH: 16
<212> TYPE: PRT
<213> ORGANISM: Artificial Sequence
<220> FEATURE:
<223> OTHER INFORMATION: HCDR2 of the humanized heavy chain mutant
      H3B10-M1

<400> SEQUENCE: 30

Val Ile Trp Ser Glu Gly Gly Thr Ser Tyr Ser Thr Ser Leu Lys Ser
1               5                   10                  15


<210> SEQ ID NO 31
<211> LENGTH: 8
<212> TYPE: PRT
<213> ORGANISM: Artificial Sequence
<220> FEATURE:
<223> OTHER INFORMATION: HCDR3 of the humanized heavy chain mutant
      H3B10-M1

<400> SEQUENCE: 31

Asp Ser Asp Asp Gly Tyr Leu Asn
1               5


<210> SEQ ID NO 32
<211> LENGTH: 12
<212> TYPE: PRT
<213> ORGANISM: Artificial Sequence
<220> FEATURE:
```

<223> OTHER INFORMATION: LCDR1 of the light chain variable region L3E8-M1

<400> SEQUENCE: 32

Ser Val Ser Ser Ser Ile Ser Ser Ser Asn Leu His
1 5 10

<210> SEQ ID NO 33
<211> LENGTH: 7
<212> TYPE: PRT
<213> ORGANISM: Artificial Sequence
<220> FEATURE:
<223> OTHER INFORMATION: LCDR2 of the light chain variable region L3E8-M1

<400> SEQUENCE: 33

Gly Thr Ser Asn Leu Ala Ser
1 5

<210> SEQ ID NO 34
<211> LENGTH: 9
<212> TYPE: PRT
<213> ORGANISM: Artificial Sequence
<220> FEATURE:
<223> OTHER INFORMATION: LCDR3 of the light chain variable region L3E8-M1

<400> SEQUENCE: 34

Gln Gln Trp Ser Ser Tyr Pro Leu Thr
1 5

<210> SEQ ID NO 35
<211> LENGTH: 5
<212> TYPE: PRT
<213> ORGANISM: Artificial Sequence
<220> FEATURE:
<223> OTHER INFORMATION: HCDR1 of the heavy chain variable region of the humanized antibody H1A10+L3E8-M1

<400> SEQUENCE: 35

Asn Tyr Trp Met Asn
1 5

<210> SEQ ID NO 36
<211> LENGTH: 17
<212> TYPE: PRT
<213> ORGANISM: Artificial Sequence
<220> FEATURE:
<223> OTHER INFORMATION: HCDR2 of the heavy chain variable region of the humanized antibody H1A10+L3E8-M1

<400> SEQUENCE: 36

Gln Ile Phe Pro Gly Asp Ser Asp Thr Asp Tyr Asp Gln Lys Phe Gln
1 5 10 15

Gly

<210> SEQ ID NO 37
<211> LENGTH: 12
<212> TYPE: PRT
<213> ORGANISM: Artificial Sequence
<220> FEATURE:
<223> OTHER INFORMATION: HCDR3 of the heavy chain variable region of the humanized antibody H1A10+L3E8-M1

<400> SEQUENCE: 37

Ala Gly Tyr Tyr Arg Gly Tyr Tyr Ala Met Asp Tyr
1 5 10

<210> SEQ ID NO 38
<211> LENGTH: 446
<212> TYPE: PRT
<213> ORGANISM: Artificial Sequence
<220> FEATURE:
<223> OTHER INFORMATION: H3B10-M1-IgG1m3-H

<400> SEQUENCE: 38

Gln Val Thr Leu Lys Glu Ser Gly Pro Val Leu Val Lys Pro Thr Glu
1 5 10 15

Thr Leu Thr Leu Thr Cys Thr Val Ser Gly Phe Ser Leu Ser Ser Tyr
20 25 30

Asp Ile Ser Trp Ile Arg Gln Pro Pro Gly Lys Ala Leu Glu Trp Leu
35 40 45

Gly Val Ile Trp Ser Glu Gly Gly Thr Ser Tyr Ser Thr Ser Leu Lys
50 55 60

Ser Arg Leu Thr Ile Ser Lys Asp Thr Ser Lys Ser Gln Val Val Leu
65 70 75 80

Thr Met Thr Asn Met Asp Pro Val Asp Thr Ala Thr Tyr Tyr Cys Ala
85 90 95

Arg Asp Ser Asp Asp Gly Tyr Leu Asn Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Glu Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asp His Lys Pro Ser Asn Thr
195 200 205

Lys Val Asp Lys Thr Val Glu Pro Lys Ser Cys Asp Lys Thr His Thr
210 215 220

Cys Pro Pro Cys Pro Ala Pro Glu Phe Glu Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser Gln Glu Asp Pro Glu Val
260 265 270

Gln Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Ser Ile Glu Lys Thr Ile Ser
325 330 335

Lys Ala Lys Gly Gln Pro Arg Glu Pro Gln Val Cys Thr Leu Pro Pro
340 345 350

Ser Gln Glu Glu Met Thr Lys Asn Gln Val Ser Leu Ser Cys Ala Val
355 360 365

```
Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 39
<211> LENGTH: 215
<212> TYPE: PRT
<213> ORGANISM: Artificial Sequence
<220> FEATURE:
<223> OTHER INFORMATION: the light chain comprising the L3E8-M1 light
      chain variable region

<400> SEQUENCE: 39

Glu Ile Val Met Thr Gln Ser Pro Ala Thr Leu Ser Val Ser Pro Gly
1               5                   10                  15

Glu Arg Ala Thr Leu Ser Cys Ser Val Ser Ser Ser Ile Ser Ser Ser
            20                  25                  30

Asn Leu His Trp Tyr Gln Gln Lys Pro Gly Gln Ala Pro Arg Pro Trp
        35                  40                  45

Ile Tyr Gly Thr Ser Asn Leu Ala Ser Gly Ile Pro Ala Arg Phe Ser
    50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Trp Ser Ser Tyr Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 40
<211> LENGTH: 215
<212> TYPE: PRT
<213> ORGANISM: Artificial Sequence
<220> FEATURE:
<223> OTHER INFORMATION: the light chain comprising the L3E8-M7 light
      chain variable region

<400> SEQUENCE: 40
```

```
Glu Ile Val Met Thr Gln Ser Pro Ala Thr Leu Ser Val Ser Pro Gly
1               5                   10                  15

Glu Arg Ala Thr Leu Ser Cys Ser Val Ser Ser Ser Ile Ser Ser Ser
            20                  25                  30

Asn Leu His Trp Tyr Gln Gln Lys Pro Gly Gln Ala Pro Arg Pro Trp
        35                  40                  45

Ile Tyr Gly Thr Ser Asn Leu Ala Ser Gly Ile Pro Ala Arg Phe Ser
    50                  55                  60

Gly Ser Gly Ser Gly Thr Glu Phe Thr Leu Thr Ile Ser Ser Val Gln
65                  70                  75                  80

Ala Glu Asp Phe Ala Val Tyr Tyr Cys Gln Gln Trp Ser Ser Tyr Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 41
<211> LENGTH: 451
<212> TYPE: PRT
<213> ORGANISM: Artificial Sequence
<220> FEATURE:
<223> OTHER INFORMATION: H1A10-IgG1m3-K

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ser Asn Tyr
            20                  25                  30

Trp Met Asn Trp Val Arg Gln Ala Pro Gly Gln Gly Leu Glu Trp Met
        35                  40                  45

Gly Gln Ile Phe Pro Gly Asp Ser Asp Thr Asp Tyr Asp Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Gly Tyr Tyr Arg Gly Tyr Tyr Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140
```

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Arg Val Glu Pro Lys Ser Cys
210 215 220

Asp Lys Thr His Thr Cys Pro Pro Cys Pro Ala Pro Glu Phe Glu Gly
225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

Glu Asp Pro Glu Val Lys Phe Asn Trp Tyr Val Asp Gly Val Glu Val
275 280 285

His Asn Ala Lys Thr Lys Pro Arg Glu Glu Gln Tyr Asn Ser Thr Tyr
290 295 300

Arg Val Val Ser Val Leu Thr Val Leu His Gln Asp Trp Leu Asn Gly
305 310 315 320

Lys Glu Tyr Lys Cys Lys Val Ser Asn Lys Ala Leu Pro Ala Ser Ile
325 330 335

Glu Lys Thr Ile Ser Lys Ala Lys Gly Gln Pro Arg Glu Pro Gln Val
340 345 350

Tyr Thr Leu Pro Pro Cys Arg Glu Glu Met Thr Lys Asn Gln Val Ser
355 360 365

Leu Trp Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Tyr Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly Lys
450

<210> SEQ ID NO 42
<211> LENGTH: 209
<212> TYPE: PRT
<213> ORGANISM: Homo sapiens

<400> SEQUENCE: 42

Gln Gly Gly Ala Ala Glu Gly Val Gln Ile Gln Ile Ile Tyr Phe Asn
1 5 10 15

Leu Glu Thr Val Gln Val Thr Trp Asn Ala Ser Lys Tyr Ser Arg Thr
20 25 30

Asn Leu Thr Phe His Tyr Arg Phe Asn Gly Asp Glu Ala Tyr Asp Gln
35 40 45

Cys Thr Asn Tyr Leu Leu Gln Glu Gly His Thr Ser Gly Cys Leu Leu

```
    50                  55                  60

Asp Ala Glu Gln Arg Asp Asp Ile Leu Tyr Phe Ser Ile Arg Asn Gly
65                  70                  75                  80

Thr His Pro Val Phe Thr Ala Ser Arg Trp Met Val Tyr Tyr Leu Lys
                85                  90                  95

Pro Ser Ser Pro Lys His Val Arg Phe Ser Trp His Gln Asp Ala Val
            100                 105                 110

Thr Val Thr Cys Ser Asp Leu Ser Tyr Gly Asp Leu Leu Tyr Glu Val
        115                 120                 125

Gln Tyr Arg Ser Pro Phe Asp Thr Glu Trp Gln Ser Lys Gln Glu Asn
    130                 135                 140

Thr Cys Asn Val Thr Ile Glu Gly Leu Asp Ala Glu Lys Cys Tyr Ser
145                 150                 155                 160

Phe Trp Val Arg Val Lys Ala Met Glu Asp Val Tyr Gly Pro Asp Thr
                165                 170                 175

Tyr Pro Ser Asp Trp Ser Glu Val Thr Cys Trp Gln Arg Gly Glu Ile
            180                 185                 190

Arg Asp Ala Cys Ala Glu Thr Pro Thr Pro Pro Lys Pro Lys Leu Ser
        195                 200                 205

Lys


<210> SEQ ID NO 43
<211> LENGTH: 219
<212> TYPE: PRT
<213> ORGANISM: Homo sapiens

<400> SEQUENCE: 43

Glu Ser Gly Tyr Ala Gln Asn Gly Asp Leu Glu Asp Ala Glu Leu Asp
1               5                   10                  15

Asp Tyr Ser Phe Ser Cys Tyr Ser Gln Leu Glu Val Asn Gly Ser Gln
            20                  25                  30

His Ser Leu Thr Cys Ala Phe Glu Asp Pro Asp Val Asn Thr Thr Asn
        35                  40                  45

Leu Glu Phe Glu Ile Cys Gly Ala Leu Val Glu Val Lys Cys Leu Asn
    50                  55                  60

Phe Arg Lys Leu Gln Glu Ile Tyr Phe Ile Glu Thr Lys Lys Phe Leu
65                  70                  75                  80

Leu Ile Gly Lys Ser Asn Ile Cys Val Lys Val Gly Glu Lys Ser Leu
                85                  90                  95

Thr Cys Lys Lys Ile Asp Leu Thr Thr Ile Val Lys Pro Glu Ala Pro
            100                 105                 110

Phe Asp Leu Ser Val Ile Tyr Arg Glu Gly Ala Asn Asp Phe Val Val
        115                 120                 125

Thr Phe Asn Thr Ser His Leu Gln Lys Lys Tyr Val Lys Val Leu Met
    130                 135                 140

His Asp Val Ala Tyr Arg Gln Glu Lys Asp Glu Asn Lys Trp Thr His
145                 150                 155                 160

Val Asn Leu Ser Ser Thr Lys Leu Thr Leu Leu Gln Arg Lys Leu Gln
                165                 170                 175

Pro Ala Ala Met Tyr Glu Ile Lys Val Arg Ser Ile Pro Asp His Tyr
            180                 185                 190
```

-continued

```
Phe Lys Gly Phe Trp Ser Glu Trp Ser Pro Ser Tyr Tyr Phe Arg Thr
        195                 200                 205

Pro Glu Ile Asn Asn Ser Ser Gly Glu Met Asp
    210                 215
```

ANTIBODIES AGAINST HUMAN TSLP AND USE THEREOF

CROSS REFERENCE TO RELATED APPLICATIONS

This application is a 35 U.S.C. § 371 National Phase Entry Application of International Application No. PCT/CN2021/100657 filed Jun. 17, 2021, which designates the U.S. and claims benefit under 35 U.S.C. § 119(a) of Chinese Patent Application No. 202110147687.1 filed on Feb. 3, 2021, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Aug. 1, 2023, is named 078291-000309US-PX_SL.txt and is 57,815 bytes in size.

TECHNICAL FIELD

The present application generally relates to the field of genetic engineering and antibody medicine. In particular, the present application relates to a bispecific antibody and a monoclonal antibody against human TSLP, and uses thereof.

BACKGROUND

Human thymic stromal lymphopoietin (TSLP), also known as IL-7-like cytokine[1], is a member of IL-2 cytokine family. TSLP is secreted predominantly by epithelial cells of thymus, lung, intestine and skin[2, 3], and to a lesser extent by some fibroblasts, airway smooth muscle endothelial cells, mast cells, monocytes, granulocytes and dendritic cells (DC)[4-14]. The expression of TSLP is regulated by some factors, such as allergens, proinflammatory factors (IL-1β, TNF-α, TGF-β, IL-4, and IL-13), Th2 cytokine, trauma, mechanical injury and bacteria, etc[15-18].

The target cells of TSLP co-express TSLP receptor (thymic stromal lymphopoietin receptor, TSLPR) and IL-7 receptor α chain (IL-7Rα)[19]. TSLPR binds to TSLP with high affinity, thereby allosterically activating TSLP, which in turn recruits IL-7Rα to form TSLP-TSLPR-IL-7Rα ternary complex that can transmit signals. IL-7Rα binds to TSLP-TSLPR with high affinity, but binds to TSLP very weakly[20].

Asthma is a chronic disease characterized by inflammation of the airways, and is clinically characterized by recurrent symptoms such as wheezing, shortness of breath, chest tightness and coughing[21]. Globally, about 300 million people suffer from asthma[22]. The global prevalence of asthma has been increasing at a rate of about 1% every year for the past two decades. The existing therapeutic drugs, including bronchodilators, glucocorticoids, combined preparations of bronchodilators and glucocorticoids (such as seretide and symbicort), leukotriene modulators, long-acting cholinergic receptor antagonists (such as tiotropium bromide), and IgE antibodies, cannot control the condition of all asthmatics.

Numerous studies have demonstrated that about ⅔ of severe asthma is characterized by overexpression of Th2 cytokines, and TSLP is an important factor causing overexpression of Th2 cytokines. The TSLP-TSLPR effect is mainly mediated through JAK-STAT signaling pathway[2].

Research suggests that upregulated TSLP will bind to TSLPR on DC cells so as to activate JAK, recruit transcription factor STAT5, and cause downstream signaling, and ultimately leading to DC cell activation. DC cell activation exhibits upregulated expression of co-stimulatory molecules (such as CD80, CD40 and CD86) and secretion of chemokines (such as TARC/CCL17, MDC/CCL22 and I-309/CCL1), which provides a favorable microenvironment for the differentiation of Th0 to Th2 cells to direct Th2 cell-predominant inflammatory response accompanied by release of factors (IL-4, IL-13 and IL-5)[11, 12, 23, 24]. TSLP transgenic mice are susceptible to specific antigens and thus develop asthma, whereas symptoms are significantly reduced in TSLP receptor knockout mice[24]. Analysing the mechanisms of asthma and inflammation, anti-cytokine (IL-4, IL-13, IL-5) drugs only target specific inflammatory molecules that drive asthma and inflammation, and are only suitable for certain types of severe asthma patients, i.e., subgroup patients, such as eosinophilic asthma. TSLP is significantly different from targets such as IL-4 and IL-5. TSLP is active in the early upstream of inflammatory cascade, and may be suitable for a wide range of patients with severe uncontrolled asthma.

Researchers have conducted extensive exploration and research on drugs targeting TSLP. Anti-TSLP monoclonal antibodies can effectively block TSLP/TSLPR action, reverse airway inflammation, prevent tissue structural changes, and reduce airway hyperresponsiveness (AHR) and TGF-β1 level in a mite dust-induced mouse model of asthma[25]. In a serum protein-induced mouse model of asthma, anti-TSLP monoclonal antibodies effectively reduce the expression of Th2 factors (such as IL-4 and IL-5)[26]. The safety of anti-TSLP monoclonal antibodies has also been well established in monkeys. Moreover, the only clinically investigated anti-TSLP monoclonal antibody around the world shows a good objective response rate in the early clinical phase, effectively alleviating the symptoms of the subjects[27].

Bispecific antibody (BsAb) is a class of artificial antibody which comprises two different antigen binding sites, can build a bridge between target cells and functional molecules (cells) and stimulate a directed immune response. It has now become a research hotspot in the field of antibody engineering and has a broad application prospect in the immunotherapy of diseases.

The development and application of new anti-TSLP antibodies are needed in this field. Therefore, in view of the wide applicability of anti-TSLP antibodies and due to clinical needs, it is of great biological and medical significance to explore and develop new anti-TSLP antibodies.

SUMMARY OF THE INVENTION

In a first aspect, there is provided in the present application a bispecific antibody comprising a first binding fragment and a second binding fragment that bind to non-overlapping epitopes of human thymic stromal lymphopoietin (TSLP).

In some embodiments of the first aspect, the bispecific antibody is capable of blocking the binding of human TSLP to human TSLP receptor (TSLPR), and the bispecific antibody is capable of blocking the binding of human IL-7 receptor alpha chain (IL-7Rα) to human TSLP: TSLPR complex.

In some embodiments of the first aspect, the epitope of human TSLP bound by one of the first binding fragment and the second binding fragment partially overlaps with the epitope of human TSLP bound by IL-7Rα.

In some embodiments of the first aspect, the first binding fragment comprises HCDR1 as set forth in SEQ ID NO:29, HCDR2 as set forth in SEQ ID NO:30, HCDR3 as set forth in SEQ ID NO:31, LCDR1 as set forth in SEQ ID NO:32, LCDR2 as set forth in SEQ ID NO:33, and LCDR3 as set forth in SEQ ID NO:34; wherein the amino acid sequences of HCDRs and LCDRs are defined according to Kabat.

In some embodiments of the first aspect, the second binding fragment comprises HCDR1 as set forth in SEQ ID NO:35, HCDR2 as set forth in SEQ ID NO:36, HCDR3 as set forth in SEQ ID NO:37, LCDR1 as set forth in SEQ ID NO:32, LCDR2 as set forth in SEQ ID NO:33, and LCDR3 as set forth in SEQ ID NO:34; wherein the amino acid sequences of HCDRs and LCDRs are defined according to Kabat.

In some embodiments of the first aspect, the amino acid sequence of the heavy chain variable region of the first binding fragment is set forth in SEQ ID NO: 24, and the amino acid sequence of the light chain variable region of the first binding fragment is set forth in SEQ ID NO: 21; or the amino acid sequence of the heavy chain variable region of the first binding fragment is set forth in SEQ ID NO: 24, and the amino acid sequence of the light chain variable region of the first binding fragment is set forth in SEQ ID NO: 28.

In some embodiments of the first aspect, the amino acid sequence of the heavy chain variable region of the second binding fragment is set forth in SEQ ID NO: 20, and the amino acid sequence of the light chain variable region of the second binding fragment is set forth in SEQ ID NO: 21; or the amino acid sequence of the heavy chain variable region of the second binding fragment is set forth in SEQ ID NO: 20, and the amino acid sequence of the light chain variable region of the second binding fragment is set forth in SEQ ID NO: 28.

In some embodiments of the first aspect, the bispecific antibody is an IgG1 antibody comprising a first heavy chain constant region and a second heavy chain constant region, wherein the amino acids at positions 354 and 366 of the first heavy chain constant region are C and W, respectively, and the amino acids at positions 349, 366, 368 and 407 of the second heavy chain constant region are C, S, A and V, respectively; and the amino acid positions of antibody constant regions are determined according to EU numbering.

In some embodiments of the first aspect, the bispecific antibody is an IgG1 antibody comprising a first heavy chain constant region and a second heavy chain constant region, wherein the amino acids at positions 234, 235 and 331 of the first heavy chain constant region and the second heavy chain constant region are F, E and S, respectively; and the amino acid positions of antibody constant regions are determined according to EU numbering.

In some embodiments of the first aspect, the forms of the first binding fragment and the second binding fragment are independently selected from a single-chain fragment variable (scFv) or a Fab fragment.

In some embodiments of the first aspect, the first binding fragment and the second binding fragment have the same light chain variable region.

In some embodiments of the first aspect, the bispecific antibody comprises the heavy chain as set forth in SEQ ID NO:38 and the light chain as set forth in one of SEQ ID NOs: 39 and 40.

In some embodiments of the first aspect, the bispecific antibody comprises the heavy chain as set forth in SEQ ID NO:41 and the light chain as set forth in one of SEQ ID NOs: 39 and 40.

In a second aspect, there is provided in the present application a monoclonal antibody that binds to human TSLP, comprising HCDR1 as set forth in SEQ ID NO:29, HCDR2 as set forth in SEQ ID NO:30, HCDR3 as set forth in SEQ ID NO:31, LCDR1 as set forth in SEQ ID NO:32, LCDR2 as set forth in SEQ ID NO:33, and LCDR3 as set forth in SEQ ID NO:34; wherein the amino acid sequences of HCDRs and LCDRs are defined according to Kabat.

In a third aspect, there is provided in the present application a pharmaceutical composition comprising the bispecific antibody of the first aspect, or the monoclonal antibody of the second aspect, and a pharmaceutically acceptable excipient, diluent, or carrier.

In a fourth aspect, there is provided in the present application use of the bispecific antibody of the first aspect, the monoclonal antibody of the second aspect, or the pharmaceutical composition of the third aspect in the manufacture of a medicament for the prevention or treatment of TSLP-mediated diseases.

DESCRIPTION OF THE SEQUENCES

Figure 1:
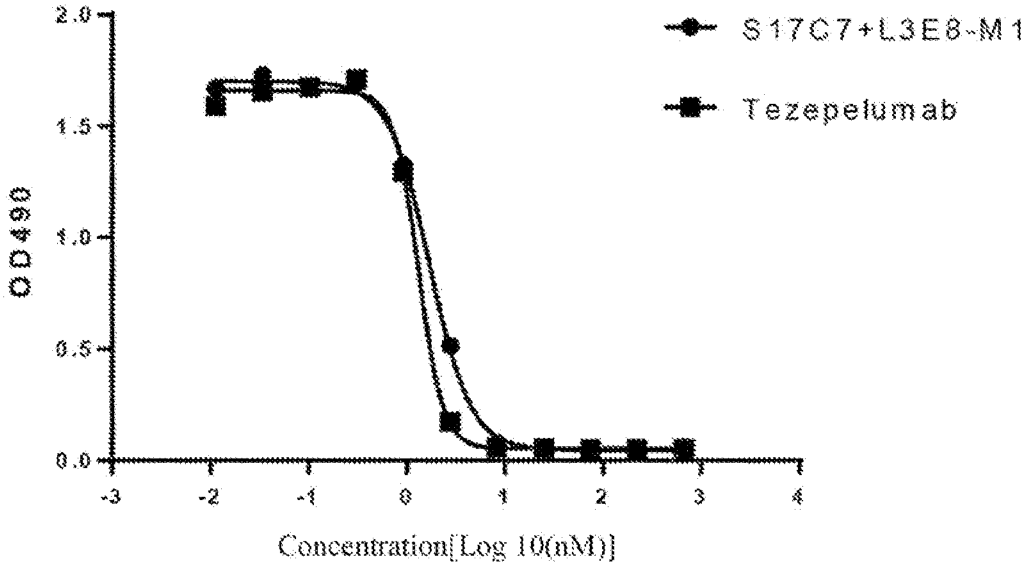
FIG. 1 shows the results from an ELISA assay assessing the inhibitory effect of the anti-human TSLP monoclonal antibody S17C7+L3E8-M1 on the binding of TSLP to TSLPR.

SEQ ID NO: 1 shows the amino acid sequence of the long version of the extracellular domain of human (*Homo sapiens*) TSLP (hTSLP1-ECD).

SEQ ID NO: 2 shows the amino acid sequence of the short version of the extracellular domain of human (*Homo sapiens*) TSLP (hTSLP2-ECD).

SEQ ID NO: 3 shows the amino acid sequence of the extracellular domain of mouse (*Mus musculus*) TSLP (mTSLP-ECD).

SEQ ID NO: 4 shows the amino acid sequence of the extracellular domain of cynomolgus monkey (*Macaca fascicularis*) TSLP (mfTSLP1-ECD).

SEQ ID NO: 5 shows the amino acid sequence of hTSLP1 mutant (hTSLP1-m) with the deletion of furin recognition site.

SEQ ID NO: 6 shows the amino acid sequences of hTSLP2 mutant (hTSLP2-m) with the deletion of furin recognition site.

SEQ ID NO: 7 shows the amino acid sequence of mfTSLP mutant (mfTSLP1-m) with the deletion of furin recognition site.

SEQ ID NO: 8 shows the amino acid sequence of His tag.

SEQ ID NO:9 shows the amino acid sequence of the Fc fragment (hFc) of human (*Homo sapiens*) IgG1 antibody.

SEQ ID NO:10 shows the amino acid sequence of the Fc fragment (mFc) of mouse (*Mus musculus*) IgG2a antibody.

SEQ ID NO:11 shows the amino acid sequence of the heavy chain constant region of human (*Homo sapiens*) IgG1 subtype.

SEQ ID NO:12 shows the amino acid sequence of the heavy chain constant region of human (*Homo sapiens*) IgG2 subtype.

SEQ ID NO:13 shows the amino acid sequence of the heavy chain constant region of human (*Homo sapiens*) IgG4 subtype.

SEQ ID NO:14 shows the amino acid sequence of the heavy chain constant region of mouse (*Mus musculus*) IgG1 subtype.

SEQ ID NO:15 shows the amino acid sequence of the heavy chain constant region of mouse (*Mus musculus*) IgG2a subtype.

SEQ ID NO:16 shows the amino acid sequence of the light chain constant region of human (*Homo sapiens*) kappa subtype.

SEQ ID NO:17 shows the amino acid sequence of the light chain constant region of human (*Homo sapiens*) lamda subtype.

SEQ ID NO:18 shows the amino acid sequence of the light chain constant region of mouse (*Mus musculus*) kappa subtype.

SEQ ID NO:19 shows the amino acid sequence of the light chain constant region of mouse (*Mus musculus*) lamda subtype.

SEQ ID NO:20 shows the amino acid sequence of the heavy chain variable region of the humanized antibody H1A10+L3E8-M1 with the amino acid sequences of HCDR1-HCDR3 as set forth in SEQ ID NO:35, SEQ ID NO:36 and SEQ ID NO:37, respectively.

SEQ ID NO:21 shows the amino acid sequence of the light chain variable region L3E8-M1 of the humanized antibody H1A10+L3E8-M1 with the amino acid sequences of LCDR1-LCDR3 as set forth in SEQ ID NO:32, SEQ ID NO:33 and SEQ ID NO:34, respectively.

SEQ ID NO:22 shows the amino acid sequence of the heavy chain variable region of the anti-human TSLP control antibody Tezepelumab.

SEQ ID NO:23 shows the amino acid sequence of the light chain variable region of the anti-human TSLP control antibody Tezepelumab.

SEQ ID NO:24 shows the amino acid sequence of the humanized heavy chain mutant H3B10-M1 with the amino acid sequences of HCDR1-HCDR3 as set forth in SEQ ID NO:29, SEQ ID NO:30 and SEQ ID NO:31, respectively.

SEQ ID NO:25 shows the amino acid sequence of L3E8-M2.

SEQ ID NO:26 shows the amino acid sequence of L3E8-M3.

SEQ ID NO:27 shows the amino acid sequence of L3E8-M4.

SEQ ID NO:28 shows the amino acid sequence of the mutant L3E8-M7 with the amino acid sequences of LCDR1-LCDR3 as set forth in SEQ ID NO:32, SEQ ID NO:33 and SEQ ID NO:34, respectively.

SEQ ID NO:38 shows the amino acid sequence of H3B10-M1-IgG1m3-H.

SEQ ID NO:39 shows the amino acid sequence of the light chain comprising the L3E8-M1 light chain variable region.

SEQ ID NO:40 shows the amino acid sequence of the light chain comprising the L3E8-M7 light chain variable region.

SEQ ID NO:41 shows the amino acid sequence of H1A10-IgG1m3-K.

SEQ ID NO:42 shows the amino acid sequence of the extracellular domain (hTSLPR-ECD) of human (*Homo sapiens*) TSLP receptor.

SEQ ID NO:43 shows the amino acid sequence of the extracellular domain (hIL-7Rα-ECD) of human (*Homo sapiens*) IL-7 receptor alpha chain.

DETAILED DESCRIPTION OF THE INVENTION

The present inventors have conducted extensive research and development of antibody drugs that bind to human TSLP, and have obtained novel bispecific antibodies and monoclonal antibodies that bind to human TSLP by antibody engineering techniques. In various aspects of the present application, there are provided novel bispecific and monoclonal antibodies that bind to human TSLP, polynucleotides encoding the bispecific or monoclonal antibodies, vectors comprising the polynucleotides, host cells comprising the polynucleotides or vectors, methods of preparing and purifying the bispecific or monoclonal antibodies, and medical and biological use of the bispecific or monoclonal antibodies. Based on the sequences of the variable regions of the bispecific or monoclonal antibodies provided herein, full-length bispecific or monoclonal antibody molecules can be constructed for use in the clinic as drugs for preventing or treating TSLP mediated diseases.

Unless otherwise indicated, the inventions of the present application can be implemented using conventional molecular biology, microbiology, cell biology, biochemistry, and immunological techniques in the art.

Unless otherwise indicated, the terms used in the present application have the meanings commonly understood by those skilled in the art.

Definitions

As used herein, the term "antibody" refers to an immunoglobulin molecule that is capable of specifically binding to a target via at least one antigen recognition site located in a variable region of the immunoglobulin molecule. Targets include, but are not limited to, carbohydrates, polynucleotides, lipids, and polypeptides, etc. As used herein, an "antibody" includes not only an intact (i.e., full-length) antibody, but also a binding fragment thereof (e.g., Fab, Fab', $F(ab')_2$, Fv), a variant thereof, a fusion protein comprising portions of an antibody, a humanized antibody, a chimeric antibody, a diabody, a linear antibody, a single-chain fragment variable, a VHH antibody, a multi-specific antibody (e.g., a bispecific antibody), and any other modified configurations of an immunoglobulin molecule comprising a desired specific antigen recognition site, including a glycosylated variant of an antibody, an amino acid sequence variant of an antibody, and a covalently modified antibody.

Typically, an intact or full-length antibody comprises two heavy chains and two light chains. Each heavy chain contains a heavy chain variable region (VH) and first, second and third constant regions (CH1, CH2 and CH3). Each light chain contains a light chain variable region (VL) and a constant region (CL). A full-length antibody may be of any type of antibody, such as an IgD, IgE, IgG, IgA, or IgM (or their subtypes) antibody, but not necessarily belongs to any particular type. Immunoglobulins can be assigned to different types depending on their amino acid sequences of the heavy chain constant regions. Generally, immunoglobulins have five main types, i.e., IgA, IgD, IgE, IgG, and IgM, and some of these types can be further classified into subtypes (isotypes), such as IgG1, IgG2, IgG3, IgG4, IgA1, and IgA2. Heavy chain constant regions corresponding to individual immunoglobulin types are referred to as $\alpha$, $\delta$, $\varepsilon$, $\gamma$, and $\mu$, respectively. Subunit structures and three-dimensional structures of different types of immunoglobulins are well known.

As used herein, the term "bispecific antibody" refers to an antibody that can simultaneously bind to two antigen epitopes. The two antigen epitopes may be on different antigens or on the same antigen. A bispecific antibody can have a variety of structural configurations. For example, a bispecific antibody may consist of two Fc fragments and two binding portions fused thereto, respectively (similar to a natural antibody, except that the two arms bind to different antigen targets or epitopes). Antigen-binding portions can be a single-chain fragment variable (scFv) or Fab fragments. When two non-overlapping epitopes of the same antigen are given, two different binding portions of a bispecific antibody each binds to the N-terminus of one Fc fragment. The configuration of the antigen-binding portions of the two arms can have four combinations, i.e., scFv+Fab fragment, Fab fragment+scFv, scFv+scFv, and Fab fragment+Fab fragment. Fc fragments can contain mutations that can ensure heavy chain heteromerization. The KIH (knob-in-hole) technique is one strategy to address heavy chain heteromerization. Generally, the KIH technique refers to formation of a structure that facilitates the pairing of heterogeneous hemibodies by engineering the amino acid sequence of a CH3 region. This can maintain the structure of a normal antibody as much as possible while forming a bispecific antibody. For guidance of the KIH technique, see, for example, "An efficient route to human bispecific IgG", A. Margaret Merchant et al., Nature Biotechnology, Volume 16, 1998, which is incorporated herein by reference in its entirety. Furthermore, a bispecific antibody can be configured in a way that an antibody that binds to a first epitope of an antigen (e.g., in the form of a natural antibody) has an antigen-binding portion that can bind to a second epitope of the antigen extending from the C-terminus of the CH3 region (e.g., via a flexible linker).

As used herein, the term "binding portion" or "binding fragment" can be used interchangeably, and refers to a portion or region of an intact antibody molecule responsible for binding to an antigen. An antigen binding domain can comprise a heavy chain variable region (VH), a light chain variable region (VL), or both. Each of VH and VL typically contains three complementarity determining regions, i.e., CDR1, CDR2, and CDR3.

It is well known to those skilled in the art that complementarity determining regions (CDRs, usually including CDR1, CDR2 and CDR3) are the regions of a variable region that have mostly impact on the affinity and specificity of an antibody. The CDR sequences of VH or VL have two common definitions, i.e., the Kabat definition and the Chothia definition (see, e.g., Kabat, "Sequences of Proteins of Immunological Interest", National Institutes of Health, Bethesda, Md. (1991); Al-Lazikani et al., J. Mol. Biol. 273: 927-948 (1997); and Martin et al., Proc. Natl. Acad. Sci. USA 86: 9268-9272 (1989)). For the variable region sequences of a given antibody, the sequences of CDR regions in VH and VL can be determined according to the Kabat definition or the Chothia definition. In an embodiment of the present application, CDR sequences are defined according to Kabat.

For the variable region sequences of a given antibody, the sequences of CDR regions in the variable region sequences can be determined in a variety of ways, for example, using online software Abysis (abysis.org).

For conventional antibodies, examples of an antigen-binding fragment include, but are not limited to, (1) an Fab fragment, which can be a monovalent fragment having a VL-CL chain and a VH-CH1 chain; (2) an $F(ab')_2$ fragment, which can be a divalent fragment having two Fab' fragments linked by a disulfide bridge of the hinge region (i.e., a dimer of Fab'); (3) an Fv fragment having VL and VH domains in a single arm of an antibody; (4) a single-chain Fv (scFv), which can be a single polypeptide chain consisting of a VH domain and a VL domain via a polypeptide linker; (5) $(scFv)_2$, which can comprise two VH domains linked by a peptide linker and two VL domains that are combined with the two VH domains via a disulfide bridge; and (6) a VHH antibody.

In a bispecific antibody construct, a "binding portion" includes, but is not limited to, a Fab fragment or a single-chain fragment variable (scFv).

As used herein, the term "a single chain fragment variable (scFv)" refers to an antibody of a single chain structure generally constructed using genetic engineering techniques, comprising a polypeptide chain comprising a heavy chain variable region (VH) and a light chain variable region (VL). A flexible linker is typically designed between the heavy chain variable region and the light chain variable region so that the heavy chain variable region and the light chain variable region can be folded into the correct conformation for binding to an antigen.

As used herein, the term "Fab (fragment antigen-binding) fragment", "Fab portion", or the like refers to an antibody fragment that is produced after treatment of an intact antibody with papain and is capable of binding to an antigen, including the intact light chain (VL-CL), the heavy chain variable region, and the CH1 fragment (VH-CH1).

As used herein, the terms "first heavy chain constant region" and "second heavy chain constant region" both refer to "Fc fragment", "Fc domain" and "Fc portion" or similar terms, and refer to a part of the antibody heavy chain constant region, including hinge region, CH2 fragment and CH3 fragment of the heavy chain constant region, and are determined with reference to EU numbering of human IgG1 antibody.

As used herein, the term "monoclonal antibody" refers to an antibody from a substantially homogeneous antibody population, which means that the antibodies constituting the population are the same except for naturally occurring mutations which may occur in a small number of individual antibodies. Monoclonal antibodies described herein particularly include "chimeric" antibodies in which a portion of the heavy chain and/or the light chain is identical or homologous to a corresponding sequence in an antibody derived from a particular species or belonging to a particular antibody type or subtype, while the remaining portion of the heavy chain and/or the light chain is identical or homologous to a corresponding sequence in an antibody derived from another species or belonging to another antibody type or subtype; and also include fragments of such antibodies as long as they are capable of exhibiting the desired biological activity (see, U.S. Pat. No. 4,816,567; and Morrison et al., Proc. Natl. Acad. Sci. USA 81: 6851-6855 (1984)).

As used herein, the term "specific binding" refers to a non-random binding reaction between two molecules, e.g., binding of an antibody to an antigen epitope.

In a first aspect, there is provided in the present application a bispecific antibody comprising a first binding fragment and a second binding fragment that bind to non-overlpapping epitopes of human thymic stromal lymphopoietin (TSLP).

In some embodiments of the first aspect, the bispecific antibody is capable of blocking the binding of human TSLP to human TSLP receptor (TSLPR), and the bispecific antibody is capable of blocking the binding of human IL-7 receptor alpha chain (IL-7Rα) to human TSLP: TSLPR complex.

In some embodiments of the first aspect, the epitope of human TSLP bound by one of the first binding fragment and the second binding fragment partially overlaps with the epitope of human TSLP bound by IL-7Rα.

In some embodiments of the first aspect, the first binding fragment comprises HCDR1 as set forth in SEQ ID NO:29, HCDR2 as set forth in SEQ ID NO:30, HCDR3 as set forth in SEQ ID NO:31, LCDR1 as set forth in SEQ ID NO:32, LCDR2 as set forth in SEQ ID NO:33, and LCDR3 as set forth in SEQ ID NO:34; wherein the amino acid sequences of HCDRs and LCDRs are defined according to Kabat.

In some embodiments of the first aspect, the second binding fragment comprises HCDR1 as set forth in SEQ ID NO:35, HCDR2 as set forth in SEQ ID NO:36, HCDR3 as set forth in SEQ ID NO:37, LCDR1 as set forth in SEQ ID NO:32, LCDR2 as set forth in SEQ ID NO:33, and LCDR3 as set forth in SEQ ID NO:34; wherein the amino acid sequences of HCDRs and LCDRs are defined according to Kabat.

In some embodiments of the first aspect, the amino acid sequence of the heavy chain variable region of the first binding fragment is set forth in SEQ ID NO: 24, and the amino acid sequence of the light chain variable region of the first binding fragment is set forth in SEQ ID NO: 21; or the amino acid sequence of the heavy chain variable region of the first binding fragment is set forth in SEQ ID NO: 24, and the amino acid sequence of the light chain variable region of the first binding fragment is set forth in SEQ ID NO: 28.

In some embodiments of the first aspect, the amino acid sequence of the heavy chain variable region of the second binding fragment is set forth in SEQ ID NO: 20, and the amino acid sequence of the light chain variable region of the second binding fragment is set forth in SEQ ID NO: 21; or the amino acid sequence of the heavy chain variable region of the second binding fragment is set forth in SEQ ID NO: 20, and the amino acid sequence of the light chain variable region of the second binding fragment is set forth in SEQ ID NO: 28.

In some embodiments of the first aspect, the bispecific antibody is an IgG1 antibody comprising a first heavy chain constant region and a second heavy chain constant region, wherein the amino acids at positions 354 and 366 of the first heavy chain constant region are C and W, respectively, and the amino acids at positions 349, 366, 368 and 407 of the second heavy chain constant region are C, S, A and V, respectively; and the amino acid positions of antibody constant regions are determined according to EU numbering.

In some embodiments of the first aspect, the bispecific antibody is an IgG1 antibody comprising a first heavy chain constant region and a second heavy chain constant region, wherein the amino acids at positions 234, 235 and 331 of the first heavy chain constant region and the second heavy chain constant region are F, E and S, respectively; and the amino acid positions of antibody constant regions are determined according to EU numbering.

In some embodiments of the first aspect, the forms of the first binding fragment and the second binding fragment are independently selected from a single-chain fragment variable (scFv) or a Fab fragment.

In some embodiments of the first aspect, both of the first binding fragment and the second binding fragment are Fab fragments.

In some embodiments of the first aspect, the first binding fragment and the second binding fragment have the same light chain variable region.

In some embodiments of the first aspect, the first binding fragment and the second binding fragment have the same light chain.

In some embodiments of the first aspect, the bispecific antibody comprises the heavy chain as set forth in SEQ ID NO:38 and the light chain as set forth in one of SEQ ID NOs: 39 and 40.

In some embodiments of the first aspect, the bispecific antibody comprises the heavy chain as set forth in SEQ ID NO:41 and the light chain as set forth in one of SEQ ID NOs: 39 and 40.

In some embodiments of the first aspect, the amino acid sequence of the heavy chain variable region of the first binding fragment differs from the amino acid sequence as set forth in SEQ ID NO:24 by about 1, 2, 3, 4, 5, 6, 7, 8, 9, or 10 amino acid substitutions, deletions, and/or additions.

In some embodiments of the first aspect, the amino acid sequence of the light chain variable region of the first binding fragment differs from the amino acid sequence as set forth in SEQ ID NO:21 or 28 by about 1, 2, 3, 4, 5, 6, 7, 8, 9, or 10 amino acid substitutions, deletions, and/or additions.

In some embodiments of the first aspect, the amino acid sequence of the heavy chain variable region of the first binding fragment has at least 90%, 91%, 92%, 93%, 94%, 95%, 96%, 97%, 98%, 99% or more homology to SEQ ID NO:24.

In some embodiments of the first aspect, the amino acid sequence of the light chain variable region of the first binding fragment has at least 90%, 91%, 92%, 93%, 94%, 95%, 96%, 97%, 98%, 99% or more homology to SEQ ID NO:21 or 28.

In some embodiments of the first aspect, the C-terminal or N-terminal region of the amino acid sequence as set forth in SEQ ID NO:24 can also be truncated by about 1, 2, 3, 4, 5, 6, 7, 8, 9, 10, 11, 12, 13, 14, 15, 20, 25 or more amino acids while still retaining the function similar to that of the heavy chain variable region of the first binding fragment.

In some embodiments of the first aspect, 1, 2, 3, 4, 5, 6, 7, 8, 9, 10, 11, 12, 13, 14, 15, 20, 25 or more amino acids can also be added to the C-terminal or N-terminal region of the amino acid sequence as set forth in SEQ ID NO:24, and the resulting amino acid sequences still retain the function similar to that of the heavy chain variable region of the first binding fragment.

In some embodiments of the first aspect, 1, 2, 3, 4, 5, 6, 7, 8, 9, 10, 11, 12, 13, 14, 15, 20, 25 or more amino acids can also be added or deleted at a region other than the C-terminus or the N-terminus of the amino acid sequence as set forth in SEQ ID NO:24, provided that the altered amino acid sequences substantially retain the function similar to that of the heavy chain variable region of the first binding fragment.

In some embodiments of the first aspect, the C-terminal or N-terminal region of the amino acid sequence as set forth in SEQ ID NO:21 or 28 can also be truncated by about 1, 2, 3, 4, 5, 6, 7, 8, 9, 10, 11, 12, 13, 14, 15, 20, 25 or more amino acids while still retaining the function similar to that of the light chain variable region of the first binding fragment.

In some embodiments of the first aspect, 1, 2, 3, 4, 5, 6, 7, 8, 9, 10, 11, 12, 13, 14, 15, 20, 25 or more amino acids can also be added to the C-terminal or N-terminal region of the amino acid sequence as set forth in SEQ ID NO:21 or 28, and the resulting amino acid sequences still retain the function similar to that of the light chain variable region of the first binding fragment.

In some embodiments of the first aspect, 1, 2, 3, 4, 5, 6, 7, 8, 9, 10, 11, 12, 13, 14, 15, 20, 25 or more amino acids can also be added or deleted at a region other than the C-terminus or the N-terminus of the amino acid sequence as set forth in SEQ ID NO:21 or 28, provided that the altered amino acid sequences substantially retain the function similar to that of the light chain variable region of the first binding fragment.

In some embodiments of the first aspect, the amino acid sequence of the heavy chain variable region of the second binding fragment differs from the amino acid sequence as set forth in SEQ ID NO:20 by about 1, 2, 3, 4, 5, 6, 7, 8, 9, or 10 amino acid substitutions, deletions, and/or additions.

In some embodiments of the first aspect, the amino acid sequence of the light chain variable region of the second binding fragment differs from the amino acid sequence as set forth in SEQ ID NO:21 or 28 by about 1, 2, 3, 4, 5, 6, 7, 8, 9, or 10 amino acid substitutions, deletions, and/or additions.

In some embodiments of the first aspect, the amino acid sequence of the heavy chain variable region of the second binding fragment has at least 90%, 91%, 92%, 93%, 94%, 95%, 96%, 97%, 98%, 99% or more homology to SEQ ID NO:20.

In some embodiments of the first aspect, the amino acid sequence of the light chain variable region of the second binding fragment has at least 90%, 91%, 92%, 93%, 94%, 95%, 96%, 97%, 98%, 99% or more homology to SEQ ID NO:21 or 28.

In some embodiments of the first aspect, the C-terminal or N-terminal region of the amino acid sequence as set forth in SEQ ID NO:20 can also be truncated by about 1, 2, 3, 4, 5, 6, 7, 8, 9, 10, 11, 12, 13, 14, 15, 20, 25 or more amino acids while still retaining the function similar to that of the heavy chain variable region of the second binding fragment.

In some embodiments of the first aspect, 1, 2, 3, 4, 5, 6, 7, 8, 9, 10, 11, 12, 13, 14, 15, 20, 25 or more amino acids can also be added to the C-terminal or N-terminal region of the amino acid sequence as set forth in SEQ ID NO: 20, and the resulting amino acid sequences still retain the function similar to that of the heavy chain variable region of the second binding fragment.

In some embodiments of the first aspect, 1, 2, 3, 4, 5, 6, 7, 8, 9, 10, 11, 12, 13, 14, 15, 20, 25 or more amino acids can also be added or deleted at a region other than the C-terminus or the N-terminus of the amino acid sequence as set forth in SEQ ID NO: 20, provided that the altered amino acid sequences substantially retain the function similar to that of the heavy chain variable region of the second binding fragment.

In some embodiments of the first aspect, the C-terminal or N-terminal region of the amino acid sequence as set forth in SEQ ID NO: 21 or 28 can also be truncated by about 1, 2, 3, 4, 5, 6, 7, 8, 9, 10, 11, 12, 13, 14, 15, 20, 25 or more amino acids while still retaining the function similar to that of the light chain variable region of the second binding fragment.

In some embodiments of the first aspect, 1, 2, 3, 4, 5, 6, 7, 8, 9, 10, 11, 12, 13, 14, 15, 20, 25 or more amino acids can also be added to the C-terminal or N-terminal region of the amino acid sequence as set forth in SEQ ID NO:21 or 28, and the resulting amino acid sequences still retain the function similar to that of the light chain variable region of the second binding fragment.

In some embodiments of the first aspect, 1, 2, 3, 4, 5, 6, 7, 8, 9, 10, 11, 12, 13, 14, 15, 20, 25 or more amino acids can also be added or deleted at a region other than the C-terminus or the N-terminus of the amino acid sequence as set forth in SEQ ID NO:21 or 28, provided that the altered amino acid sequences substantially retain the function of the light chain variable region of the second binding fragment.

In a second aspect, there is provided in the present application a monoclonal antibody that binds to human TSLP, comprising HCDR1 as set forth in SEQ ID NO:29, HCDR2 as set forth in SEQ ID NO:30, HCDR3 as set forth in SEQ ID NO:31, LCDR1 as set forth in SEQ ID NO:32, LCDR2 as set forth in SEQ ID NO:33, and LCDR3 as set forth in SEQ ID NO:34; wherein the amino acid sequences of HCDR and LCDR are defined according to Kabat.

In some embodiments of the second aspect, the amino acid sequence of the heavy chain variable region of the monoclonal antibody is set forth in SEQ ID NO:24 and the amino acid sequence of the light chain variable region is set forth in SEQ ID NO:21; or the amino acid sequence of the heavy chain variable region of the monoclonal antibody is set forth in SEQ ID NO:24, and the amino acid sequence of the light chain variable region is set forth in SEQ ID NO:28.

In some embodiments of the second aspect, the amino acid sequence of the heavy chain variable region of the monoclonal antibody differs from the amino acid sequence as set forth in SEQ ID NO:24 by about 1, 2, 3, 4, 5, 6, 7, 8, 9, or 10 amino acid substitutions, deletions, and/or additions.

In some embodiments of the second aspect, the amino acid sequence of the light chain variable region of the monoclonal antibody differs from the amino acid sequence as set forth in SEQ ID NO:21 or 28 by about 1, 2, 3, 4, 5, 6, 7, 8, 9, or 10 amino acid substitutions, deletions, and/or additions.

In some embodiments of the second aspect, the amino acid sequence of the heavy chain variable region of the monoclonal antibody has at least 90%, 91%, 92%, 93%, 94%, 95%, 96%, 97%, 98%, 99% or more homology to SEQ ID NO:24.

In some embodiments of the second aspect, the amino acid sequence of the light chain variable region of the monoclonal antibody has at least 90%, 91%, 92%, 93%, 94%, 95%, 96%, 97%, 98%, 99% or more homology to SEQ ID NO:21 or 28.

In some embodiments of the second aspect, the C-terminal or N-terminal region of the amino acid sequence as set forth in SEQ ID NO:24 can also be truncated by about 1, 2, 3, 4, 5, 6, 7, 8, 9, 10, 11, 12, 13, 14, 15, 20, 25 or more amino acids while still retaining the function similar to that of the heavy chain variable region of the monoclonal antibody.

In some embodiments of the second aspect, 1, 2, 3, 4, 5, 6, 7, 8, 9, 10, 11, 12, 13, 14, 15, 20, 25 or more amino acids can also be added to the C-terminal or N-terminal region of the amino acid sequence as set forth in SEQ ID NO: 24, and the resulting amino acid sequences still retain the function similar to that of the heavy chain variable region of the monoclonal antibody.

In some embodiments of the second aspect, 1, 2, 3, 4, 5, 6, 7, 8, 9, 10, 11, 12, 13, 14, 15, 20, 25 or more amino acids can also be added or deleted at a region other than the C-terminus or the N-terminus of the amino acid sequence as set forth in SEQ ID NO: 24, provided that the altered amino acid sequences substantially retain the function similar to that of the heavy chain variable region of the monoclonal antibody.

In some embodiments of the second aspect, the C-terminal or N-terminal region of the amino acid sequence as set forth in SEQ ID NO:21 or 28 can also be truncated by about 1, 2, 3, 4, 5, 6, 7, 8, 9, 10, 11, 12, 13, 14, 15, 20, 25 or more amino acids while still retaining the function similar to that of the light chain variable region of the monoclonal antibody.

In some embodiments of the second aspect, 1, 2, 3, 4, 5, 6, 7, 8, 9, 10, 11, 12, 13, 14, 15, 20, 25 or more amino acids can also be added to the C-terminal or N-terminal region of the amino acid sequence as set forth in SEQ ID NO:21 or 28, and the resulting amino acid sequences still retain the function similar to that of the light chain variable region of the monoclonal antibody.

In some embodiments of the second aspect, 1, 2, 3, 4, 5, 6, 7, 8, 9, 10, 11, 12, 13, 14, 15, 20, 25 or more amino acids can also be added or deleted at a region other than the C-terminus or the N-terminus of the amino acid sequence as set forth in SEQ ID NO:21 or 28, provided that the altered amino acid sequences substantially retain the function similar to that of the light chain variable region of the monoclonal antibody.

In a third aspect, there is provided in the present application a pharmaceutical composition comprising the bispecific antibody of the first aspect, or the monoclonal antibody of the second aspect, and a pharmaceutically acceptable excipient, diluent, or carrier.

In some embodiments of the third aspect, the pharmaceutical composition is used for preventing or treating a TSLP-mediated disease.

In some embodiments of the third aspect, the TSLP-mediated disease is selected from the group consisting of asthma, scleroderma, systemic lupus erythematosus, rheumatoid arthritis, Churg-Strauss syndrome, Wegener's granulomatosis, allergic pneumonia, atopic dermatitis, rhinitis, Crohn's disease, psoriatic arthritis, chronic nephritis, Sjogren's syndrome, and multiple sclerosis.

In some embodiments of the third aspect, the pharmaceutical composition can further comprise one or more of a lubricant, such as talc, magnesium stearate, and mineral oil; a wetting agent; an emulsifier; a suspending agent; a preservative such as benzoic acid, sorbic acid and calcium propionate; a sweetening agent and/or a flavoring agent.

In some embodiments of the third aspect, the pharmaceutical composition herein can be formulated as a tablet, a pill, a powder, a lozenge, an elixir, a suspension, an emulsion, a solution, a syrup, a suppository, or a capsule.

In some embodiments of the third aspect, the pharmaceutical composition of the present application can be delivered using any physiologically acceptable administration route including, but not limited to, oral administration, parenteral administration, nasal administration, rectal administration, intraperitoneal administration, intravascular injection, subcutaneous administration, transdermal administration, or inhalation administration.

In some embodiments of the third aspect, a pharmaceutical composition for therapeutic use can be formulated for storage in the form of a lyophilized formulation or an aqueous solution by mixing an agent with desired purity with a pharmaceutically acceptable carrier or excipient where appropriate.

In a fourth aspect, there is provided in the present application use of the bispecific antibody of the first aspect, the monoclonal antibody of the second aspect, or the pharmaceutical composition of the third aspect in the manufacture of a medicament for the prevention or treatment of a TSLP-mediated disease.

In some embodiments of the fourth aspect, the TSLP-mediated disease is selected from the group consisting of asthma, scleroderma, systemic lupus erythematosus, rheumatoid arthritis, Churg-Strauss syndrome, Wegener's granulomatosis, allergic pneumonia, atopic dermatitis, rhinitis, Crohn's disease, psoriatic arthritis, chronic nephritis, Sjogren's syndrome, and multiple sclerosis.

In a fifth aspect, there is provided in the present application a method of preventing or treating a TSLP-mediated disease, comprising administering to a subject in need thereof the bispecific antibody of the first aspect, the monoclonal antibody of the second aspect, or the pharmaceutical composition of the third aspect.

In some embodiments of the fifth aspect, the TSLP-mediated disease is selected from the group consisting of asthma, scleroderma, systemic lupus erythematosus, rheumatoid arthritis, Churg-Strauss syndrome, Wegener's granulomatosis, allergic pneumonia, atopic dermatitis, rhinitis, Crohn's disease, psoriatic arthritis, chronic nephritis, Sjogren's syndrome, and multiple sclerosis.

In other aspects, there is provided in the present application a nucleic acid molecule encoding the bispecific antibody of the first aspect, or the monoclonal antibody of the second aspect. In some embodiments, the nucleic acid molecule is operably linked to a regulatory sequence that can be recognized by a host cell transformed with the vector.

There is also provided in the present application a vector comprising an isolated nucleic acid molecule encoding the bispecific antibody of the first aspect, or the monoclonal antibody of the second aspect, and a host cell comprising the nucleic acid molecule or the vector. In other aspects, there is provided in the present application a method of producing the bispecific antibody of the first aspect, or the monoclonal antibody of the second aspect. In some embodiments, the method of producing the bispecific antibody of the first aspect, or the monoclonal antibody of the second aspect comprises culturing a host cell so as to facilitate expression of the nucleic acid molecule. In some embodiments, the method of producing the bispecific antibody of the first aspect, or the monoclonal antibody of the second aspect further comprises recovering the bispecific antibody or monoclonal antibody from the host cell culture medium.

It is to be understood that the foregoing detailed description is intended only to enable those skilled in the art to have better understanding of the present application and is not intended to cause limitations in any way. Various modifications and variations can be made to the described embodiments by those skilled in the art.

The following Examples are for purposes of illustration only and are not intended to limit the scope of the present application.

EXAMPLES

Example 1: Preparation of Recombinant Proteins

A number of different recombinant proteins are needed in the preparation of anti-TSLP antibodies, including the long version of the extracellular domain of human TSLP (hTSLP1-ECD, SEQ ID NO:1), the short version of the extracellular domain of human TSLP (hTSLP2-ECD, SEQ ID NO:2), the extracellular domain of mouse TSLP (mTSLP-ECD, SEQ ID NO:3), and the extracellular domain of cynomolgus monkey TSLP (mfTSLP1-ECD, SEQ ID NO:4). These proteins have a large number of post-translational modifications (e.g., glycosylation or disulfide bonds, etc), and therefore, the use of the mammal cell expression system would be more favorable for maintaining the structure and function of the recombinant proteins. In addition, in order to avoid the effect of the furin recognition sites in hTSLP1, hTSLP2 and mfTSLP1 on the activity of the TSLP protein, hTSLP1 mutant (hTSLP1-m, SEQ ID NO:5), hTSLP2 mutant (hTSLP2-m, SEQ ID NO:6) and mfTSLP1 mutant (mfTSLP1-m, SEQ ID NO:7) with deletion of the furin recognition sites were respectively constructed. Meanwhile, the addition of the His tag (His, SEQ ID NO:8) or the Fc fragment of the human antibody IgG1 (hFc, SEQ ID NO:9) or the Fc fragment of the mouse antibody IgG2a (mFc, SEQ ID NO:10) to the C-terminus of these recombinant proteins will be more favorable for the purification of the recombinant proteins and the identification of the monoclonal antibody functions. The antibody heavy chain constant region can be human IgG1 subtype (SEQ ID NO: 11), human IgG2 subtype (SEQ ID NO:12), human IgG4 subtype (SEQ ID NO: 13), or mouse IgG1 subtype (SEQ ID NO:14), or mouse IgG2a subtype (SEQ ID NO: 15), and the light chain constant region can be human kappa subtype (SEQ ID NO:16), human lambda subtype (SEQ ID NO:17), mouse kappa subtype (SEQ ID NO:18), or mouse lambda subtype (SEQ ID NO:19).

According to the amino acid sequences of various recombinant proteins of interest in the Uniprot database, genes (including His tags or hFc or mFc encoding genes) encoding the above various recombinant proteins were designed and synthesized. Various synthesized genes encoding the recombinant proteins were cloned into suitable eukaryotic expression vectors (such as pcDNA3.1, Invitrogen Inc., etc) using conventional molecular biology techniques, and the prepared recombinant antibody expression plasmids were then transfected into HEK293 cells (such as HEK293F, Invitrogen, Inc.) using liposomes (such as 293fectin, Invitrogen, Inc., etc) or other cationically transfected reagents (such as PEI, etc). The cells were cultured in suspension in serum-free mediums for 3-4 days. The culture supernatant was then harvested by centrifugation.

The recombinant protein expressed by fusion with His-tag was subjected to one-step purification of the recombinant protein in the culture supernatant using a metal chelate affinity chromatography column (such as HisTrap FF, GE, Inc, etc). The recombinant protein expressed by the fusion of hFc and mFc was further purified by a ProteinA/G affinity chromatography column (such as Mabselect SURE, GE, Inc., etc). The recombinant protein preservation buffer was then replaced with PBS (pH 7.0) or other suitable buffers by using a desalting column (such as Hitrap desaulting, GE, Inc., etc). If necessary, the antibody sample can be sterilized by filtration and then stored in aliquots at −20° C.

Example 2: Construction and Screening of a Fixed Light Chain-Based TSLP Mouse Immune Library In order to construct a TSLP bispecific antibody based on a common light chain, a light chain variable region of an anti-TSLP monoclonal antibody against a specific epitope was selected in conjunction with a mouse heavy chain variable region which had been matured with a TSLP antigen in vivo, and a single-chain fragment variable (scFv) library was constructed by using conventional molecular biological means for screening anti-TSLP monoclonal antibodies against different epitopes.

Splenocytes were collected from 6-8 week old BALB/c mice after immunisation using hTSLP1-m-His recombinant protein as immunogen. Mouse spleen lymphocytes were isolated by using a mouse lymphocyte isolation solution (Dakewe Biotech Co., Ltd., CAT #DKW33-R0100). Total RNA was extracted from the isolated lymphocytes by using a cellular total RNA extraction kit (Tiangen Biotech (Beijing) Co., Ltd., CAT #DP430). Using the extracted total RNA as a template, the heavy chain variable region of the antibody was synthesized using a first chain cDNA synthesis kit (Thermo scientific, CAT #K1621). The light chain variable region of the monoclonal antibody H1A10+L3E8-M1 that recognized the specific epitope of hTSLP1 was obtained by PCR amplification using conventional molecular biological means (see the humanized antibody H1A10+L3E8-M1 in Chinese Patent Application No. 202010080450.1, with the amino acid sequence of the heavy chain variable region as set forth in SEQ ID NO:20, and the amino acid sequence of the light chain variable region as set forth in SEQ ID NO:21) and the mouse heavy chain variable region was obtained by immunizing mice with hTSLP1-m-His recombinant antigen. Then, the single-chain fragment variables (scFv) was constructed by overlapping extension PCR technology. The genes encoding the prepared mouse single chain fragment variables were cloned into the vector pADSCFV-S (see Example 1 of the Chinese Patent Application No. 201510097117.0 for detailed experimental protocols) to construct a scFv library. The antibody library has a capacity of 8.3E+07, and an accuracy of 65%.

Referring to the reference (Chinese Patent Application No. 201510097117.0), the constructed fixed light chain immune library of mouse was screened by a solid phase screening strategy (as for the experimental protocol, see, Phage Display: A Practical Approach, Tim Clackson (USA) and Henry B. Lowman (USA) (ed.), translated by Lan Ma et al., Chemical Industry Press, May 2008) using the recombinant hTSLP1-m-his prepared in Example 1 as the antigen. Three rounds of screening were carried out by means of binding, elution, neutralization, infection and amplification. Finally, one single chain fragment variable S17C7+L3E8-M1 specifically binding to human TSLP was obtained.

Example 3: Identification of Anti-hTSLP Mouse Monoclonal Antibody

The nucleic acid molecules encoding the light variable region and the heavy chain variable region of S17C7+L3E8-M1 were respectively cloned into eukaryotic expression vectors by using conventional molecular biological methods so as to prepare and express the whole antibody. Meanwhile, the humanized anti-TSLP monoclonal antibody Tezepelumab was prepared according to U.S. Pat. No. 9,284,372B2 as a positive control (the amino acid sequence of the heavy chain variable region is set forth in SEQ ID NO:22; and the amino acid sequence of the light chain variable region is set forth in SEQ ID NO:23).

3.1 Affinity Analysis of the Recombinant Anti-TSLP Monoclonal Antibody S17C7+L3E8-M1

The affinity of the anti-TSLP antibody was determined by the surface plasmon resonance technique using Biacore X100. Reagents and consumables such as an amino-coupling kit (BR-1000-50), a human antibody capture kit (BR-1008-39), a CM5 chip (BR100012) and 10×HBS-EP (pH 7.4, BR100669) were purchased from GE healthcare. The surface of the carboxylated CM5 chip was activated with 1-ethyl-3-(3-dimethylaminopropyl) carbodiimide hydrochlorid (EDC) and N-Hydroxysuccinimide (NHS) according to the instructions in the kit. An anti-human IgG (Fc) antibody (capture antibody) was diluted to 25 μg/mL with 10 mM sodium acetate (pH5.0), and then injected at a flow rate of 10 μL/min to achieve a coupling amount of approximately 10,000 response units (RU). After injection of the capture antibody, 1 M ethanolamine was injected to block unreacted groups. For the kinetics measurement, the anti-TSLP antibody was diluted to 0.5-1 μg/mL, and injected at 10 μL/min to ensure that approximately 100 RU of the antibody was captured by the anti-human Fc antibody. hTSLP1-m-his was then set to a series of concentration gradients (e.g., 0.625 nM, 1.25 nM, 2.5 nM, 5 nM, and 10 nM) and injected at 25° C. from lower to higher concentrations at 30 μL/min, with an association time of 120s and a dissociation time of 3,600s. A 3M $MgCl_2$ solution was injected at 10 μL/min for 30s to regenerate the surface of the chip. The association rate ($K_a$) and dissociation rate ($K_d$) were calculated by fitting the binding and dissociation sensing grams with a 1:1 binding model by using Biacore X100 evaluation software version 2.0.1. The dissociation equilibrium constant ($K_D$) was calculated as the ratio $K_d/K_a$. The fitting results were shown in Table 1.

TABLE 1

Affinity constants for the binding of the recombinant anti-human TSLP monoclonal antibodies to hTSLP

| Monoclonal antibody | $K_a$ | $K_d$ | $K_D$ |
|---|---|---|---|
| Tezepelumab | 8.633E+6 | 1.278E−5 | 1.48E−12 |
| S17C7 + L3E8-M1 | 4.611E+6 | 8.699E−4 | 1.887E−10 |

3.2 Inhibition of the Binding of TSLP to TSLPR by the Recombinant Anti-TSLP Monoclonal Antibody S17C7+L3E8-M1

96-well plates were coated with the recombinant antigen TSLPR-Fc (3 μg/mL, 100 μL/well) overnight at 4° C., and were then blocked with a blocking solution (PBS-0.1% Tween 20-3% milk) at 37° C. for 1 hour. Gradient dilutions of the monoclonal antibodies S17C7+L3E8-M1 and Tezepelumab were performed with hTSLP1-m-his at a fixed concentration (0.2 μg/mL). The starting concentration of the antibodies was 100 μg/mL, and the dilution was carried out at 3-fold for a total of 10 concentration gradients. The antibody dilutions were added to the blocked 96-well ELISA plates at 100 μL/well and the plates were incubated at 37° C. for 1 hour. Then, the ELISA plates were washed with PBS-0.1% Tween 20, followed by the addition of 1:5000 diluted HRP-anti-His labeled mouse monoclonal antibody (Beijing Kangwei Century Biotechnology Co., Ltd., CW0285M) at 100 μL/well and the plates were incubated at 37° C. for 1 hour. The ELISA plates were washed with PBS-0.1% Tween 20, and an OPD substrate chromogenic solution was added. After incubation for 5-10 minutes, the colour development was terminated with 1M $H_2SO_4$. The optical density values were measured using a microplate reader at 492 nm/630 nm dual wavelength. The results from the ELISA assay (FIG. 1) showed that S17C7+L3E8-M1 can completely inhibit the binding of TSLP to TSLPR, and the inhibitory ability of S17C7+L3E8-M1 was comparable to that of Tezepelumab. The $IC_{50}$ values were shown in Table 2.

TABLE 2

$IC_{50}$ values of anti-human TSLP monoclonal antibodies for inhibiting the binding of TSLP toTSLPR

| Monoclonal antibody | S17C7 + L3E8-M1 | Tezepelumab |
|---|---|---|
| $IC_{50}$ (nM) | 1.707 | 1.307 |

Figure 2:
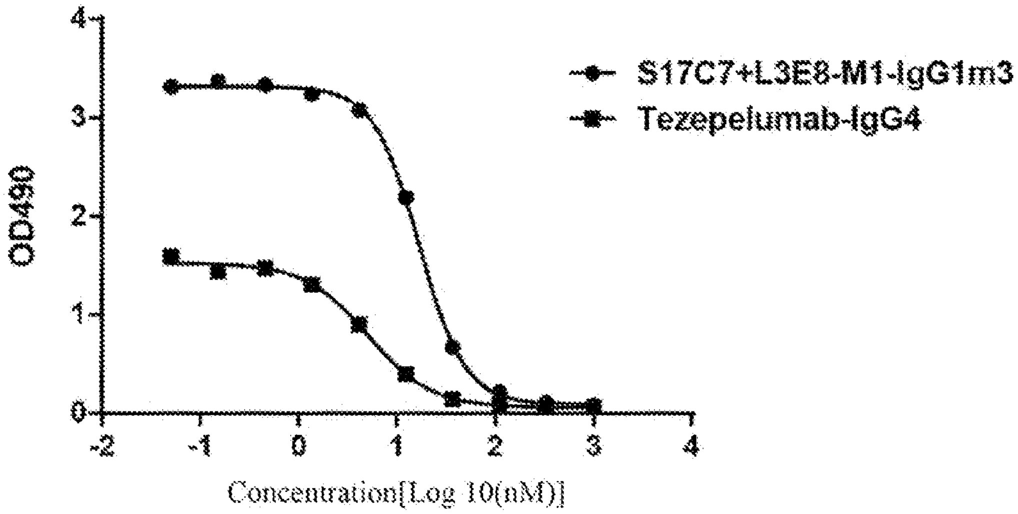
FIG. 2 shows the results from an ELISA assay assessing the ability of the anti-human TSLP monoclonal antibody S17C7+L3E8-M1 to inhibit the binding of Tezepelumab-mIgG2a to TSLP.

3.3 Comparison of the Epitopes of TSLP Bound by the Recombinant Anti-TSLP Monoclonal Antibodies S17C7+L3E8-M1 and Tezepelumab 96-well plates were coated with recombinant protein hTSLP1-m-his (1 μg/mL, 100 μL/well) overnight at 4° C., and were then blocked with a blocking solution (PBS-0.1% Tween 20-3% milk) at 37° C. for 1 hour. Gradient dilutions of Tezepelumab-IgG4 and S17C7+L3E8-M1-IgG1m3 were performed with PBS-2% milk containing recombinant antibody Tezepelumab-mIgG2a at 0.05 μg/mL. The starting concentration of the antibodies was 200 μg/mL, and the dilution was carried out at 3-fold for a total of 10 concentration gradients. The antibody dilutions were added to the blocked 96-well ELISA plates at 100 μL/well and the plates were incubated at 37° C. for 1 hour. Then, the ELISA plates were washed with PBS-0.1% Tween 20, followed by the addition of 1:5000 diluted HRP-goat-anti-mouse IgG (Beijing Zhongshan Jingiao Biotechnology Co., Ltd., ZB2305) at 100 μL/well and the plates were incubated at 37° C. for 1 hour. The ELISA plates were washed with PBS-0.1% Tween 20, and an OPD substrate chromogenic solution was added. After incubation for 5-10 minutes, the colour development was terminated with 1M $H_2SO_4$. The optical density values were measured using a microplate reader at 492 nm/630 nm dual wavelength. Data were analyzed and graphed using GraphPad Prism 6. The results from the ELISA assay (FIG. 2) showed that S17C7+L3E8-M1-IgG1m3 can completely inhibit the binding of Tezepelumab-mIgG2a to TSLP. The $IC_{50}$ values were shown in Table 3. The $IC_{50}$ value of S17C7+L3E8-M1-IgG1m3 for inhibiting the binding of Tezepelumab-mIgG2a to TSLP was 2.2-fold higher than that of Tezepelumab-IgG4 for inhibiting the binding of Tezepelumab-mIgG2a to TSLP, which may be related to the lower affinity of the binding of S17C7+L3E8-M1-IgG1m3 to TSLP than that of the binding of Tezepelumab-IgG4 to TSLP (see Table 1).

TABLE 3

$IC_{50}$ values of anti-human TSLP monoclonal antibodies for inhibiting the binding of Tezepelumab-mIgG2a to TSLP

| Monoclonal antibody | S17C7 + L3E8-M1-IgG1m3 | Tezepelumab-IgG4 |
|---|---|---|
| $IC_{50}$ (nM) | 3.223 | 1.467 |

3.4 Inhibition of the Proliferation-Promoting Effect of TSLP on BAF3-TSLPR/IL-7Rα Cells by the Recombinant Anti-Human TSLP Monoclonal Antibody S17C7+L3E8-M1

Figure 3:
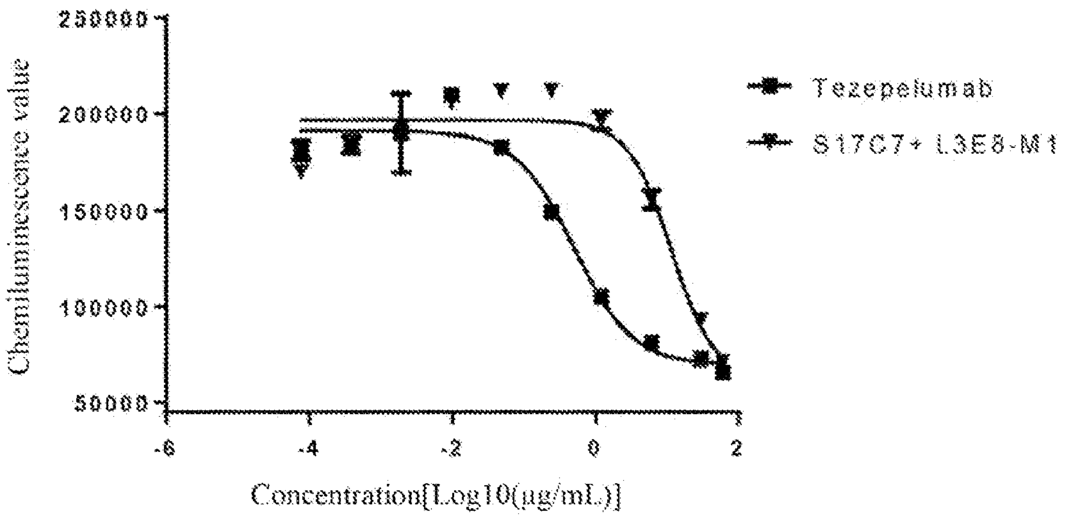
FIG. 3 shows the results from a chemiluminescent cell viability assay assessing the ability of the anti-human TSLP monoclonal antibody S17C7+L3E8-M1 to inhibit the proliferation-promoting effect of TSLP on BAF3-TSLPR/IL-7Rα cells.

BAF3-TSLPR/IL-7Rα was a stable transgenic cell strain with high expression of the TSLP receptor and its proliferation was dependent on mIL-3. In the absence of mIL-3, TSLP can effectively promote the proliferation of BA/F3-TSLPR/IL-7Rα cells. This method can be used to evaluate anti-human TSLP monoclonal antibody to inhibit the proliferation-promoting effect of TSLP on BAF3-TSLPR/IL-7Rα cells. In the experiment, BAF3-TSLPR/IL-7Rα cells were pre-cultured for two days using complete medium without mIL-3. On the day of the experiment, cells were centrifugated and resuspended to a density of $1\times10^6$ cells/mL, and added to 96-well flat bottom cell culture plates at 50 μL/wells. The dilutions of the recombinant anti-human TSLP monoclonal antibody S17C7+L3E8-M1 and the positive control antibody (i.e., Tezepelumab) were both started at a final concentration of 60 μg/mL, with a second concentration of 30 μg/mL, followed by a 5-fold gradient of each of 8 concentration gradients. The diluted anti-human TSLP monoclonal antibody was premixed with an equal volume of hTSLP-m-his at a final concentration of 0.4 ng/mL for 30 minutes, and then the mixture was mixed with BAF3-TSLPR/IL-7Rα cells and incubated in a total volume of 150 μL/wells. After 48 hours, the cell proliferation was determined by a multifunctional microplate reader (SpectraMax®I3X) using the Cell Titer-Glo® Luminescent Cell Viability Assay Kit (Promega, Cat #G7570). The results of chemiluminescence readings were fitted and analyzed. The results (FIG. 3) showed that both of the anti-human monoclonal antibody S17C7+L3E8-M1 and the positive control antibody (i.e., Tezepelumab) were effective in inhibiting the proliferation-promoting effect of TSLP on BAF3-TSLPR/IL-7Rα cells.

3.5 Effect of the Recombinant Anti-Human TSLP Monoclonal Antibody S17C7+L3E8-M1 on Inhibiting the Secretion of TARC by PBMCs Stimulated by TSLP Blood was collected from normal volunteers (50 mL each), where the collected blood was provided by the inventors and colleagues thereof as volunteers, and all of them had signed informed consent. The inclusion criteria for volunteers were:

1. older than 18 years;
2. no HIV and HBV infections;
3. normal blood routine tests;
4. non-pregnant or lactating women.

Human peripheral blood mononuclear cells (PBMCs) were isolated from healthy human peripheral blood using Ficoll density gradient centrifugation.

Figure 4:
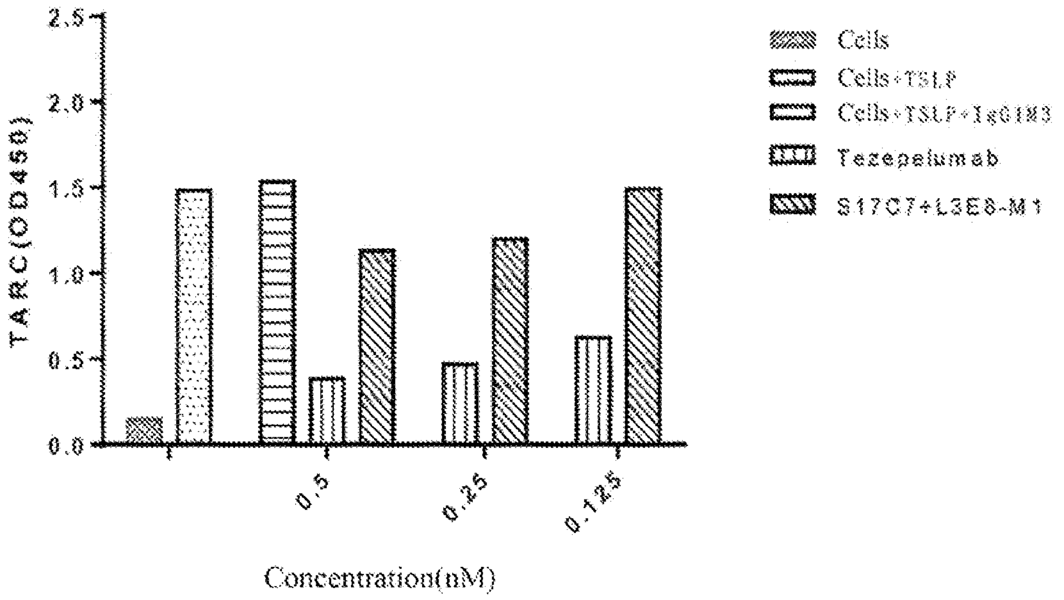
FIG. 4 shows the results from an ELISA assay assessing the ability of the anti-human TSLP monoclonal antibody S17C7+L3E8-M1 to inhibit the secretion of TRAC by PBMCs stimulated by TSLP.

The binding of TSLP to TSLPR on dendritic cells can cause activation of the dendritic cells, which exhibits the secretion of chemokines (e.g., TARC, also known as CCL17). The inhibitory effect of recombinant anti-TSLP antibodies on TSLP can be effectively evaluated by detecting TARC. PBMCs were resuspended in R1640 medium containing 10% (inactivated) serum to a density of $2\times10^7$ cells/mL and were added to 96-well flat bottom cell culture plates (50 μL/well). The dilutions of the recombinant anti-human TSLP monoclonal antibody S17C7+L3E8-M1 and the positive control antibody (i.e., Tezepelumab) were both started at a final concentration of 0.5 nM, with a 2-fold gradient for a total of 3 working concentrations. The diluted recombinant anti-human TSLP monoclonal antibody was premixed with an equal volume of hTSLP-m-his at a final concentration of 1 ng/mL for 30 minutes, and then the mixture was added to the cells for mixing, with a total volume of 150 μL/well. No TSLP control (cells), no antibody control (cells +TSLP), and IgG1m3 isotype antibody control (cells +TSLP+IgG1m3) were set. The mixture was incubated at 37° C., 5% $CO_2$ for 24 hours. The supernatant was then taken and the TARC was detected by using the humanized antibody TARC matched ELISA antibody pair set (Sino Biological Inc., Cat #SEK10233) based on an ELISA assay. The chromogenic solution was a TMB high-sensitivity substrate solution (Biolegend, Cat #421501). The optical density value of OD450 was determined using a microplate reader (Biotek, Cat #ELX800). The readings were analyzed. The results (FIG. 4) showed that both of the recombinant anti-human TSLP monoclonal antibody S17C7+L3E8-M1 and the control antibody Tezepelumab can inhibit the secretion of TARC by PBMCs stimulated by TSLP.

Example 4: Humanized Engineering and Functional Identification of Mouse Anti-Human TSLP Monoclonal Antibody The humanization of the heavy chain of the anti-human TSLP mouse monoclonal antibody S17C7+L3E8-M1 employed a classical framework transplantation strategy (*J immunol.* 169, 1119-1125, 2002). The heavy chain variable region of S17C7+L3E8-M1 was compared with the human antibody germline genetic sequence in the IMGT database. The appropriate germline genetic sequence was selected to provide the framework regions 1 to 3 of the antibody (FR1+FR2+FR3), and the appropriate J region genetic sequence was selected to provide the framework region 4 (FR4). This template can be selected according to a variety of factors, such as the relative total length of the antibody, the size of the CDRs, the amino acid residues located at the junction between the framework region (FR) and the hypervariable region (CDR) of the antibody, and the homology of the whole entire sequences. The selected template can be a mixture of multiple sequences or can be a consensus template, with the aim of maintaining the appropriate conformation of the parental complementarity determining regions (CDR) as much as possible. The humanized heavy chain mutant H3B10-M1 (SEQ ID NO:24) was finally obtained. An antibody variable region gene was designed and synthesized based on the amino acid sequence of the humanized antibody, cloned into a eukaryotic expression vector and expressed with light chain L3E8-M1 as a whole antibody H3B10-M1+L3E8-M1.

Referring to Example 3.1, affinity analysis was performed on the humanized monoclonal antibody H3B10-M1+L3E8-M1 of S17C7+L3E8-M1 using Biacore X100, and the results were shown in Table 4.

TABLE 4

Affinity constant for the binding of the humanized monoclonal antibody H3B10-M1 + L3E8-M1 to hTSLP

| Monoclonal antibody | $K_a$ | $K_d$ | $K_D$ |
|---|---|---|---|
| S17C7 + L3E8-M1 | 1.524E+7 | 1.767E−3 | 1.159E−10 |
| H3B10-M1 + L3E8-M1 | 1.782E+7 | 1.152E−3 | 6.464E−11 |

Figure 5:
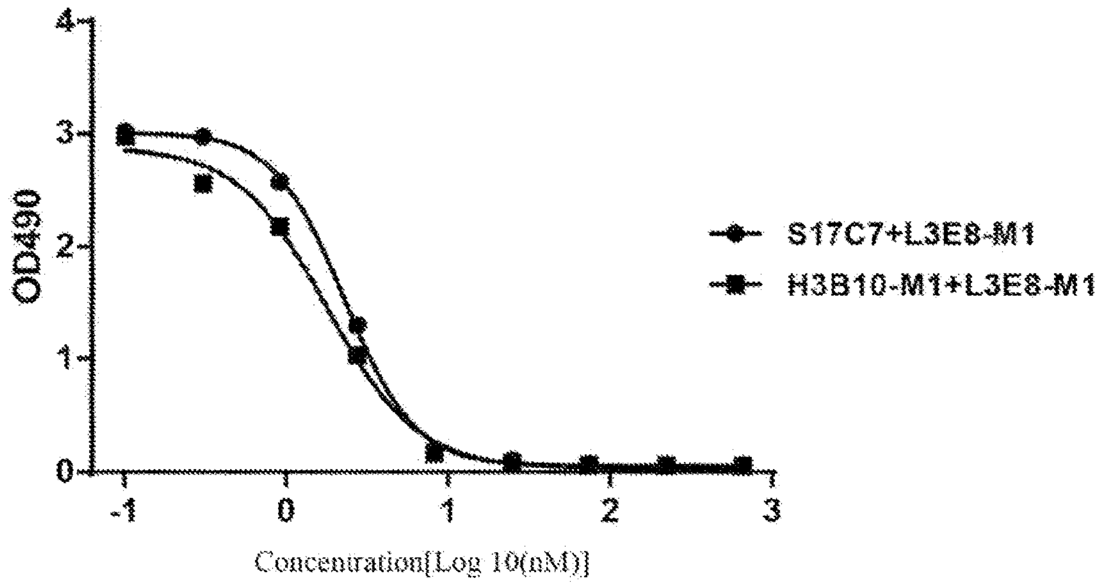
FIG. 5 shows the inhibitory effect of the humanized anti-human TSLP monoclonal antibody H3B10-M1+L3E8-M1 on the binding of TSLP to TSLPR.

Referring to Example 3.2, the ability of the humanized monoclonal antibody H3B10-M1+L3E8-M1 to inhibit the binding of TSLP to TSLPR was analyzed by an ELISA assay. The results from the ELISA assay (FIG. 5) showed that the humanized monoclonal antibody H3B10-M1+L3E8-M1 can completely inhibit the binding of TSLP to TSLPR. The $IC_{50}$ values were shown in Table 5.

TABLE 5

$IC_{50}$ values of the humanized antibody H3B10-M1 + L3E8-M1 for inhibiting the binding of T TSLP to TSLPR

| Monoclonal antibody | S17C7 + L3E8-M1 | H3B10-M1 + L3E8-M1 |
|---|---|---|
| $IC_{50}$ (nM) | 2.288 | 1.787 |

Example 5: Optimization and Identification of the Common Light Chain L3E8-M1

5.1 Engineering of the Common Light Chain L3E8-M1

In the process of humanization of mouse antibodies, changes in the amino acids of the framework region may lead to conformational changes in the antibody, which affects normal folding and secretion of the antibodies, damages the stability of the antibodies, and thereby affecting the expression of the antibodies. The common light chain L3E8-M1 cooperated with the heavy chain H1A10 and H3B10-M1 to express monoclonal antibodies, respectively. The expression levels were significantly reduced compared with the expression level of the patent sequence L3E8. Compared with the expression levels of other mutants of L3E8 (see L3E8-M1, with the amino acid sequence as set forth in SEQ ID NO:21; L3E8-M2, with the amino acid sequence as set forth in SEQ ID NO:25; L3E8-M3, with the amino acid sequence as set forth in SEQ ID NO:26; and L3E8-M4, with the amino acid sequence as set forth in SEQ ID NO:27 disclosed in the Chinese Patent Application No. 202010080450.1), a new mutant L3E8-M7 (SEQ ID NO:28) was constructed by introducing L78V and S80A mutations in the variable region of L3E8-M1. The antibody variable region gene was designed and synthesized based on the amino acid sequence of L3E8-M7, cloned into a eukaryotic expression vector, and was expressed respectively with H1A10 and H3B10-M1 heavy chains as whole antibodies. Referring to Example 1, the expression levels of the whole antibodies with different light chains L3E8, L3E8-M1, and L3E8-M7 were compared. The expression level of L3E8-M7 was recovered to that of parent L3E8, which was significantly superior to the expression level of L3E8-M1.

5.2 Affinity Analysis of the Humanized Antibody H3B10-M1+L3E8-M7

Referring to Example 3.1, affinity analysis of H3B10-M1+L3E8-M7 was performed using Biacore X100 and the results were shown in Table 6.

TABLE 6

Affinity constant for the binding of H3B10-M1 + L3E8-M7 to hTSLP

| Monoclonal antibody | $K_a$ | $K_d$ | $K_D$ |
|---|---|---|---|
| H3B10-M1 + L3E8-M7 | 1.742E+7 | 1.056E−3 | 6.061E−11 |
| H3B10-M1 + L3E8-M1 | 1.782E+7 | 1.152E−3 | 6.464E−11 |
| H1A10 + L3E8-M7 | 2.053E+6 | 2.131E−5 | 1.038E−11 |

5.3 Inhibition of Proliferation-Promoting Effect of TSLP on BAF3-TSLPR/IL-7Rα Cells by the Humanized Antibody H3B10-M1+L3E8-M7

Figure 6:
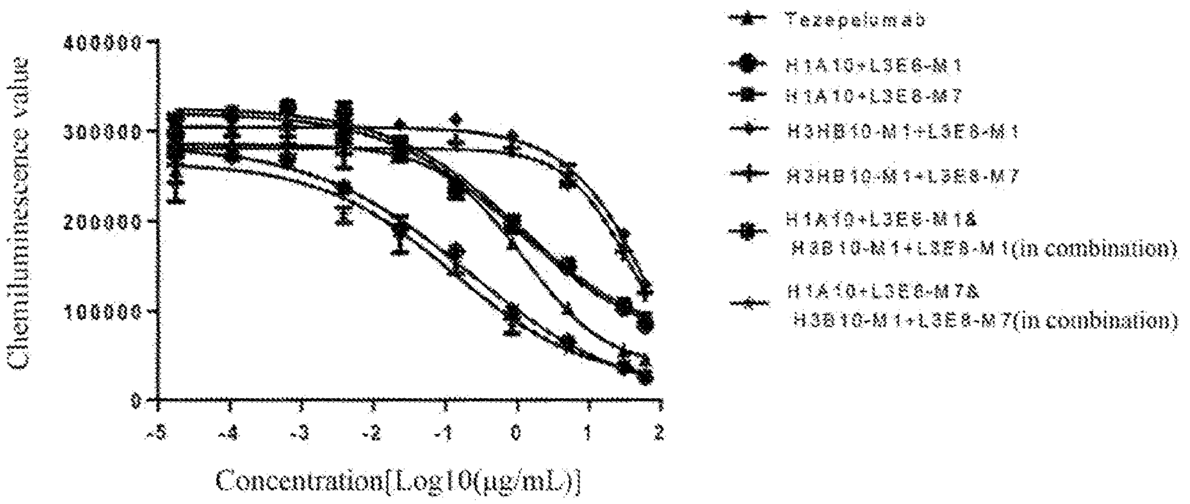
FIG. 6 shows the results from a chemiluminescent cell viability assay assessing the abilities of anti-human TSLP monoclonal antibodies and two monoclonal antibodies in combination to inhibit the proliferation-promoting effect of TSLP on BAF3-TSLPR/IL-7Rα cells.

BAF3-TSLPR/IL-7Rα cells were treated referring to Example 3.4. On the day of the experiment, the cells were centrifugated and resuspended to the density of $1\times10^6$ cells/mL, and added to 96-well flat bottom cell culture plates at 50 μL/well. The dilutions of the recombinant anti-human TSLP monoclonal antibodies (H1A10+L3E8-M1, H1A10+L3E8-M7, H3B10-M1+L3E8-M1 and H3B10-M1+L3E8-M7) and the positive control antibody (i.e., Tezepelumab) were all started at a final concentration of 60 μg/mL, with a second concentration of 30 μg/mL, followed by a 6-fold gradient of each of 8 concentration gradients. The doses of the combined experimental groups (H1A10+L3E8-M1&H3B10-M1+L3E8-M1 and H1A10+L3E8-M7&H3B10-M1+L3E8-M7) were half doses of each of the monoclonal antibodies. The diluted anti-human TSLP monoclonal antibody was premixed with an equal volume of hTSLP-m-his at a final concentration of 0.4 ng/mL for 30 minutes, and then the mixture was mixed with BAF3-TSLPR/IL-7Rα cells and incubated in a total volume of 150 μL/wells. After 48 hours, the cell proliferation was determined by a multifunctional microplate reader (SpectraMax®I3X) using the Cell Titer-Glo® Luminescent Cell Viability Assay Kit (Promega, Cat #G7570). The results of chemiluminescence readings were fitted and analyzed. The results (FIG. 6) showed that both of the monoclonal antibodies H1A10+L3E8-M7 and H3B10-M1+L3E8-M7 with L3E8-M7 light chain effectively inhibited the proliferation-promoting effect of TSLP on BAF3-TSLPR/IL-7Rα cells, and that their activities were comparable to those of the monoclonal antibodies H1A10+L3E8-M1 and H3B10-M1+L3E8-M1 with L3E8-M1 light chain. Compared with the monoclonal antibody and the positive control antibody (i.e., Tezepelumab), the combined experimental groups had more significant inhibition of proliferation-promoting effect of TSLP on BAF3-TSLPR/IL-7Rα cells.

5.4 Effect of the Humanized Antibody H3B10-M1+L3E8-M7 on Inhibiting the Secretion of TARC by PBMCs Stimulated by TSLP PBMC cells were obtained referring to Example 3.5. On the day of the experiment, PBMCs were resuspended in R1640 medium containing 10% (inactivated) serum to a density of $2\times10^7$ cells/mL and were added to 96-well flat bottom cell culture plates (50 μL/well). The dilutions of the anti-human TSLP monoclonal antibodies (H1A10+L3E8-

Figure 7:
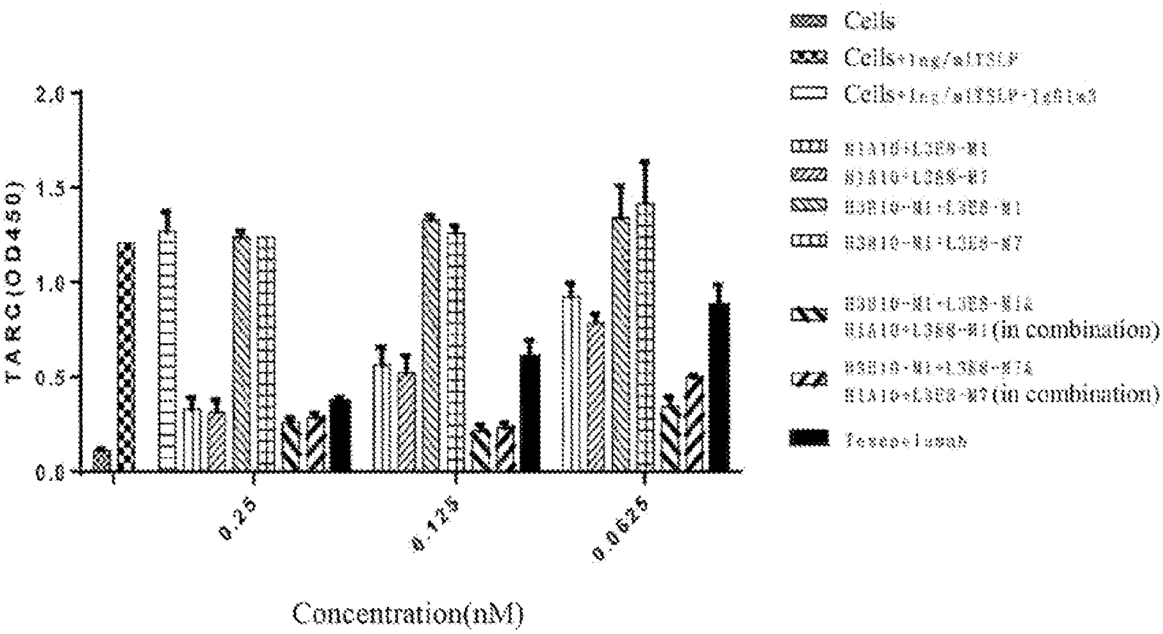
FIG. 7 shows the results from an ELISA assay assessing the abilities of anti-human TSLP monoclonal antibodies and two monoclonal antibodies in combination to inhibit the secretion of TRAC by PBMCs stimulated by TSLP.

M1, H1A10+L3E8-M7, H3B10-M1+L3E8-M1 and H3B10-M1+L3E8-M7) and the positive control antibody (i.e., Tezepelumab) were all started at a final concentration of 0.25 nM, with a 2-fold gradient for a total of 3 working concentrations. The doses of the combined experimental groups (H1A10+L3E8-M1&H3B10-M1+L3E8-M1 and H1A10+L3E8-M7& H3B10-M1+L3E8-M7) were half doses of each of the monoclonal antibodies. No TSLP control (cells), no antibody control (cells +1 ng/mL TSLP), and IgG1m3 isotype antibody control (cells +1 ng/mL TSLP+IgG1m3) were set. The diluted recombinant anti-human TSLP monoclonal antibody was premixed with an equal volume of hTSLP-m-his at a final concentration of 1 ng/mL for 30 minutes, and then the mixture was added to the cells for mixing, with a total volume of 150 μL/well. The mixture was incubated at 37° C., 5% $CO_2$ for 24 hours. The supernatant was then taken and the TARC was detected using the humanized antibody TARC matched ELISA antibody pair set (Sino Biological Inc., Cat #SEK10233) based on an ELISA assay. The chromogenic solution was a TMB high-sensitivity substrate solution (Biolegend, Cat #421501). The optical density value of OD450 was determined using a microplate reader (Biotek, Cat #ELX800). The readings were analyzed. The results (FIG. 7) showed that both of the monoclonal antibodies H1A10+L3E8-M7 and H3B10-M1+L3E8-M7 with L3E8-M7 light chain effectively inhibited the secretion of TARC by PBMCs stimulated by TSLP, and that their activities were comparable to those of the monoclonal antibodies H1A10+L3E8-M1 and H3B10-M1+L3E8-M1 with L3E8-M1 light chain. Compared with the monoclonal antibodies and the positive control antibody (i.e., Tezepelumab), the combined experimental groups had more significant inhibition of the secretion of TARC by PBMCs stimulated by TSLP.

Example 6: Preparation and Identification of Anti-Human TSLP Bispecific Antibodies

6.1 Preparation of Anti-Human TSLP Bispecific Antibodies

The nucleotide sequences encoding the heavy chain variable regions H1A10 and H3B10-M1 of the monoclonal antibodies against two different epitopes of human TSLP were respectively cloned into suitable eukaryotic expression vectors to construct heterodimers based on the common light chain L3E8-M7. That is, the nucleotide sequence encoding the H1A10 heavy chain variable region was cloned into a eukaryotic expression vector fused with the nucleotide sequence encoding the IgG1 constant region IgG1m3-K with Knob mutation; the nucleotide sequence encoding the H3B10-M1 heavy chain variable region was cloned into a eukaryotic expression vector containing the nucleotide sequence encoding the IgG1 constant region IgG1m3-H with Hole mutation; and the nucleotide sequence encoding the common light chain L3E8-M7 variable region was cloned into a eukaryotic expression vector fused with the nucleotide sequence encoding the human light chain constant region CK.

The three constructed eukaryotic expression vectors expressing H1A10-IgG1m3-K, H3B10-M1-IgG1m3-H and L3E8-M7-CK were co-transfected into HEK293F cells using liposomes, and the cells were cultured in suspension in a serum-free medium for 3-5 days. The culture supernatant was harvested by centrifugation. The bispecific antibodies in the culture supernatant were purified using a Protein A/G affinity chromatography column (e.g., Mabselect SURE, GE Inc., etc). The recombinant protein preservation buffer was then replaced with a BS buffer (pH 7.0) or other suitable buffers using a desalting column (e.g., Hitrap desaulting, GE Inc., etc). The desalted protein solution was purified by a size exclusion chromatography (SEC) using Superdex 200 (GE) to obtain the protein of interest. If necessary, the antibody samples can be sterilized by filtration and then stored in aliquots at −20° C. for use.

6.2 Affinity Analysis of Anti-Human TSLP Bispecific Antibodies

Referring to Example 3.1, the affinities of the anti-human TSLP bispecific antibody (BsAb) molecules and the monoclonal antibody molecules binding to human TSLP (hTSLP) and cynomolgus monkey TSLP (mfTSLP) was analyzed using Biacore X 100. The results were shown in Tables 7 and 8.

TABLE 7

Affinity constants for the binding of anti-human TSLP antibodies to hTSLP

| Antibody | $K_a$ | $K_d$ | $K_D$ |
|---|---|---|---|
| H3B10-M1 + L3E8-M7 | 1.477E+7 | 1.176E−3 | 7.963E−11 |
| H1A10 + L3E8-M7 | 2.828E+6 | 3.999E−5 | 1.414E−11 |
| H1A10 × H3B10-M1 + L3E8-M7 BsAb | 1.741E+7 | 1.118E−4 | 6.421E−12 |
| H1A10 × H3B10-M1 + L3E8-M1 BsAb | 1.618E+7 | 1.313E−4 | 8.115E−12 |

TABLE 8

Affinity constants for the binding of anti-human TSLP antibodies to mfTSLP

| Antibody | $K_a$ | $K_d$ | $K_D$ |
|---|---|---|---|
| H1A10 + L3E8-M7 | 4.241E+6 | 1.205E−2 | 2.842E−9 |
| H1A10 × H3B10-M1 + L3E8-M7 BsAb | 7.132E+6 | 1.963E−2 | 2.753E−9 |
| H1A10 × H3B10-M1 + L3E8-M1 BsAb | 1.004E+7 | 2.497E−2 | 2.487E−9 |

Figure 8:
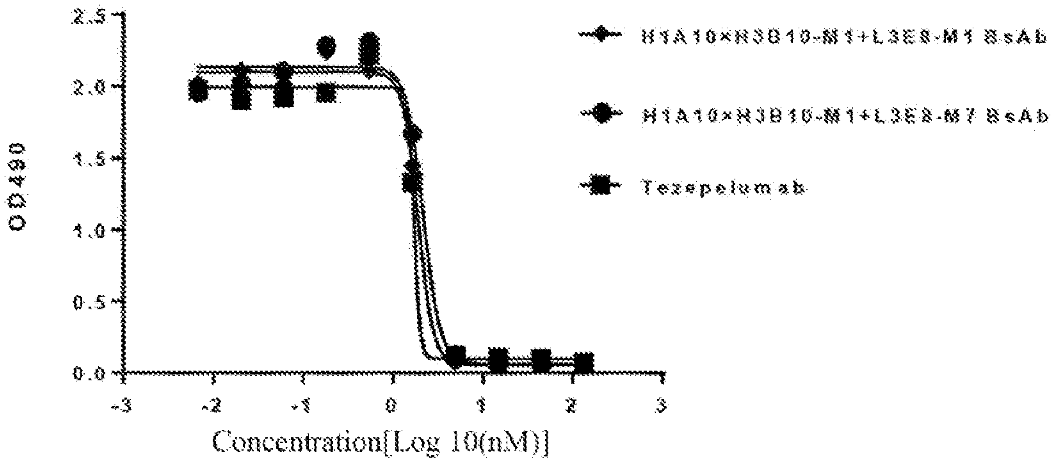
FIG. 8 shows the results from an ELISA assay assessing the inhibitory effects of anti-human TSLP bispecific antibodies on the binding of TSLP to TSLPR.

6.3 Inhibition of the Binding of TSLP to TSLPR by Anti-Human TSLP Bispecific Antibodies Referring to Example 3.2, the abilities of anti-TSLP bispecific antibodies to inhibit the binding of TSLP to TSLPR were analyzed by an ELISA assay. The results from the ELISA assay (FIG. 8) showed that the abilities of the anti-human TSLP bispecific antibodies H1A10×H3B10-M1+L3E8-M1 BsAb and H1A10×H3B10-M1+L3E8-M7 BsAb to inhibit the binding of TSLP to TSLPR were comparable to that of Tezepelumab. The $IC_{50}$ values were shown in Table 9.

TABLE 9

$IC_{50}$ values of anti-human TSLP bispecific antibodies for inhibiting the binding of TSLP to TSLPR

| Antibody | H1A10 × H3B10-M1 + L3E8-M1 BsAb | H1A10 × H3B10-M1 + L3E8-M7 BsAb | Tezepelumab |
|---|---|---|---|
| $IC_{50}$(nM) | 1.906 | 2.171 | 1.724 |

Figure 9:
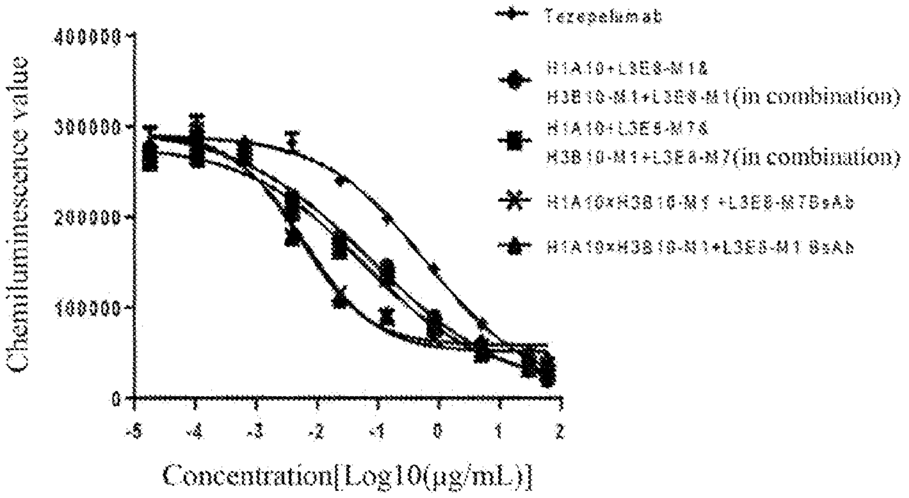
FIG. 9 shows the results from a chemiluminescent cell viability assay assessing the abilities of anti-human TSLP bispecific antibodies to inhibit the proliferation-promoting effect of TSLP on BAF3-TSLPR/IL-7Rα cells.

6.4 Inhibition of the Proliferation-Promoting Effect of TSLP on BAF3-TSLPR/IL-7Rα Cells by Anti-Human TSLP Bispecific Antibodies Referring to Example 5.3, the cell proliferation was determined using the Cell Titer-Glo® Luminescent Cell Viability Assay Kit (Promega, Cat #G7570) and the values were read by a multifunctional microplate reader (SpectraMax® I3X). The results (FIG. 9) showed that compared with the combined experimental groups (H1A10+L3E8-M1&H3B10-M1+L3E8-M1 and H1A10+L3E8-M7&H3B10-M1+L3E8-M7) and the positive control antibody (i.e., Tezepelumab), the anti-human TSLP bispecific antibodies (H1A10×H3B10-M1+L3E8-M1 BsAb and H1A10×H3B10-M1+L3E8-M7 BsAb) had more significant inhibition of the proliferation-promoting effect of TSLP on BAF3-TSLPR/IL-7Rα cells.

Figure 10:
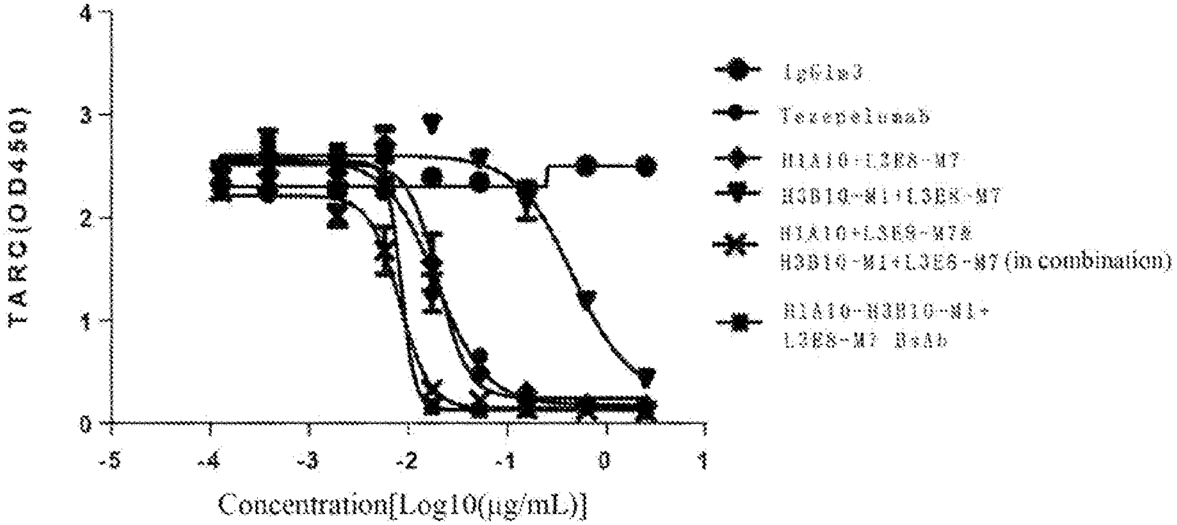
FIG. 10 shows the results from an ELISA assay assessing the ability of anti-human TSLP bispecific antibody to inhibit the secretion of TARC by PBMCs stimulated by TSLP.

6.5 Effect of Anti-Human TSLP Bispecific Antibody on Inhibiting the Secretion of TARC by PBMCs Stimulated by TSLP PBMC cells were obtained referring to Example 3.5. On the day of the experiment, PBMCs were resuspended in R1640 medium containing 10% (inactivated) serum to a density of $2\times10^7$ cells/mL and were added to 96-well flat bottom cell culture plates (50 μL/well). The dilutions of the anti-human TSLP monoclonal antibodies H1A10+L3E8-M7 and H3B10-M1+L3E8-M7, the anti-human TSLP bispecific antibody H1A10×H3B10-M1+L3E8-M7 BsAb and the positive control antibody (i.e., Tezepelumab) were all started at a final concentration of 0.25 μg/mL, with a 4-fold dilution for the first 3 points, a 3-fold dilution for the middle $4^{th}$-$6^{th}$ points, and a 5-fold dilution for $7^{th}$-$9^{th}$ points. The dose of the combined experimental group (H1A10+L3E8-M7& H3B10-M1+L3E8-M7) was half dose of each of the monoclonal antibodies. IgG1m3 was used as the isotype antibody control. The diluted anti-human TSLP antibody was premixed with an equal volume hTSLP-m-his at a final concentration of 1 ng/mL for 30 minutes, and then the mixture was added to the cells for mixing, with a total volume of 150 μL/well. The mixture was incubated at 37° C., 5% $CO_2$ for 24 hours. The supernatant was then taken and the TARC was detected using the humanized antibody TARC matched ELISA antibody pair set (Sino Biological Inc., Cat #SEK10233) based on an ELISA assay. The chromogenic solution was a TMB high-sensitivity substrate solution (Biolegend, Cat #421501). The optical density value of OD450 was determined using a microplate reader (Biotek, Cat #ELX800). The readings were fitted and analyzed. The results showed (FIG. 10) that compared with the monoclonal antibody experimental groups and the positive control antibody (i.e., Tezepelumab), the bispecific antibody and the combined experimental group had more significant inhibition of the secretion of TARC by PBMCs stimulated by TSLP.

Example 7: Dual Epitope Analysis of Anti-Human TSLP Bispecific Antibody 7.1 Dual Epitope Identification of Anti-Human TSLP Bispecific Antibody The binding epitopes of anti-TSLP antibody were analyzed by surface plasmon resonance technique using Biacore T200.

Reagent Consumables

An amino coupling kit (BR-1000-50), a His kit (28995056), a S-series CM5 chip (BR100530), and 10×HBS-EP (pH 7.4, BR100669) and so on were all available from GE healthcare.

Chip Coupling

The surface of the carboxylated CM5 chip was activated with 1-ethyl-3-(3-dimethylaminopropyl) carbodiimide hydrochloride (EDC) and N-hydroxysuccinimide (NHS) according to the instructions in the amino coupling kit. An anti-His antibody (capture antibody) was diluted to 25 μg/mL with 10 mM sodium acetate (pH 5.0), and then injected at a flow rate of 10 μL/min to achieve a coupling amount of approximately 12,000 response units (RU). After the injection of capture antibody, 1 M ethanolamine was injected to block the unreacted groups.

Epitope Analysis

The recombinant protein hTSLP1-m-His was diluted to 2 μg/mL with 1×HBS-EP and injected at 10 μL/min for 12 seconds to ensure that about 25 RU of the hTSLP1-m-His was captured by the anti-His antibody. The anti-human TSLP monoclonal antibodies H3B10-M1+L3E8-M7, H1A10+L3E8-M7 and Tezepelumab, and the anti-human TSLP bispecific antibody H1A10×H3B10-M1+L3E8-M7 (H1A10×H3B10-M1+L3E8-M7 BsAb) were diluted to 45 μg/ml with 1×HBS-EP, respectively. Different antibodies were sequentially injected using a double injection mode of Biacore T200. That is, the first antibody flowed through the surface of the chip capturing the antigen hTSLP-m-His at a flow rate of 30 μL/min, followed by the injection of the second antibody. Each of the antibodies was injected for 120 seconds. The surface of the chip was regenerated at the end of the injection by injecting 1.7 mM glycine-HCl at 10 μL/min for 30s. The capture level reporting point for hTSLPT-m-His was zeroed using Biacore T200 evaluation software version 3.0, and then the RU values were plotted against times using GraphPad software (connecting lines).

Figure 11:
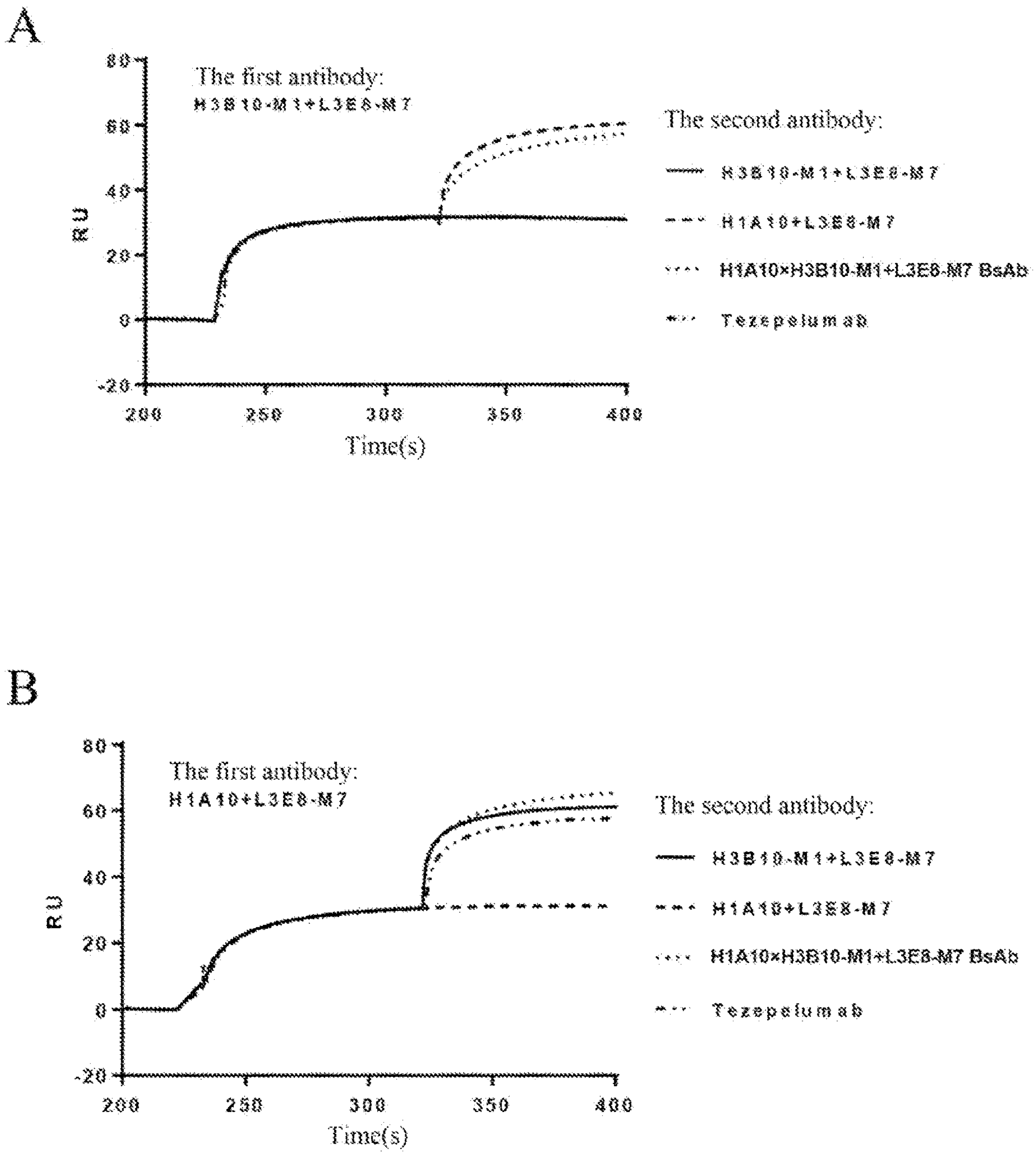
FIG. 11 shows the results of analyzing the binding epitopes of the anti-human TSLP antibodies using Biacore T200, in which panels A-D respectively show the results of analysis by using H3B10-M1+L3E8-M7, H1A10+L3E8-M7, the bispecific antibody H1A10×H3B10-M1+L3E8-M7 and Tezepelumab as the first antibodies.
Figure 11:
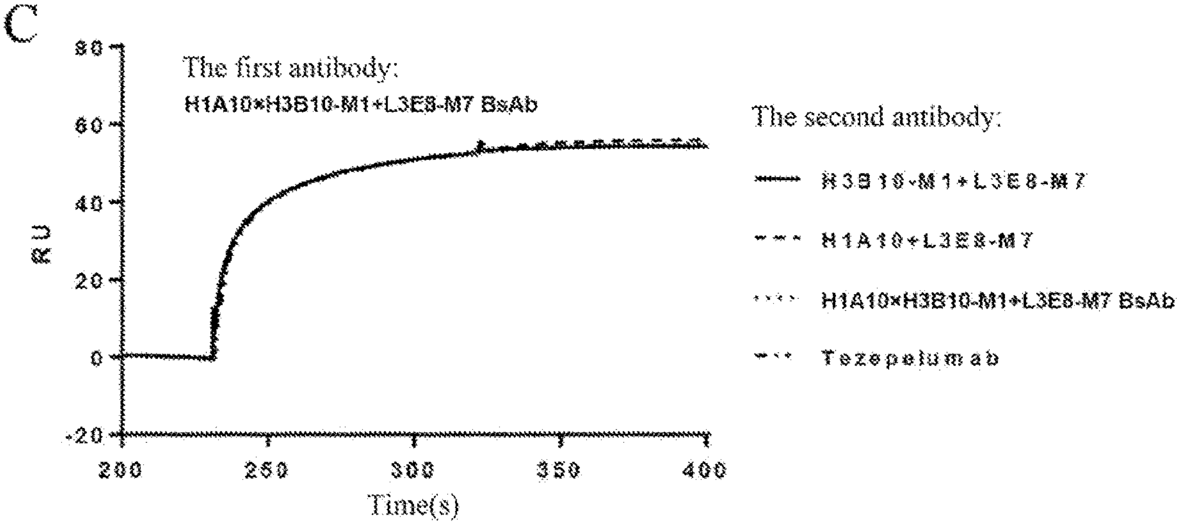
Figure 11:
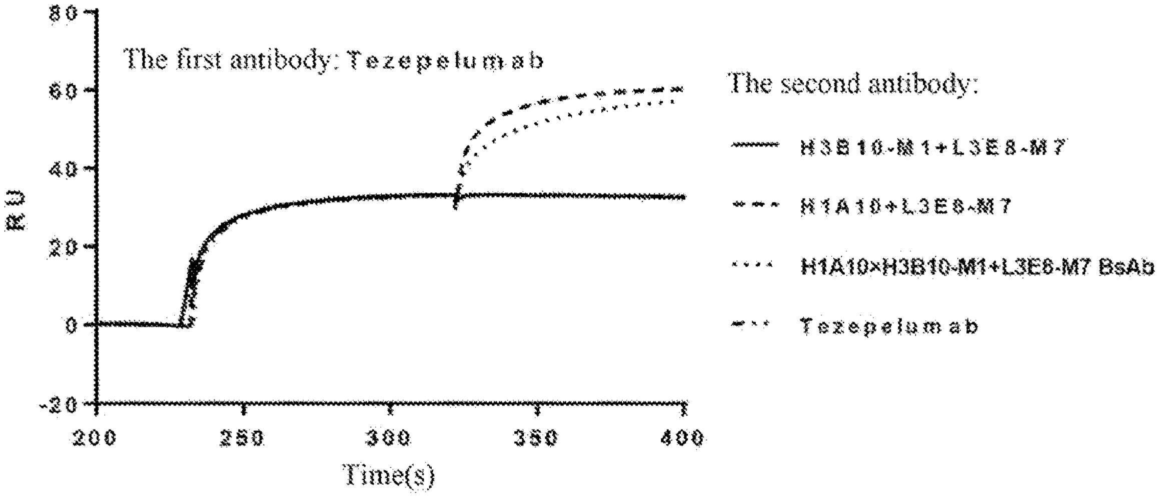

The results of the epitope analysis were shown as follows: 1) No binding signal of Tezepelumab was detected when first injecting H3B10-M1+L3E8-M7 and then Tezepelumab (FIG. 11A, Table 10); similarly, no binding signal of H3B10-M1+L3E8-M7 was detected when first injecting Tezepelumab and then H3B10-M1+L3E8-M7 (FIG. 11D, Table 10), indicating that the epitope of TSLP bound by H3B10-M1+L3E8-M7 was overlapped with that of TSLP bound by Tezepelumab. 2) The binding signals were significantly overlapped when first injecting H3B10-M1+L3E8-M7 and then H1A10+L3E8-M7 (FIG. 11A, Table 10); the binding signals were significantly overlapped when first injecting H1A10+L3E8-M7 and then H3B10-M1+L3E8-M7 (FIG. 11B, Table 10), indicating that H3B10-M1+L3E8-M7 and H1A10+L3E8-M7 recognized different TSLP epitopes. 3) After the bispecific antibody H1A10×H3B10-M1+L3E8-M7 (H1A10×H3B10-M1+L3E8-M7 BsAb) binding to TSLP, neither H3B10-M1+L3E8-M7 nor H1A10+L3E8-M7 can continue to bind to TSLP (FIG. 11C, Table 10), indicating that THE bispecific antibody H1A10×H3B10-M1 recognized the dual epitopes of TSLP.

TABLE 10

| Binding amount (RU) of the second antibody after the injection of the first antibody | | | | |
|---|---|---|---|---|
| | the first antibody | | | |
| the second antibody | H3B10-M1 + L3E8-M7 | H1A10 + L3E8-M7 | H1A10 × H3B10-M1 + L3E8-M7 BsAb | Tezepelumab |
| H3B10-M1 + L3E8-M7 | −2.4 | 28.1 | 25.1 | −2.1 |
| H1A10 + L3E8-M7 | 29.3 | −0.2 | 34.1 | 26.2 |
| H1A10 × H3B10-M1 + L3E8-M7 BsAb | 0.9 | 2.8 | 1.9 | 0.7 |
| Tezepelumab | −1.7 | 26.3 | 24 | −2 |

7.2 Binding Epitope Analysis of Anti-Human TSLP Antibody

TSLP binding epitope of anti-human TSLP monoclonal antibody H1A10+L3E8-M1 was analyzed. In order to study the binding epitope of humanized monoclonal antibody H1A10+L3E8-M1 to human TSLP, the recombinant H1A10+L3E8-M1 Fab and the recombinant human TSLP were prepared from CHO cells to forma aH1A10+L3F8-M1 Fab-TSLP complex. The complex crystal was formed under the conditions of 0.2M sodium formate and 20% PFG3350. X-ray diffraction experiment was performed on the complex crystal, and data with a resolution 2.23 Å were collected. The crystal structure of the TSLP antigen-antibody complex was analyzed by the molecular replacement method. The densities of the light and heavy chains and the electron density of the antigen in the H1A10+L3F8-M1 Fab-TSLP complex structure model were clear, and the values of R-work and R-free were 0.198 and 0.260, respectively.

Figure 12:
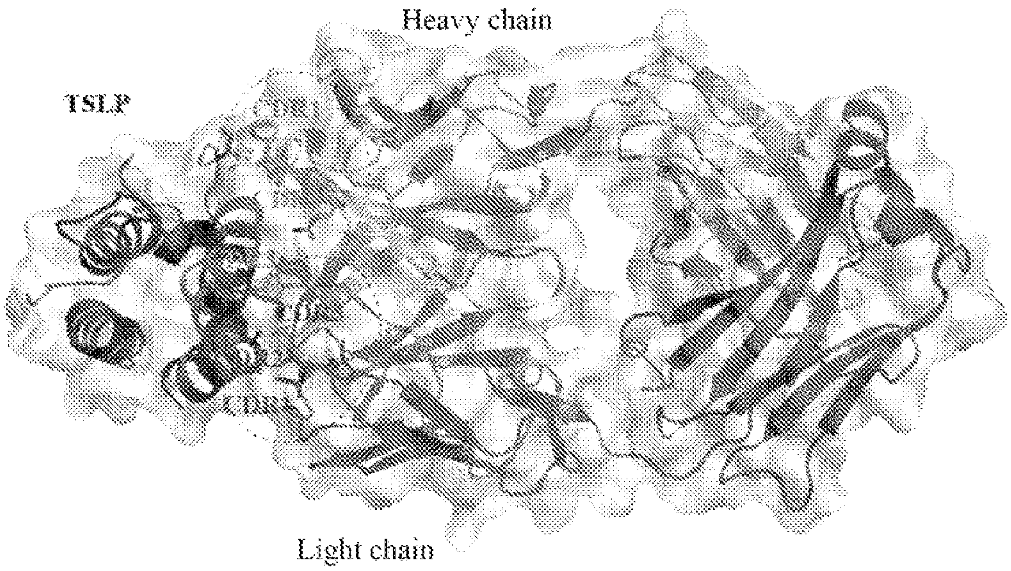
FIG. 12 shows the structural of an antibody-antigen complex, in which the TSLP antigen is shown on the left and H1A10+L3E8-M1 Fab is shown on the right.

The interaction area of TSLP with H1A10+L3F8-M1 Fab was about 895.1 A2, in which the interaction area of TSLP with the heavy chain was about 612.5 A2 and the interaction area of TSLP with the light chain was about 282.6 AW. The interactions mainly involve two helices of the amino acids at positions 41-53 and the amino acids at positions 95-114 of TSLP, whereas HCDR1, HCDR2, and HCDR3 of the heavy chain variable region of the antibody, as well as LCDR1 and LCDR3 of the light chain variable region of the antibody participated in the recognition of TSLP (FIG. 12). The key amino acid sites of the heavy chain involved in TSLP binding were N31, Q50, D57, Y101, G104, D55, and D57. The key amino acid sites of the light chain involved in the TSLP binding were N33, Y92, and Y95. The mode of the interaction of H1A10+L3E8-MT Fab with TSLP included hydrogen bonds, salt bonds, van der Waals forces, and hydrophobic interactions (see Table 11).

TABLE 11

| Amino acid residues involved in H1A10 + L3E8-M1 Fab-hTSLP binding | | | | | | |
|---|---|---|---|---|---|---|
| TSLP | | Heavy chain | | Light chain | | |
| Region | Residue | Region | Residue | Region | Residue | Interaction |
| α-A | A42 | CDR3 | Y101 | | | Hydrophobic interaction |
| | S45 | | | CDR1 | S32 | Hydrogen bond |
| | T46 | CDR3 | G104 | | | Hydrogen bond |
| | K49 | | | CDR1 | S30 | Van der Waals interaction |
| | | | | CDR1 | S32 | Van der Waals interaction |
| | D50 | | | CDR1 | N33 | Hydrogen bond |
| | T53 | | | CDR1 | S30 | Van der Waals interaction |
| BC ring | K95 | CDR2 | D59 | | | Van der Waals interaction |
| | M97 | | | CDR3 | S93 | Van der Waals interaction |
| | | | | CDR3 | S94 | Van der Waals interaction |
| | | | | CDR3 | Y95 | Hydrogen bond |
| α-C | M100 | CDR2 | Q50 | | | Hydrogen bond |
| | | CDR1 | W33 | | | Hydrogen bond |
| | | CDR2 | D59 | | | Van der Waals interaction |
| | | | | CDR3 | Y95 | Hydrogen bond |
| | | | | CDR3 | Y95 | Van der Waals interaction |
| | | | | CDR3 | W92 | Van der Waals interaction |
| | K101 | CDR2 | D55 | | | Salt bridge |
| | | CDR2 | D57 | | | Salt bridge |
| | | CDR3 | Y101 | | | Hydrogen bond |
| | | CDR3 | Y106 | | | Hydrogen bond |
| | | | | CDR1 | N33 | Hydrogen bond |
| | | | | CDR3 | W92 | Hydrogen bond |
| | | | | CDR3 | W92 | Van der Waals interaction |
| | K103 | CDR2 | P52 | | | Van der Waals interaction |
| | A104 | CDR3 | Y106 | | | Hydrogen bond |
| | A105 | CDR3 | Y101 | | | Hydrophobic interaction |
| | I108 | CDR3 | Y101 | | | Hydrophobic interaction |
| | | CDR1 | Y32 | | | Hydrogen bond |
| | W109 | CDR3 | Y101 | | | Hydrophobic interaction |

TABLE 11-continued

| Amino acid residues involved in H1A10 + L3E8-M1 Fab-hTSLP binding | | | | | | |
|---|---|---|---|---|---|---|
| TSLP | | Heavy chain | | Light chain | | |
| Region | Residue | Region | Residue | Region | Residue | Interaction |
| CD ring | S114 | CDR1 | N31 | | | Hydrogen bond |
| | | CDR2 | P52 | | | Van der Waals interaction |

The interaction of IL-7R with TSLP mainly involves the two helices of the amino acids at positions 41-49 and the amino acids at positions 97-109 of TSLP[28]. The TSLP epitopes bound by H1A10+L3E8-M1 mainly involve the amino acids at positions 41-53 and the amino acids at positions 95-114 of TSLP. The TSLP epitope bound by H1A10+L3E8-M1 was overlapped with the epitope TSLP bound by IL-7R. H1A10-L3E8-M1 inhibited the binding of TSLP to IL-7R. L3E8-M1 underwent a two-point mutation to become L3E8-M7, with the mutation sites L79V and S81A. These two sites were part of the structural stacking and spatially distant from the CDRs. The amino acids at these mutation positions were not involved in the binding to TSLP and did not affect the key amino acids binding to TSLP. Theoretically, it can be inferred that L3E8-M7 acts with TSLP in the same way that L3E8-M1 acts with TSLP, i.e., H1A10+L3E8-M7 and H1A10+L3E8-M1 act with TSLP in the same way.

The interaction of Tezepelumab with TSLP mainly involves the amino acids at positions 65-78 and the amino acids at positions 150-153 of TSLP. The interaction of TSLPR with TSLP mainly involves the amino acids at positions 60-69, the amino acids at positions 142-152 and the amino acids at positions 153-158 of TSLP[28]. That is, the TSLP epitope bound by Tezepelumab was overlapped with the TSLP epitope bound by TSLPR. The epitope analysis data of various monoclonal and bispecific antibodies in Section 7.1 showed that the TSLP epitope bound by H3B10-M1+L3E8-M7 was overlapped with the TSLP epitope bound by Tezepelumab. It can be inferred that the TSLP epitope bound by H3B10-M1+L3E8-M7 was overlapped with the TSLP epitope bound by TSLPR.

Example 8: Blocking of Human TSLP: TSLPR:IL-7Rα Complex Formation by Anti-Human TSLP Antibodies TSLP first binds to TSLPR on cell surface to form a binary complex, and then recruits IL-7Rα to form TSLP: TSLPR:IL-7Rα ternary complex before transducing the downstream signaling pathways. TSLP can bind to TSLPR with high affinity ($K_D$=32 nM). The interaction of TSLP with IL-7Rα was weak. However, IL-7Rφ can bind to TSLP: TSLPR complex with high affinity ($K_D$=29 nM)[28]. Functional anti-TSLP antibodies function primarily by blocking the formation of TSLP: TSLPR:IL-7Rα ternary complex in two ways: i) blocking the binding of TSLPR to TSLP, and ii) blocking the binding of IL-7Rα to TSLP: TSLPR binary complex.

Reagent Consumables

The reagent consumables, such as an amino coupling kit (BR-1000-50), a mouse antibody capture kit (BR100838), a S-series CM5 chip (BR100530), and 10×HBS-EP at pH 7.4 (BR100669) were all available from GE healthcare.

Chip Coupling

The surface of the carboxylated CM5 chip was activated with 1-ethyl-3-(3-dimethylaminopropyl) carbodiimide hydrochloride (EDC) and N-hydroxysuccinimide (NHS) according to the instructions in the amino coupling kit. An anti-mouse Fc (mFc) antibody (capture antibody) was diluted to 25 μg/mL with 10 Mm sodium acetate (pH 5.0), and then injected at a flow rate of 10 μL/min to achieve a coupling amount of approximately 10,000 response units (RU). After the injection of capture antibody, 1 M ethanolamine was injected to block the unreacted groups.

8.1 Blocking the Binding of Human TSLPR to Human TSLP by Anti-Human TSLP Antibodies The extracellular domain of human TSLP receptor (hTSLPR-ECD, SEQ ID NO:42) was expressed referring to Example 1. The recombinant protein hTSLP1-m-mFc was diluted to 2 μg/mL with 1×HBS-EP buffer, and was injected at 10 μL/min for 12s. Approximately 80 RU of hTSLP1-m-mFc was captured by the anti-mFc antibody. Anti-hTSLP antibodies (H3B10-M1+L3E8-M7, H1A10+L3E8-M7, and H1A10×H3B10-M1+L3E8-M7 BsAb) were diluted to 50 μg/mL with 1×HBS-EP buffer, and hTSLPR was diluted to 100 μg/mL. Two molecules were sequentially injected using a double injection mode of Biacore T200. That is, the anti-TSLP antibody (the first analyte) flowed through the surface of the chip capturing the antigen hTSLP1-m-mFc recombinant protein at a flow rate of 30 μL/min, followed by the injection of the same antibody or hTSLPR-ECD (the second analyte). Each of the molecules was injected for 90s. The surface of the chip was regenerated at the end of the injection by injecting 10 mM glycine-HCl (pH 1.7) at 10 μL/min for 30s. The Y-axis reporting points for the double baselines were zeroed using Biacore T200 evaluation software version 3.0, and then the RU values were plotted against times using GraphPad software.

Figure 13:
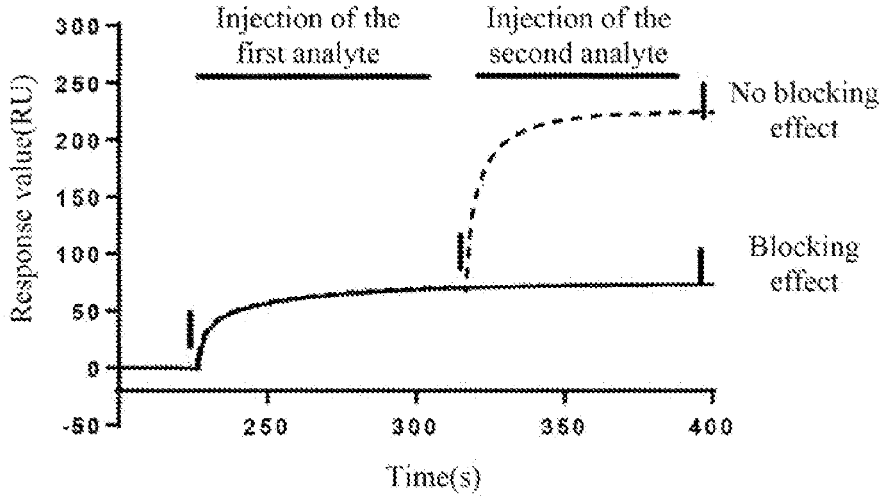
FIG. 13 shows the results of assessing the abilities of anti-human TSLP antibodies to block the binding of human TSLPR to human TSLP using Biacore T200.
Figure 13:
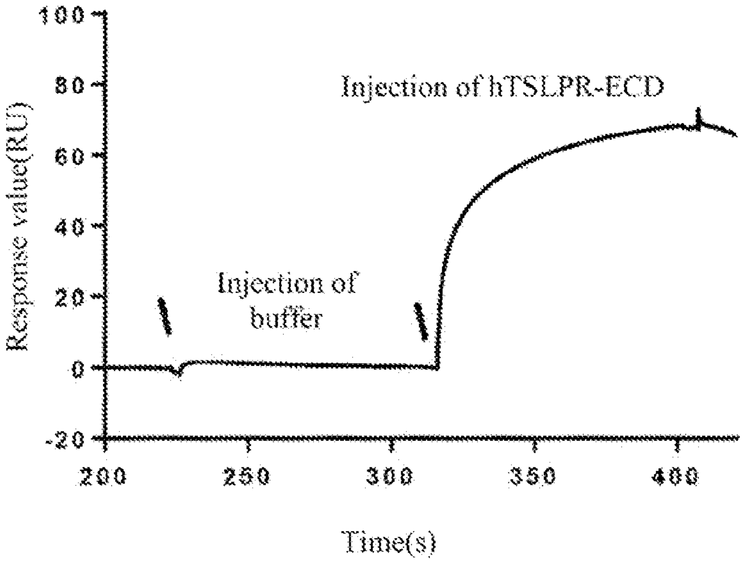
Figure 13:
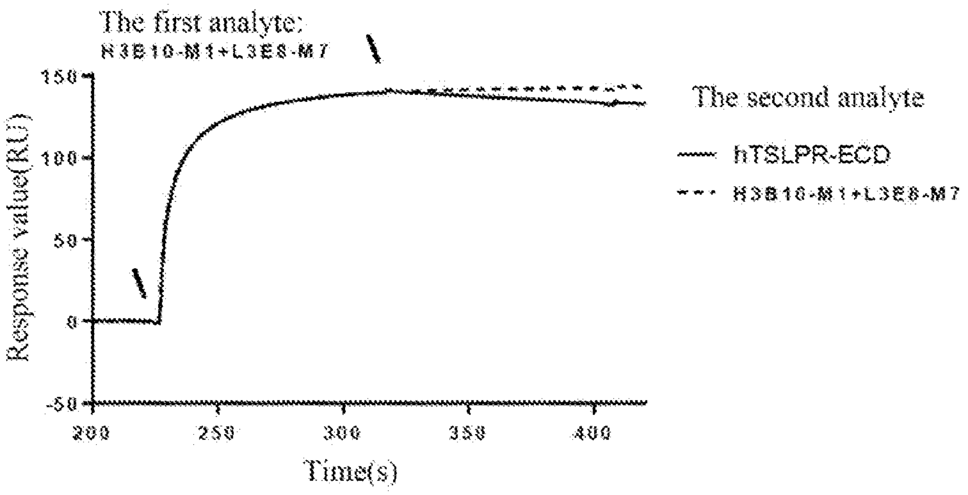
Figure 13:
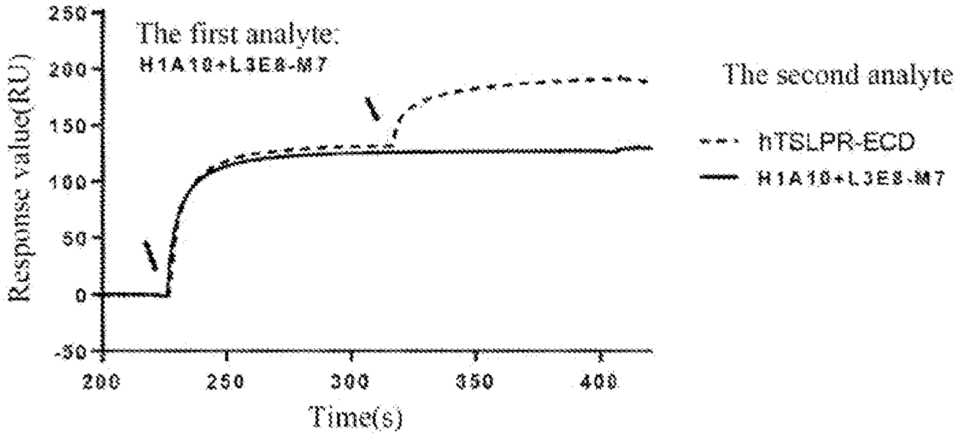
Figure 13:
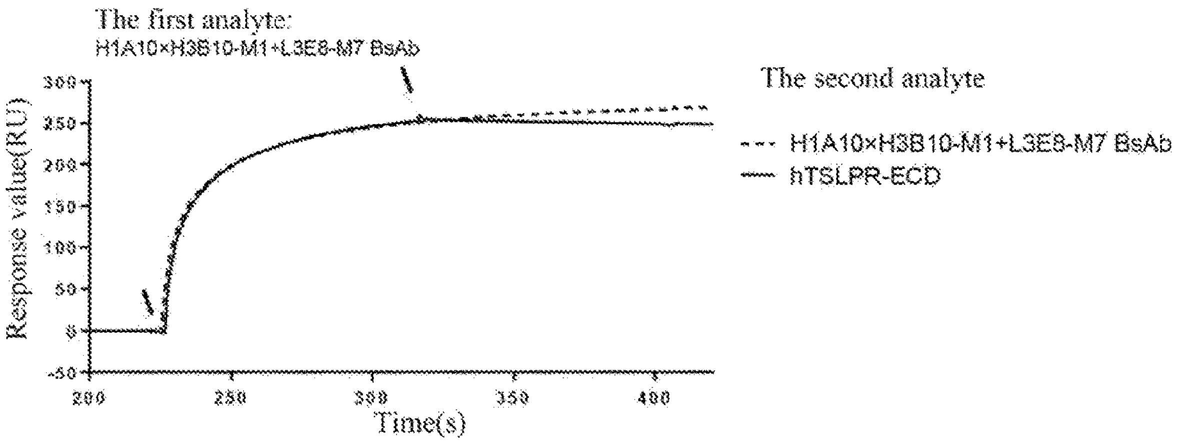

FIG. 13A shows the basic principle of protein blocking analysis using Biacore T200. The results were shown as follows: 1) When hTSLPR-ECD was injected alone, the binding amount of hTSLPR-ECD was 68.1 RU (FIG. 13B and Table 12). 2) No binding signal of hTSLPR-ECD was detected when first injecting H3B10-M1+L3E8-M7 and then hTSLPR-ECD (FIG. 13C and Table 12), indicating that H3B10-M1+L3E8-M7 blocked the binding of hTSLPR-ECD to the recombinant protein hTSLP1-m-mFc. 3) When first injecting H1A10+L3E8-M7 and then hTSLPR-ECD, the binding signal of hTSLPR-ECD was similar to that of hTSLPR-ECD alone (FIG. 13D and Table 12), indicating that H1A10+L3E8-M7 did not block the binding of hTSLPR-ECD to the recombinant protein hTSLP1-m-mFc. 4) hTSLPR-ECD can no longer continue to bind to the recombinant protein hTSLP1-m-mFc after the binding of H1A10×H3B10-M1+L3E8-M7 BsAb to the recombinant protein hTSLP1-m-mFc (FIG. 13E and Table 12), indicating that H1A10×H3B10-M1+L3E8-M7 BsAb can block the binding of hTSLPR-ECD to the recombinant protein hTSLP1-m-mFc.

TABLE 12

| Binding amount (RU) of hTSLPR-ECD after the injection of anti-hTSLP antibodies | |
|---|---|
| | Binding amount of HTSLPR-ECD |
| Buffer | 68.1 |
| H3B10-M1 + L3E8-M7 | −6 |
| H1A10 + L3E8-M7 | 59.1 |
| H1A10 × H3B10-M1 + L3E8-M7 BsAb | −1.7 |

8.2 Blocking the Binding of Human IL-7Rα to Human TSLP: TSLPR Complex by Anti-Human TSLP Antibodies The extracellular domain of human IL-7Rα (hIL-7Rα-ECD, SEQ ID NO:43) was expressed referring to Example 1. The recombinant proteins hTSLP1-m-mFc and hTSLPR-ECD were respectively diluted to 2 μg/mL and 100 μg/mL with 1×HBS-EP buffer. hTSLP1-m-mFc and hTSLPR-ECD were sequentially injected for 12s and 60s so as to form hTSLP: hTSLPR complex on the surface of the CM5 chip. Anti-hTSLP antibodies (H3B10-M1+L3E8-M7, H1A10+L3E8-M7 and H1A10×H3B10-M1+L3E8-M7 BsAb) were diluted to 50 μg/mL with 1×HBS-EP buffer, and hIL-7Rα-ECD was diluted to 200 μg/mL. Two molecules were sequentially injected using a double injection mode of Biacore T200. That is, the anti-TSLP antibody flowed through the surface of the chip capturing the hTSLP: hTSLPR complex at a flow rate of 30 μL/min, followed by the injection of hIL-7Rα-ECD. Each of the molecules was injected for 60s. The surface of the chip was regenerated at the end of the injection by injecting 10 mM glycine-HCl (pH 1.7) at 10 μL/min for 30s. The Y-axis reporting points for the double baselines were zeroed using Biacore T200 evaluation software version 3.0, and then the RU values were plotted against times using GraphPad software.

Figure 14:
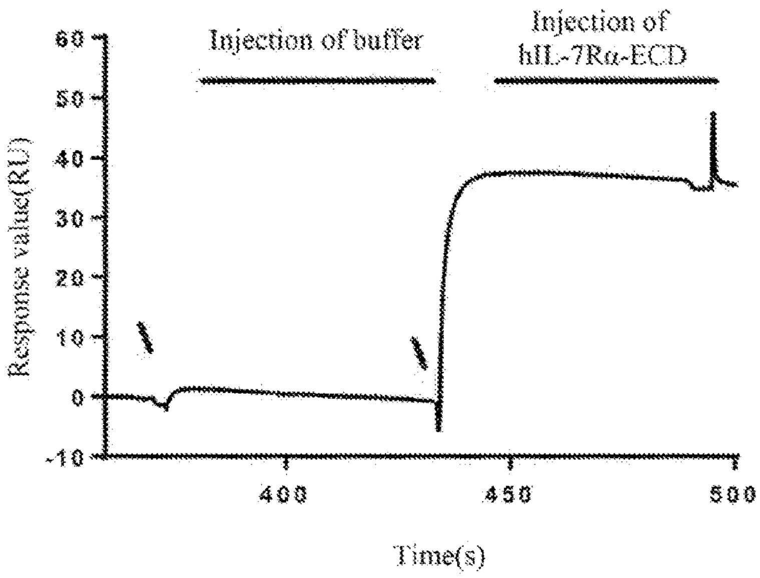
FIG. 14 shows the results of assessing the abilities of anti-human TSLP antibodies to block the binding of human IL-7Rα to human TSLP: TSLPR complex using Biacore T200.
Figure 14:
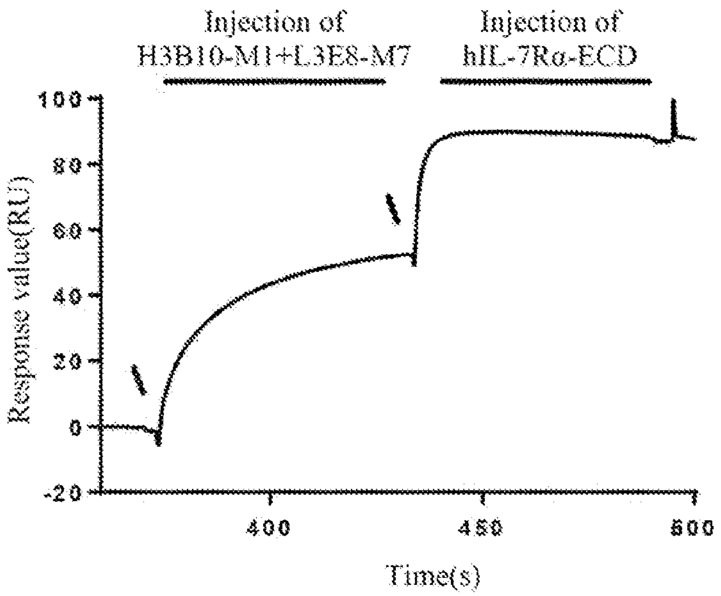
Figure 14:
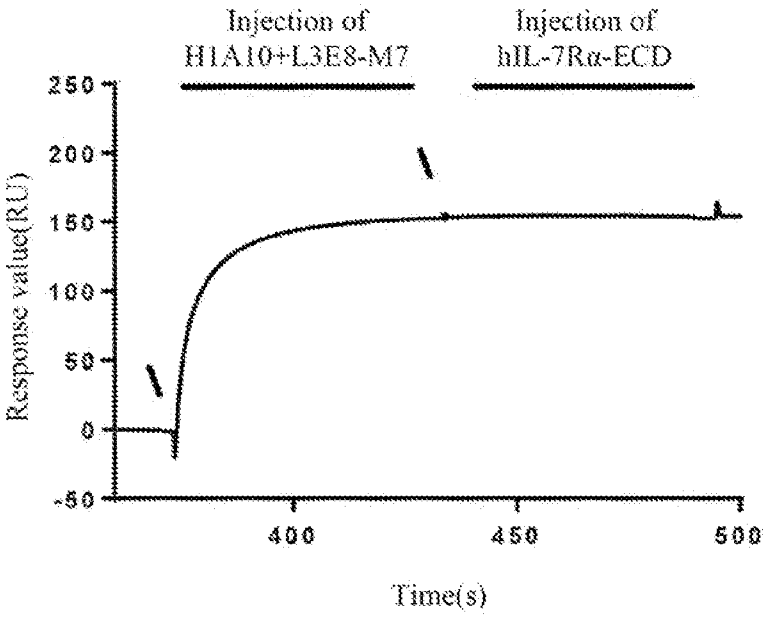
Figure 14:
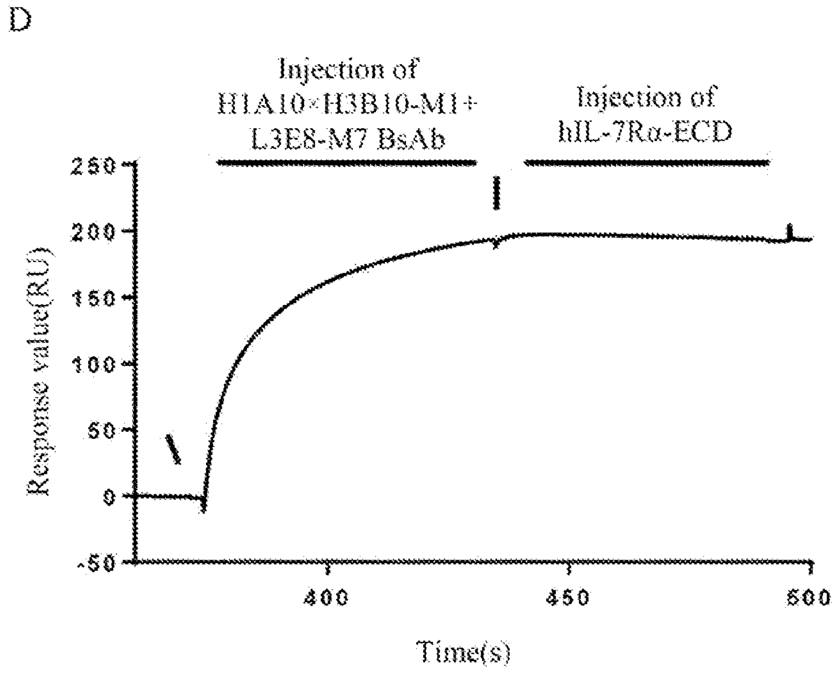

The results were shown as follows: 1) When hIL-7Rα-ECD was injected alone, the response value of the binding of hIL-7Rα-ECD to the hTSLP: hTSLPR complex was 36.2 RU (FIG. 14A and Table 13). 2) By first injecting H3B10-M1+L3E8-M7, and then hIL-7Rα-ECD, the binding signal of hIL-7Rα-ECD was similar to that of hIL-7Rα-ECD alone (FIG. 14B and Table 13), indicating that H3B10-M1+L3E8-M7 did not block the binding of hIL-7Rα-ECD to the hTSLP: hTSLPR complex. 3) No binding signal of hIL-7Rα-ECD was detected when first injecting H1A10+L3E8-M7, and then hIL-7Rα-ECD (FIG. 14C and Table 13), indicating that H1A10+L3E8-M7 can block the binding of hIL-7Rα-ECD to the hTSLP: hTSLPR complex. 4), hIL-7Rα-ECD cannot bind to the hTSLP: hTSLPR complex after the binding of H1A10×H3B10-M1+L3E8-M7 BsAb to hTSLP (FIG. 14D and Table 13), indicating that H1A10×H3B10-M1+L3E8-M7 BsAb can block the binding of hIL-7Rα-ECD to the hTSLP: hTSLPR complex.

TABLE 13

| Binding amount (RU) of hIL-7Rα-ECD after the injection of anti-TSLP antibodies | |
|---|---|
| | Binding amount of hIL-7Rα-ECD |
| Buffer | 36.2 |
| H3B10-M1 + L3E8-M7 | 36.5 |
| H1A10 + L3E8-M7 | 1.7 |
| H1A10 × H3B10-M1 + L3E8-M7 BsAb | 3.1 |

Exemplary embodiments of the present invention have been described above. However, those skilled in the art can modify or improve the exemplary embodiments described herein without departing from the spirit and scope of the present application, and variations or equivalents derived therefrom are also within the scope of the present application.

REFERENCE

1. Leonard, W. J. (2002) TSLP is now revealed to be an important regulator of DC-mediated control of TH2-based human allergic responses, identifying a potentially new species-specific function for this cytokine. Nat Immunol 3, 605-607.
2. Liu, Y. J., Soumelis, V., Watanabe, N., et al. (2007) TSLP: an epithelial cell cytokine that regulates T cell differentiation by conditioning dendritic cell maturation. Annual Review of Immunology 25, 93-219.
3. Ziegler, S. F., Artis, D. (2010) Sensing the outside world: TSLP regulates barrier immunity. Nat Immunol 11, 289-293.
4. Allakhverdi, Z., Comeau, M. R., Jessup, H. K., et al. (2009) Thymic stromal lymphopoietin as a mediator of crosstalk between bronchial smooth muscle and mast cells. Journal of Allergy and Clinical Immunology 123, 958-960.
5. Allakhverdi, Z., Comeau, M. R., Jessup, H. K., et al. (2007) Thymic stromal lymphopoietin is released by human epithelial cells in response to microbes, trauma, or inflammation and potently activates mast cells. J Exp Med 204, 253-258.
6. Lee, H. C., Ziegler, S. F. (2007) Inducible expression of the proallergic cytokine thymic stromal lymphopoietin in airway epithelial cells is controlled by NFκB. Proceedings of the National Academy of Sciences 104, 914-919.
7. Ying, S., O"Connor, B., Ratoff, J., et al. (2005) Expression and cellular provenance of thymic stromal lymphopoietin and chemokines in patients with severe asthma and chronic obstructive pulmonary disease. Journal of Allergy and Clinical Immunology 115, S9.
8. Gounni, A. S. (2007) Constitutive and inducible thymic stromal lymphopoietin expression in human airway smooth muscle cells: role in chronic obstructive pulmonary disease. American Journal of Physiology Lung Cellular & Molecular Physiology 293, 375-382.
9. Ying, S., O"Connor, B., Ratoff, J., et al. (2005). Thymic stromal lymphopoietin expression is increased in asthmatic airways and correlates with expression of th2-attracting chemokines and disease severity. The Journal of Immunology 174, 8183-8190.
10. Kashyap, M., Rochman, Y., Spolski, R., Samsel, L., et al. (2011) Thymic stromal lymphopoietin is produced by dendritic cells. The Journal of Immunology 187(3), 13-24.
11. Soumelis, V., Reche, P. A., Kanzler, H., et al. (2002) Human epithelial cells trigger dendritic cell mediator allergic inflammation by producing TSLP. Nat Immunol 3, 673-680.
12. Watanabe, N., Hanabuchi, S., Soumelis, V., et al. (2004) Human thymic stromal lymphopoietin promotes dendritic cell-mediated CD4+ T cell homeostatic expansion. Nat Immunol 5, 426-434.
13. Moon, P. D., Choi, I. H., Kim, H. M. (2011) Naringenin suppresses the production of thymic stromal lymphopoietin through the blockade of RIP2 and caspase-1 signal cascade in mast cells. European Journal of Pharmacology 671, 128-132.
14. Barton, G. M., Farr, A. G., et al. (2008) A mechanism for the initiation of allergen-induced T helper type 2 responses. Nature Immunology 9(3), 310-318.
15. He R, Geha, R. S. (2010) Thymic stromal lymphopoietin. Ann NY Acad Sci 1183, 13-24.
16. Oyoshi, M. K., Larson, R. P., Ziegler, S. F., et al. (2010) Mechanical injury polarizes skin dendritic cells to elicit a T (H) 2 response by inducing cutaneous thymic stromal lymphopoietin expression. Journal of Allergy & Clinical Immunology 126, 976-984; e975.
17. Hai yan Tu, Xin Chen, Jing Li. (2007) Signal transduction in respiratory syncytial virus infection-induced thymic stromal lymphopoietin expression in human epithelial cells. Journal of Southern Medical University 27(10), 1581-1583.
18. Medoff, B. D., Landry, A. L., Wittbold, K. A., et al. (2009) CARMA3 mediates lysophoshatidic acid-stimulated cytokine secretion by bronchial epithelial cells. American Journal of Respiratory Cell and Molecular Biology 2009(40), 286-294.
19. Park, L. S., Martin, U., Garka, K., et al. (2000) Cloning of the murine thymic stromal lymphopoietin (TSLP) receptor: formation of a functional heteromeric complex requires interleukin 7 receptor. The Journal of Experimental Medicine 192, 659-670.
20. Kenneth Verstraete, Frank Peelman, Harald Braun, et al. (2017) Structure and antagonism of the receptor complex mediated by human TSLP in allergy and asthma. Nature Communications 8, 14937.
21. GINA Report, Global Strategy for Asthma Management and Prevention. Available from: ginasthma.com.
22. von Bülow, Anna, Kriegbaum, M., Backer, V., et al. (2014) The prevalence of severe asthma and low asthma control among Danish adults. The Journal of Allergy and Clinical Immunology: In Practice 2(6), 759-673.
23. Reche, P. A., Soumelis, V. M., Gorman. D. M., et al. (2001) Human thyroid stromal lymphopoietin preferentially stimulates myeloid cells. The Journal of Immunology 167, 336-343.
24. Zhou, B., Comeau, M. R., De, S. T., et al. (2005) Thymic stromal lymphopoietin as a key initiator of allergic airway inflammation in mice. Nat Immunol 6, 1047-1053.
25. Zhuang gui Chen, Tian tuo Zhang, Hong tao Li, et al. (2013) Neutralization of TSLP inhibits airway remodeling in a murine model of allergic asthma induced by chronic exposure to house dust mite. PLoS One 8, e51268.
26. He, R., Oyoshi, M. K., Garibyan, L., et al. (2008). TSLP acts on infiltrating effector T cells to drive allergic skin inflammation. Proc Natl Acad Sci USA 105(33), 11875-11880.
27. Corren, J., Parnes, J. R., Wang, L., et al. (2017) Tezepelumab in Adults with Uncontrolled Asthma. New England Journal of Medicine 377(10), 936-946.
28. Verstraete K, Peelman F, Braun H, et al. 2017. Structure and antagonism of the receptor complex mediated by human TSLP in allergy and asthma. Nat Commun [J], 8: 14937.

What is claimed is:

1. A bispecific antibody comprising a first binding fragment and a second binding fragment that bind to non-overlapping epitopes of human thymic stromal lymphopoietin (TSLP) wherein the first binding fragment comprises a heavy chain variable region and a light chain variable region, wherein the heavy chain variable region comprises:

heavy chain complementarity determining region 1 (HCDR1) set forth in SEQ ID NO:29, heavy chain complementarity determining region 2 (HCDR2) set forth in SEQ ID NO:30, and heavy chain complementarity determining region 3 (HCDR3) set forth in SEQ ID NO:31; and the light chain variable region comprises:

light chain complementarity determining region 1 (LCDR1) set forth in SEQ ID NO:32, light chain complementarity determining region 2 (LCDR2) set forth in SEQ ID NO:33, and light chain complementarity determining region 3 (LCDR3) set forth in SEQ ID NO:34;

the second binding fragment comprises a heavy chain variable region and a light chain variable region, wherein the heavy chain variable region comprises:

HCDR1 set forth in SEQ ID NO:35,

HCDR2 set forth in SEQ ID NO: 36, and

HCDR3 set forth in SEQ ID NO: 37; and the light chain variable region comprises:

LCDR1 set forth in SEQ ID NO:32,

LCDR2 set forth in SEQ ID NO:33, and

LCDR3 set forth in SEQ ID NO:34; and wherein the amino acid sequences of HCDRs and LCDRs are defined according to Kabat.

2. The bispecific antibody according to claim 1, wherein the amino acid sequence of the heavy chain variable region of the first binding fragment is set forth in SEQ ID NO: 24, and the amino acid sequence of the light chain variable region of the first binding fragment is set forth in SEQ ID NO: 21; or the amino acid sequence of the heavy chain variable region of the first binding fragment is set forth in SEQ ID NO: 24, and the amino acid sequence of the light chain variable region of the first binding fragment is set forth in SEQ ID NO: 28.

3. The bispecific antibody according to claim 1, wherein the amino acid sequence of the heavy chain variable region of the second binding fragment is set forth in SEQ ID NO: 20, and the amino acid sequence of the light chain variable region of the second binding fragment is set forth in SEQ ID NO: 21; or the amino acid sequence of the heavy chain variable region of the second binding fragment is set forth in SEQ ID NO: 20, and the amino acid sequence of the light chain variable region of the second binding fragment is set forth in SEQ ID NO: 28.

4. The bispecific antibody according to claim 1, wherein the bispecific antibody is an IgG1 antibody comprising a first heavy chain constant region and a second heavy chain constant region, wherein the amino acids at positions 354 and 366 of the first heavy chain constant region are C and W, respectively, and the amino acids at positions 349, 366, 368 and 407 of the second heavy chain constant region are C, S, A and V, respectively; and/or the amino acids at positions 234, 235 and 331 of the first heavy chain constant region and the second heavy chain constant region are F, E and S, respectively;

and the amino acid positions of antibody constant regions are determined according to EU numbering.

5. The bispecific antibody according to claim 1, wherein the forms of the first binding fragment and the second binding fragment are independently selected from a single-chain fragment variable (scFv) or a Fab fragment; and/or the first binding fragment and the second binding fragment have the same light chain variable region.

6. The bispecific antibody according to claim 5, wherein both of the first binding fragment and the second binding fragment are Fab fragments.

7. The bispecific antibody according to claim 5, wherein the first binding fragment and the second binding fragment comprise the same light chain.

8. The bispecific antibody according to claim 1, wherein the bispecific antibody comprises a heavy chain as set forth in SEQ ID NO:38 and a light chain as set forth in one of SEQ ID NOs: 39 and 40; and/or the bispecific antibody comprises a heavy chain as set forth in SEQ ID NO:41 and a light chain as set forth in one of SEQ ID NOs: 39 and 40.

9. A monoclonal antibody that binds to human thymic stromal lymphopoietin (TSLP), comprising a heavy chain variable region and a light chain variable region, wherein the heavy chain variable region comprises:

heavy chain complementarity determining region 1 (HCDR1) set forth in SEQ ID NO:29, heavy chain complementarity determining region 2 (HCDR2) set forth in SEQ ID NO:30, and heavy chain complementarity determining region 3 (HCDR3) set forth in SEQ ID NO:31; and the light chain variable region comprises:

light chain complementarity determining region 1 (LCDR1) set forth in SEQ ID NO:32, light chain complementarity determining region 2 (LCDR2) set forth in SEQ ID NO:33, and light chain complementarity determining region 3 (LCDR3) set forth in SEQ ID NO:34;

wherein the amino acid sequences of HCDRs and LCDRs are defined according to Kabat.

10. The monoclonal antibody according to claim 9, wherein the amino acid sequence of the heavy chain variable region of the monoclonal antibody is set forth in SEQ ID NO: 24, and the amino acid sequence of the light chain variable region of the monoclonal antibody is set forth in SEQ ID NO:21; or the amino acid sequence of the heavy chain variable region of the monoclonal antibody is set forth in SEQ ID NO: 24, and the amino acid sequence of the light chain variable region of the monoclonal antibody is set forth in SEQ ID NO:28.

11. A pharmaceutical composition comprising the bispecific antibody of claim 1 and a pharmaceutically acceptable excipient, diluent, or carrier.

12. A pharmaceutical composition comprising the monoclonal antibody of claim 9 and a pharmaceutically acceptable excipient, diluent, or carrier.

13. A method of treating a TSLP-mediated disease, comprising administering to a subject in need thereof the bispecific antibody according to claim 1, wherein the TSLP-mediated disease is selected from the group consisting of asthma, scleroderma, systemic lupus erythematosus, rheumatoid arthritis, Churg-Strauss syndrome, Wegener's granulomatosis, allergic pneumonia, atopic dermatitis, rhinitis, Crohn's disease, psoriatic arthritis, chronic nephritis, Sjogren's syndrome, and multiple sclerosis.

14. A method of treating a TSLP-mediated disease, comprising administering to a subject in need thereof the monoclonal antibody according to claim 9; wherein the TSLP-mediated disease is selected from the group consisting of asthma, scleroderma, systemic lupus erythematosus, rheumatoid arthritis, Churg-Strauss syndrome, Wegener's granulomatosis, allergic pneumonia, atopic dermatitis, rhinitis, Crohn's disease, psoriatic arthritis, chronic nephritis, Sjogren's syndrome, and multiple sclerosis.

* * * * *